US 7,723,899 B2

(12) United States Patent
Blandino et al.

(10) Patent No.: US 7,723,899 B2
(45) Date of Patent: May 25, 2010

(54) ACTIVE MATERIAL AND LIGHT EMITTING DEVICE

(75) Inventors: Thomas P. Blandino, Cottage Grove, WI (US); Tai P. Luc, Oak Creek, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 678 days.

(21) Appl. No.: 11/639,904

(22) Filed: Dec. 15, 2006

(65) Prior Publication Data

US 2007/0159422 A1 Jul. 12, 2007

Related U.S. Application Data

(63) Continuation-in-part of application No. 11/464,419, filed on Aug. 14, 2006, now Pat. No. 7,538,473, and a continuation-in-part of application No. 11/265,738, filed on Nov. 2, 2005, which is a continuation-in-part of application No. 11/050,169, filed on Feb. 3, 2005.

(60) Provisional application No. 60/541,067, filed on Feb. 3, 2004.

(51) Int. Cl.
*H01L 41/09* (2006.01)
*H02N 2/06* (2006.01)

(52) U.S. Cl. ..................................... 310/317
(58) Field of Classification Search ......... 310/317–319; 315/185 S, 200 A; 327/518
See application file for complete search history.

(56) References Cited

U.S. PATENT DOCUMENTS 3,589,563 A 6/1971 Carragan et al.
4,113,809 A 9/1978 Abair et al.
4,228,440 A 10/1980 Horike et al.
4,632,311 A 12/1986 Nakane et al.
4,833,358 A 5/1989 Suzuki et al.
4,849,872 A 7/1989 Gässler
4,866,580 A 9/1989 Blackerby
4,877,989 A 10/1989 Drews et al.
4,973,876 A 11/1990 Roberts
5,006,724 A 4/1991 Liu
5,008,595 A 4/1991 Kazar
5,087,850 A 2/1992 Suzuta
5,097,180 A 3/1992 Ignon et al.
5,105,143 A * 4/1992 Marumoto et al. ............ 322/28
5,128,595 A 7/1992 Hara
5,297,734 A 3/1994 Toda (Continued)

FOREIGN PATENT DOCUMENTS

| DE | 297 13 945 | | 10/1997 |
|---|---|---|---|
| DE | 201 03 621 | | 5/2001 |
| EP | 480 615 | | 4/1992 |
| EP | 0690580 | * | 3/1996 |
| EP | 824 022 | | 2/1998 |

(Continued)

OTHER PUBLICATIONS

International Search Report in PCT/US2006/042971 dated Mar. 22, 2007.

(Continued)

*Primary Examiner*—Walter Benson
*Assistant Examiner*—Derek J Rosenau

(57) ABSTRACT

An active material and light emitting device comprises an ultrasonic atomizer assembly and a light emission device. The active material and light emitting device are operated such that the active material is periodically or aperiodically dispensed and the light emitting device flickers to simulate a real candle.

22 Claims, 34 Drawing Sheets

U.S. PATENT DOCUMENTS

| | | |
|---|---|---|
| 5,311,093 A | 5/1994 | Mukohjima |
| 5,452,711 A | 9/1995 | Gault |
| 5,462,839 A | 10/1995 | de Rooij et al. |
| 5,551,416 A | 9/1996 | Stimpson et al. |
| 5,673,825 A | 10/1997 | Chen |
| 5,777,445 A | 7/1998 | Motegi |
| 5,828,295 A | 10/1998 | Mittel et al. |
| 5,842,763 A | 12/1998 | Lakosky |
| 5,924,784 A | 7/1999 | Chliwnyj |
| 5,955,819 A | 9/1999 | Takano et al. |
| 5,970,974 A | 10/1999 | Van Der Linden et al. |
| 6,066,924 A | 5/2000 | Lederer |
| 6,100,654 A | 8/2000 | Izukawa et al. |
| 6,196,219 B1 | 3/2001 | Hess et al. |
| 6,198,198 B1 | 3/2001 | Fujimura et al. |
| RE37,168 E | 5/2001 | St. Louis |
| 6,234,017 B1 | 5/2001 | Stevens et al. |
| 6,296,196 B1 | 10/2001 | Denen et al. |
| 6,362,578 B1 | 3/2002 | Swanson et al. |
| 6,400,096 B1 | 6/2002 | Wells et al. |
| 6,405,934 B1 | 6/2002 | Hess et al. |
| 6,483,226 B1 | 11/2002 | Okada |
| 6,508,411 B1 | 1/2003 | Ohnishi et al. |
| 6,554,203 B2 | 4/2003 | Hess et al. |
| 6,586,890 B2 | 7/2003 | Min et al. |
| 6,608,426 B2 | 8/2003 | Hayashi et al. |
| 6,616,308 B2 | 9/2003 | Jensen et al. |
| 6,639,367 B2 | 10/2003 | Wells et al. |
| 6,644,507 B2 | 11/2003 | Borut et al. |
| 6,680,620 B2 | 1/2004 | Hedenetz et al. |
| 6,719,443 B2 | 4/2004 | Gutstein et al. |
| 6,720,705 B2 | 4/2004 | Nakatsuka et al. |
| 6,722,582 B2 | 4/2004 | Hess et al. |
| 6,747,391 B1 | 6/2004 | Ben-Yaakov |
| 6,802,460 B2 | 10/2004 | Hess et al. |
| 6,803,699 B2 | 10/2004 | Yuasa et al. |
| 6,805,303 B2 | 10/2004 | Hess et al. |
| 6,815,871 B2 | 11/2004 | Yuasa et al. |
| 6,819,027 B2 | 11/2004 | Saraf |
| 6,828,712 B2 | 12/2004 | Battaglin et al. |
| 6,836,081 B2 | 12/2004 | Swanson et al. |
| 6,843,430 B2 | 1/2005 | Boticki et al. |
| 6,844,658 B2 | 1/2005 | Hoshino |
| 6,891,311 B2 | 5/2005 | Phelps et al. |
| 6,926,423 B2 | 8/2005 | Bucher et al. |
| 7,049,752 B2 | 5/2006 | Tani et al. |
| 7,049,761 B2 * | 5/2006 | Timmermans et al. ...... 315/246 |
| 7,061,157 B2 | 6/2006 | Battaglin et al. |
| 7,332,878 B1 | 2/2008 | Smith |
| 2003/0016824 A1 | 1/2003 | Epstein |
| 2003/0192959 A1 | 10/2003 | Hess et al. |
| 2004/0124173 A1 | 7/2004 | Hess et al. |
| 2004/0200907 A1 | 10/2004 | Martens et al. |
| 2004/0251778 A1 | 12/2004 | Hoshino |
| 2004/0263567 A1 | 12/2004 | Hess et al. |
| 2005/0067921 A1 | 3/2005 | Yamamoto |
| 2005/0140315 A1 * | 6/2005 | Baldwin et al. ............ 315/308 |
| 2005/0166945 A1 | 8/2005 | Whitmore |
| 2005/0169666 A1 | 8/2005 | Porchia et al. |
| 2005/0169812 A1 | 8/2005 | Helf et al. |
| 2005/0185392 A1 | 8/2005 | Walter et al. |
| 2005/0196716 A1 | 9/2005 | Haab et al. |
| 2005/0205916 A1 | 9/2005 | Conway et al. |
| 2005/0219302 A1 | 10/2005 | Vogeley |
| 2005/0225201 A1 | 10/2005 | Vogeley |
| 2005/0225202 A1 | 10/2005 | Vogeley et al. |
| 2005/0230495 A1 | 10/2005 | Feriani et al. |
| 2005/0242685 A1 | 11/2005 | Yuasa |
| 2005/0280334 A1 | 12/2005 | Ott et al. |
| 2006/0001332 A1 | 1/2006 | Ollila |
| 2006/0049716 A1 | 3/2006 | Yuasa |
| 2006/0055284 A1 | 3/2006 | Hoshino |
| 2006/0056999 A1 | 3/2006 | East |
| 2006/0061232 A1 | 3/2006 | Min et al. |
| 2006/0071614 A1 | 4/2006 | Tripathi et al. |
| 2006/0091826 A1 | 5/2006 | Chen |
| 2006/0115386 A1 | 6/2006 | Michaels et al. |
| 2006/0120080 A1 | 6/2006 | Sipinski et al. |
| 2006/0125420 A1 | 6/2006 | Boone et al. |
| 2006/0175426 A1 | 8/2006 | Schramm et al. |
| 2006/0192728 A1 | 8/2006 | Kim |
| 2006/0197469 A1 | 9/2006 | Kim |
| 2006/0208666 A1 | 9/2006 | Johnson |
| 2007/0154857 A1 | 7/2007 | Cho |
| 2007/0177393 A1 | 8/2007 | Hirata |
| 2008/0073443 A1 | 3/2008 | Tollens et al. |
| 2008/0074875 A1 | 3/2008 | Jensen et al. |
| 2008/0129226 A1 | 6/2008 | DeWitt et al. |

FOREIGN PATENT DOCUMENTS

| | | |
|---|---|---|
| EP | 824 023 | 2/1998 |
| EP | 923 957 | 6/1999 |
| EP | 937 478 | 8/1999 |
| EP | 1 005 917 | 6/2000 |
| EP | 1 103 653 | 5/2001 |
| EP | 1 184 083 | 3/2002 |
| EP | 1 287 904 | 3/2003 |
| EP | 1 287 905 | 3/2003 |
| GB | 2 398 627 | 8/2004 |
| JP | 38-10166 | 5/1938 |
| JP | 43-14553 | 6/1943 |
| JP | 54-167416 | 11/1979 |
| JP | 60-29149 | 2/1985 |
| JP | 61-138557 | 6/1986 |
| JP | 62-27644 | 2/1987 |
| JP | 62-32962 | 2/1987 |
| JP | 62-119941 | 7/1987 |
| JP | 63-3839 | 1/1988 |
| JP | 63-36282 | 3/1988 |
| JP | 63-155379 | 10/1988 |
| JP | 63-182754 | 11/1988 |
| JP | 1-149966 | 10/1989 |
| JP | 2-187165 | 7/1990 |
| JP | 2-114048 | 9/1990 |
| JP | 2-220665 | 9/1990 |
| JP | 3-47262 | 2/1991 |
| JP | 3-63058 | 3/1991 |
| JP | 3-73156 | 3/1991 |
| JP | 3-60956 | 6/1991 |
| JP | 3-159652 | 7/1991 |
| JP | 3-234262 | 10/1991 |
| JP | 4-30859 | 2/1992 |
| JP | 4-27940 | 3/1992 |
| JP | 4-150968 | 5/1992 |
| JP | 4-156855 | 5/1992 |
| JP | 4-207798 | 7/1992 |
| JP | 4-207799 | 7/1992 |
| JP | 4-207800 | 7/1992 |
| JP | 4-338468 | 11/1992 |
| JP | 4-371257 | 12/1992 |
| JP | 5-156 | 1/1993 |
| JP | 5-24044 | 3/1993 |
| JP | 5-184993 | 7/1993 |
| JP | 5-212331 | 8/1993 |
| JP | 5-261324 | 10/1993 |
| JP | 5-305257 | 11/1993 |
| JP | 6-320083 | 11/1994 |
| JP | 6-320084 | 11/1994 |
| JP | 6-335646 | 12/1994 |
| JP | 6-335647 | 12/1994 |
| JP | 7-8865 | 1/1995 |
| JP | 7-24375 | 1/1995 |
| JP | 7-116574 | 5/1995 |

| | | |
|---|---|---|
| JP | 8-52216 | 2/1996 |
| JP | 8-071470 | 3/1996 |
| JP | 2511119 | 6/1996 |
| JP | 8-215308 | 8/1996 |
| JP | 8-281165 | 10/1996 |
| JP | 2544634 | 5/1997 |
| JP | 09-201155 | 8/1997 |
| JP | 9-244575 | 9/1997 |
| JP | 11-221505 | 8/1999 |
| JP | 2001-070851 | 3/2001 |
| JP | 2002-086035 | 3/2002 |
| JP | 2003-181347 | 7/2003 |
| WO | WO 00/47335 | 8/2000 |
| WO | WO 02/068128 | 9/2002 |
| WO | WO 03/068412 | 8/2003 |
| WO | WO 03/068413 | 8/2003 |
| WO | WO 2005/097348 | 10/2005 |
| WO | WO 2005/098982 | 10/2005 |
| WO | WO 2007/045831 | 4/2007 |
| WO | WO 2007/045832 | 4/2007 |
| WO | WO 2007/045834 | 4/2007 |
| WO | WO 2007/045835 | 4/2007 |
| WO | WO 2008/016867 | 2/2008 |
| WO | WO 2008/035303 | 3/2008 |

OTHER PUBLICATIONS

Written Opinion in PCT/US2006/042971 dated Mar. 22, 2007.
International Search Report and Written Opinion in PCT/US2007/025160 dated Apr. 11, 2008.
International Search Report and Written Opinion in PCT/US2006/042919 dated Apr. 20, 2007.
PCT/US2007/025539 International Search Report and Written Opinion dated Jun. 22, 2009.
Office Action in U.S. Appl. No. 11/140,329 dated Apr. 27, 2007.
Office Action in U.S. Appl. No. 11/050,242 dated Jul. 19, 2007.
Office Action in U.S. Appl. No. 11/050,169 dated Oct. 15, 2008.
Office Action in U.S. Appl. No. 11/264,952 dated Oct. 24, 2008.

* cited by examiner

ACTIVE MATERIAL AND LIGHT EMITTING DEVICE

CROSS REFERENCE TO RELATED APPLICATIONS

This application is a continuation-in-part of U.S. application Ser. No. 11/265,738, filed Nov. 2, 2005, entitled "Active Material and Light Emitting Device, which is a continuation-in-part of U.S. application Ser. No. 11/050,169, filed Feb. 3, 2005, entitled "Device Providing Coordinated Emission of Light and Volatile Active," which claims the benefit of U.S. Provisional Application No. 60/541,067, filed Feb. 3, 2004, and also is a continuation-in-part of U.S. application Ser. No. 11/464,419, filed on Aug. 14, 2006, now U.S. Pat. No. 7,538,473, entitled "Drive Circuits And Methods For Ultrasonic Piezoelectric Actuators."

REFERENCE REGARDING FEDERALLY SPONSORED RESEARCH OR DEVELOPMENT

Not Applicable

SEQUENTIAL LISTING

Not Applicable

BACKGROUND OF THE INVENTION

1. Field of the Invention

The present invention relates to the integrated presentation of ambient conditions. More specifically, the present invention relates to the controlled and coordinated emission of light and an active material, into a given area, such as a room, from a single device.

2. Description of the Background of the Invention

Because of their wide array of shapes and sizes, as well as the seemingly limitless number of available scents, few things are quite as versatile at setting the ambience in an area as scented candles. Scented candles are not without drawbacks, however. For example, dripping wax can damage furniture and the skin and, in the extreme, an open flame can lead to a structure fire.

To account for the common problems associated with candles, electronic lighting devices that have a flickering candle appearance, such as those disclosed in U.S. Pat. Nos. 5,013,972 and 6,066,924, are generally known in the art. In the '972 patent, two side-by-side lamps are alternatingly turned on and off at such frequencies that a flickering is perceived. Similarly, the '924 patent discloses circuitry used to control two light bulbs in close proximity to each other such that the bulbs flicker. Moreover, the circuitry and bulbs of the '924 patent are contained within a container of a size and shape similar to common flat candles. While these patents may suggest devices that mimic the visual aesthetics of a candle, they fail to provide the scented candle experience, i.e., they fail to emit fragrance in addition to light.

Fragrance dispensers are also generally known. For example, it is known to emit fragrance from an aerosol container upon the activation of a trigger by a user. Also, other methods utilize the evaporative properties of liquids, or other vaporizable materials, to cause vapors with desired properties to be distributed into the ambient air. For example, U.S. Pat. No. 4,413,779 discloses a glass container containing a fluid into which two rigid porous nylon wicks extend. The wicks contact a rigid plastic porous element. In use, the wicks transport the fluid from the glass container to the ambient air. As a further example of air fresheners, the art is also generally aware of atomizer assemblies for releasing fragrance from a wick that draws fragrant liquid from a reservoir. For example, commonly assigned U.S. Pat. No. 6,296,196 and commonly assigned and copending U.S. patent application Ser. No. 10/412,911, filed Apr. 14, 2003, both discussed in detail below, disclose such assemblies. These references are hereby incorporated by reference. Although these representative devices provide fragrance emission, they do not provide the visual aesthetic of a candle.

SUMMARY OF THE INVENTION

According to one aspect of the present invention, a light and active material emitting circuit includes an LED and a microprocessor that develops a pulse-width modulated (PWM) waveform. A first feedback circuit is coupled to the LED and an integrator has a first input that receives the PWM waveform, a second input coupled to the first feedback circuit, and an output. An oscillator is coupled to the integrator and includes a logic gate, a first impedance coupled across the logic gate providing positive feedback and a second impedance coupled across the logic gate providing negative feedback. A drive circuit is coupled to the oscillator and a first inductor is coupled between the driver and the LED wherein the LED is caused to flicker. The circuit further includes a piezoelectric actuator and a second inductor coupled to the piezoelectric actuator wherein the piezoelectric actuator and the second inductor form a resonant circuit. A plurality of transistors is coupled to the resonant circuit and a second feedback circuit is coupled to the plurality of transistors. A control circuit is coupled to the second feedback circuit and has an amplifier and an inverter, wherein the control circuit is further coupled to the transistors wherein the control circuit develops the drive waveforms such that the piezoelectric actuator is periodically driven at a resonant frequency.

According to a further aspect of the present invention, a circuit for developing drive waveforms for switches coupled to a resonant circuit comprises a feedback circuit coupled to the resonant circuit and a control circuit coupled to the feedback circuit and having first and second interconnected NAND gates. The control circuit is coupled to the switches and develops the drive waveforms wherein the resonant circuit is driven at a resonant frequency.

According to another aspect of the present invention, a circuit for developing a drive waveform for an LED includes a microprocessor that develops a pulse-width modulated (PWM) waveform and a feedback circuit coupled to the LED. An integrator has a first input that receives the PWM waveform, a second input coupled to the feedback circuit, and an output. An oscillator is coupled to the integrator including a logic gate, a first impedance coupled across the logic gate providing positive feedback and a second impedance coupled across the logic gate providing negative feedback. A drive circuit is coupled to the oscillator and an inductor is coupled between the drive circuit and the LED wherein the LED is caused to flicker.

Other aspects and advantages of the present invention will become apparent upon consideration of the following detailed description.

BRIEF DESCRIPTION OF THE DRAWINGS

Throughout the FIGS., like or corresponding reference numerals have been used for like or corresponding parts.

DETAILED DESCRIPTION OF THE PREFERRED EMBODIMENTS

Figure 1:
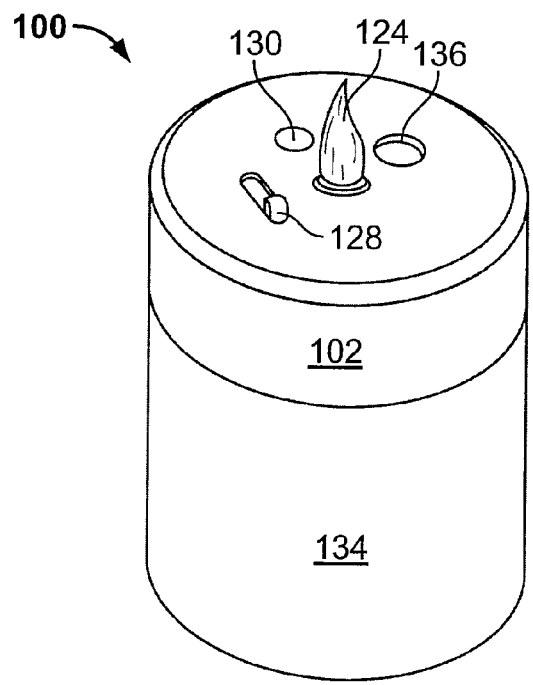
FIG. 1 is a perspective view of a light and active material emitting device according to a first embodiment.

The present invention provides a device that emits both light and an active material. Preferably, the present invention provides a single device that mimics both the visual and olfactory aesthetic of a scented candle, without an open flame and with an improved fragrance delivery system.

While a preferred embodiment of the present invention includes emission of an active material, preferably a fragrance, and much of the discussion below will be with regard to emission of a fragrance, we also contemplate that the dispenser may alternatively dispense other substances, such as a disinfectant, a sanitizer, an insecticide, an insect repellant an, insect attractant, air purifiers, aromatherapy, scents, antiseptics, odor eliminators, air-fresheners, deodorizers, and other active ingredients that are usefully dispersed into the air. As will be recognized by one of ordinary skill in the art, other active ingredients can be introduced to the ambient environment via dispensers in much the same way as fragrances.

As generally seen in the FIGS., preferred embodiments of the present invention include a device for emitting light and an active material. The device preferably includes an electrically-powered light source, an active material dispenser, a power source, control circuitry, and a support structure. All of these components work together to provide a fragrant aroma and the appearance of a flickering flame, the flickering effect being provided by the electrically-powered light source.

Light Source

The light source is an electrically-powered light emitting device. The light source comprises one or more light emitting diodes (LED's). Particularly, in FIGS. 1-7 a single LED 106 or 206 is used, while in FIGS. 8A-8C, the light source includes LED's 306a, 306b. Other conventional lighting devices (including, for example, incandescent, halogen, fluorescent, etc.) may alternatively be used as the light source.

As is generally understood, LED's offer various features not found in other conventional lighting devices. In particular, as is well known in the art, by manipulating the duty cycle of an LED, light emitted from the LED can be controlled. For example, light can be emitted at perceptible intermittencies, or it can be emitted such that it is perceived to be continually emitted. Moreover, increasing the duty cycle of an LED will increase the intensity of light emitted and/or the perceived color.

In the embodiments in which a single LED is used, the LED is controlled to have a varying intensity, thereby providing a flickering effect. When two LED's are used, as in FIGS. 8A-8C, the two LED's 306a, 306b are preferably arranged one above the other, i.e., the LED306a is on a side of the LED 306b opposite to a base of the light and fragrance emitting device 300. Preferably, the upper LED 306a is controlled to emit light at a perceivable intermittence, while the lower LED 306b is controlled such that light is perceived to be emitted continuously. In this fashion, the LED's 306a, 306b work to create a flicker effect. When, for example, a conventional candle is lit, the base of the flame is steady, while the portion of the flame further from the wick appears to flicker. The present arrangement of the LED's 306a, 306b mimics this visual characteristic. It is preferred that LED's having a yellowish or amber hue be used. Specifically, it is preferred that the LED's used have a wavelength of emission in the range of from approximately 580 nanometers to approximately 600 nanometers, and it is even more preferred that the LED's used have a wavelength of emission in the range of from approximately 585 nanometers to approximately 595 nanometers. Optionally, the LED's 306a, 306b may be positioned side-by-side instead of one above the other. Still optionally, one or both of the LED's 306a, 306b may be white and a color or image filter may be disposed over the LED to project an image or a color therefrom.

Of course, we anticipate modifications to the light source of our preferred embodiment. For example, more than two LED's can be used, perhaps, to create the perception of a larger flame. Also, LED's of many colors are known and could be used, for example to more closely resemble a flame by using hues that are reddish, orangish, and/or yellowish. The colors can also be made to change, for example, using RGB LED's. By so varying the types of LED's used, as well as their arrangement, numerous aesthetics can be obtained, including varied colored shows, colored flames, and colored flickers. And, by adjusting the duty cycles of the LED's, the brightness of the light may also be reduced or intensified, as dictated by design preference.

Moreover, when multiple LED's are used, it is not required that one LED provide a perceptibly constant light emission while the other LED 306a provides a flicker effect. One or both may be held perceptibly constant and one or both may emit flickering light. (It would be recognized by one of ordinary skill in the art that when using pulse-width modulation to control one or more LED's perceptibly constant and flicking lights are likely both being flickered at a high frequency imperceptible to an observer. Flickering and constant light should be understood herein to refer to perceived effects.)

Active Material Dispenser

An active material dispenser is preferably provided integrally with the present invention. The active material dispenser preferably holds a replaceable container, or reservoir, having an active material in any one of a number of conventional forms, including gel and liquid forms. The active material may be vaporized by the application of heat and emanated from the device. In such a case, the dispenser may have a controllable heating device to vary the rate at which vapor is driven from the fragrance or a mechanical controller for controlling the airflow around the fragrance to be vaporized (such as a shield or fan).

Figure 13:
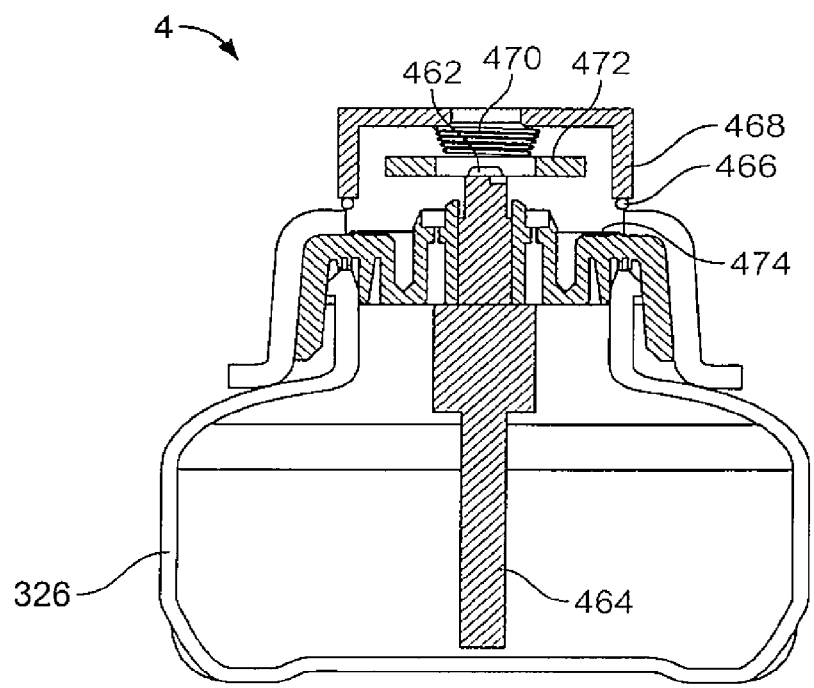
Figure 14:
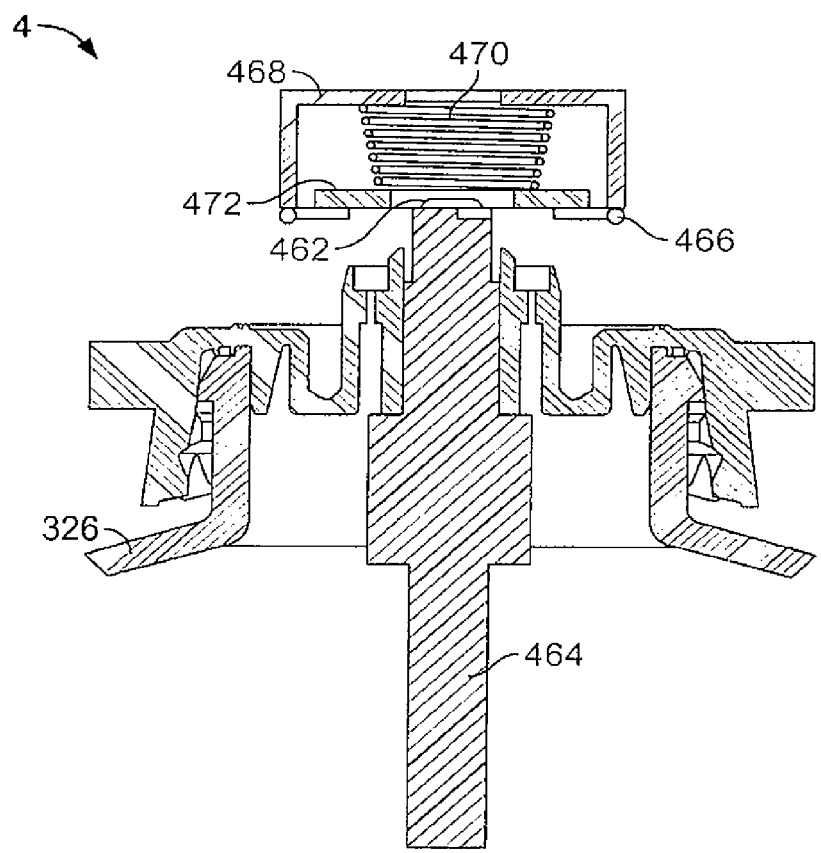
FIG. 14 is a cross-sectional view illustrating the active material dispenser shown in FIG. 13.

While active material dispensers are generally well known, a preferred active material dispenser is a wick-based emanation system. More preferably, the active material dispenser uses an atomizer to emanate the active material from the wick. Such an arrangement is shown in FIGS. 13 and 14.

Specifically, the evaporative active material dispenser 4 comprises an atomizer assembly including an orifice plate 462, and a replaceable reservoir 326. The reservoir 326 is replaceable and contains an active material in the form of a fluid. A wick 464 is disposed in the reservoir 326. The wick 464 operates by capillary action to transfer liquid from within the reservoir 326. The reservoir 326 is preferably removable by a user and may be replaced with another reservoir 326 (for example, when the fluid is exhausted or when a different type of fluid is desired). When replaced in this manner, the wick 464 transfers fluid from the reservoir 326.

In addition to including the orifice plate 462, the atomizer assembly further comprises at least one resilient, elongated wire-like support 466 shaped to resiliently support the lower surface of the orifice plate 462 and a spring housing 468. A spring 470, contained within the spring housing 468, resiliently presses on the upper surface of the orifice plate 462. Rather than pressing on the orifice plate 462 directly, the spring 470 may alternatively, or additionally, press on a member, such as an actuator element 472 (made of, for example, piezoelectric ceramic material, which is connected to the orifice plate 462. Together, the wire-like support 466 and the spring 470 hold the orifice plate 462 in place in a manner that allows the orifice plate 462 to move up and down against the resilient bias of the wire-like support 466.

The actuator element 472 is preferably annularly shaped and the orifice plate 462 is preferably circular. The orifice plate 462 extends across and is soldered or otherwise affixed to the actuator element 472. Constructions of vibrator-type atomizer assemblies are described, for example, in Helf et al. U.S. Pat. No. 6,293,474, Denen et al. U.S. Pat. No. 6,296,196, Martin et al. U.S. Pat. No. 6,341,732, Tomkins et al. U.S. Pat. No. 6,382,522, Martens, III et al. U.S. Pat. No. 6,450,419, Helf et al. U.S. Pat. No. 6,706,988, and Boticki et al. U.S. Pat. No. 6,843,430, all of which are assigned to the assignee of the present application and which are hereby incorporated by reference herein. Accordingly, the atomizer assembly will not be described in detail except to say that when alternating voltages are applied to the opposite upper and lower sides of the actuator element 472, these voltages produce electrical fields across the actuator element 472 and cause it to expand and contract in radial directions. This expansion and contraction is communicated to the orifice plate 462 causing it to flex such that a center region thereof vibrates up and down. The center region of the orifice plate 462 is domed slightly upwardly to provide stiffness and to enhance atomization. The center region is also formed with a plurality of minute tapered orifices that extend through the orifice plate 462 from the lower or under surface of the orifice plate 462 to its In operation, electrical power, in the form of high frequency alternating voltages, is applied to the opposite upper and lower sides of the actuator element 472, as described above. A suitable circuit for producing these voltages is shown and described in U.S. Pat. No. 6,296,196, noted above. As described in that patent, the device may be operated during successive on and off times. The relative durations of these on and off times can be adjusted by an external switch actuator (not shown) on the outside of the housing and coupled to a switch element on the microprocessor. In other embodiments, the on and off times may be controlled by a preset program, or controlled by a user interface working through a processor, such as a user control.

When the atomizer assembly is supported by the wire-like support 466, the orifice plate 462 is positioned in contact with the upper end of the wick 464. The atomizer assembly is thereby supported above the liquid reservoir 326 such that the upper end of the wick 464 touches the underside of the orifice plate 462. Thus, the wick 464 delivers liquid from within the liquid reservoir 326 by capillary action to the top of the wick 464 and then by surface tension contact to the underside of the orifice plate 462, which, upon vibration, causes the liquid to pass through its orifices and be ejected from its opposite side (i.e., the upper surface) in the form of small droplets.

In one embodiment, a horizontal platform serves as a common structural support for both the reservoir 326 and the atomizer assembly. In this manner, the reservoir 326, and, in particular, the upper end of the wick 464 disposed therein, are aligned with the orifice plate 462. Moreover, because the atomizer assembly and the orifice plate 462 are resiliently mounted, the upper end of the wick 464 will always press against the under surface of the orifice plate 462 and/or the actuator element 472 irrespective of dimensional variations which may occur due to manufacturing tolerances when one reservoir 326 is replaced by another. This is because if the wick 464 contained in the replacement reservoir 326 is higher or lower than the wick 464 of the original liquid reservoir 326, the action of the spring 470 will allow the orifice plate 462 to move up and down according to the location of the wick 464 in the replacement reservoir 326, so that the wick 464 will press against the underside of the orifice plate 462 and/or the actuator element 472. It will be appreciated that the wick 464 preferably is formed of a substantially solid, dimensionally stable material so that it will not become overly deformed when pressed against the underside of the resiliently supported orifice plate 462. The features of the horizontal platform on which the atomizer is disposed will be discussed further below.

As shown in FIGS. 13 and 14, the wick 464 extends from inside the liquid reservoir 326 up through a plug 474 in the top of the reservoir 326 to contact the orifice plate 462 and/or the actuator element 472. (The plug 474 holds the wick 464 within the liquid reservoir 326.) The wick 464 has longitudinally extending capillary passageways that draw liquid up from within the reservoir 326 to the upper end of the wick 464. In lieu of the capillary wick 464, we envision that a capillary member (not shown) may alternatively be used. Such a member generally includes plural capillary passageways on an exterior surface thereof. These passageways act, via capillary action, to transfer fragrance from the liquid reservoir 326 to the orifice plate 462 and/or the actuator element 472.

A more detailed explanation of the atomization device described above may be found in commonly assigned Martens et al. U.S. Publication No. 2004/0200907. In addition, a more detailed explanation of the support structure for the atomizing device may be found in commonly assigned Helf et al. U.S. Pat. No. 6,896,193. The disclosure of the '907 publication and the '913 patent are hereby incorporated by reference.

Of course, other active material emitting devices may be used in addition to the atomizer assembly. Specifically, we envision that evaporation devices, heat-assisted evaporation devices, and fan-assisted evaporation devices, among others, could be used in addition to the piezoelectrically actuated atomization device described above. Moreover, even within each type of dispenser, variations are possible, as would be appreciated by one of ordinary skill in the art.

Power Source

The power source supplies power to light the light source, and if required, to operate the active material dispenser (for example, to supply voltages to the upper and lower surfaces of the actuator plate in the atomization-type active material dispenser discussed above). Also, the power source may be used to power additional components (although not shown, these additional components may include, e.g., a fan). In a preferred embodiment, the power source comprises one or more batteries. When one battery is used, a voltage step-up may be used to ensure sufficient power. The batteries may be replaceable, or they may be rechargeable. If rechargeable batteries are used, they may be removed for recharging, or an adapter may be provided on the device such that the batteries can be charged without being removed from the device. For instance, a receptacle (not shown) may be incorporated into the device to receive a plug that supplies power from, for example, an electrical outlet. It is not required, however, that the power source comprises batteries. For example, power for the device may be derived directly from an electrical outlet. As will be appreciated by one of ordinary skill, however, the use of alternate power sources may require that the device further include an AC to DC converter.

Control Circuitry

As used throughout, the term "control circuitry" is intended to be a representative term that encompasses all controls that can be used to embody the light and active material emitting device. For example, the preferred embodiments are discussed below with reference to microprocessors and/or circuit boards, and microprocessors and circuit boards constitute control circuitry. Further contemplated examples of control circuitry that may be used are an Application Specific Integrated Circuit (ASIC), a microprocessor, and an arrangement of one or more resistors and/or capacitors. Control circuitry may or may not include software. These examples of control circuitry are not limiting, however. Other control circuitry may also be used.

The control circuitry is generally used to control the operation of the device and is powered by the batteries. Specifically, the control circuitry is designed to provide the signals for controlling the operation of the light source. When one or more LED's are provided as the light source, the microprocessor may alter the duty cycles of the LED's to control the perceived intensity of the emitted light, thereby creating the candle-like flicker effect. Alternatively, instead of altering the duty cycles, the microprocessor may otherwise adjust the light emission properties of the LED's. For example, methods utilizing an analog sine wave or a digital potentiometer are generally known in the art. In other embodiments, when at least two LED's are used, as in FIGS. 8A-8C, and one LED 306*b* receives a constant current to emit light constantly, that LED 306*b* can be controlled separately from a circuit board, either to receive a power supply from the power source, when the device is turned on, or to not receive power, when the device is turned off. In other words, when one LED 306*b* constantly emits light, it is not necessary to provide means for adjusting the duty cycle thereof (such as the microprocessor). In this case, the microprocessor may adjust the operation of only the LED's that flicker. In other embodiments the constant emission LED may be controlled by pulse-width modulation set by the microprocessor such that the frequency of the pulse-width is imperceptible to an observer. In this manner, the intensity of the constant emission LED may be varied slightly to add to the overall flicker presentation.

The microprocessor may include circuits for converting power from the batteries to the high-frequency alternating voltages required to expand and to contract the actuator member 472, thereby emitting active material from the active material dispenser 4. In addition, the microprocessor may control a fan and/or a heating element, if such are used. Furthermore, the microprocessor may include controls for automatically turning on and or off one or both of the light source and the active material dispenser.

Support Structure A support structure is provided to support the light source, the active material emitter or atomizer assembly, the power source, and the microprocessor, or some combination thereof. The term "support structure" is intended to encompass any and all of a chassis, a housing, a holder, and a base, as those terms are used in the description below, as well as similar structures used to support or contain the features of device.

Embodiments of the Light and Active Material Emitting Device

Having now generally described the components of the present invention, discussion will now be made of various embodiments of a light and active material emitting device. These embodiments include various novel arrangements of the above-described components, as well as additional features.

The first embodiment is depicted in FIGS. 1-5 and. As seen best in FIGS. 2 and 3 a chassis 102 is provided that comprises a chassis cover 102a, a chassis upper portion 102b, and a chassis lower portion 102c. Disposed on the chassis 102 are two batteries 118, a wick-based atomizer assembly 108, a single LED 106, and two printed circuit boards 114, 116. Each of two microprocessors 110, 112 are disposed on the circuit boards 114, 116. As shown, the chassis cover 102a and the chassis upper portion 102b are joinable to form a cavity therebetween, and the chassis lower portion 102c depends downwardly from a bottom of the chassis upper portion 102b. In this embodiment, the atomizer assembly 108, the LED 106, the microprocessors 110,112, and the printed circuit boards 114, 116 are disposed within the cavity formed between the chassis cover 102a and the chassis upper portion 102b. Electrical contacts 122, which the batteries 118 contact to supply the device 100 with power are disposed on the lower portion 102c of the chassis 102, with batteries 118 disposed in contact with the electrical contacts 122.

In the embodiment of FIGS. 1-5, the batteries 118 are removably securable to the lower portion 102c of the chassis 102. A battery retainer 120 may also be provided to aid in maintaining attachment of the batteries 118 to the chassis 102. When the batteries 118 are to be detached from the chassis 102, the retainer 120 must first be removed. Also in this embodiment, an entryway (not shown) is formed in the bottom of the upper portion 102b of the chassis 102, proximate to the atomizer assembly 108, so that a reservoir 126 containing a liquid to be atomized may be easily removed from, and reattached to, the atomizer assembly 108. Accordingly, this arrangement provides a user with access to the batteries 118 and to the reservoir 126 (for example, to enable changing the batteries 118 and the reservoir 126), but the remaining components are maintained within the cavity formed between the chassis cover 102a and the chassis upper portion 102b, reducing the possibility of contact with, and possible damage to, those components.

Figure 3:
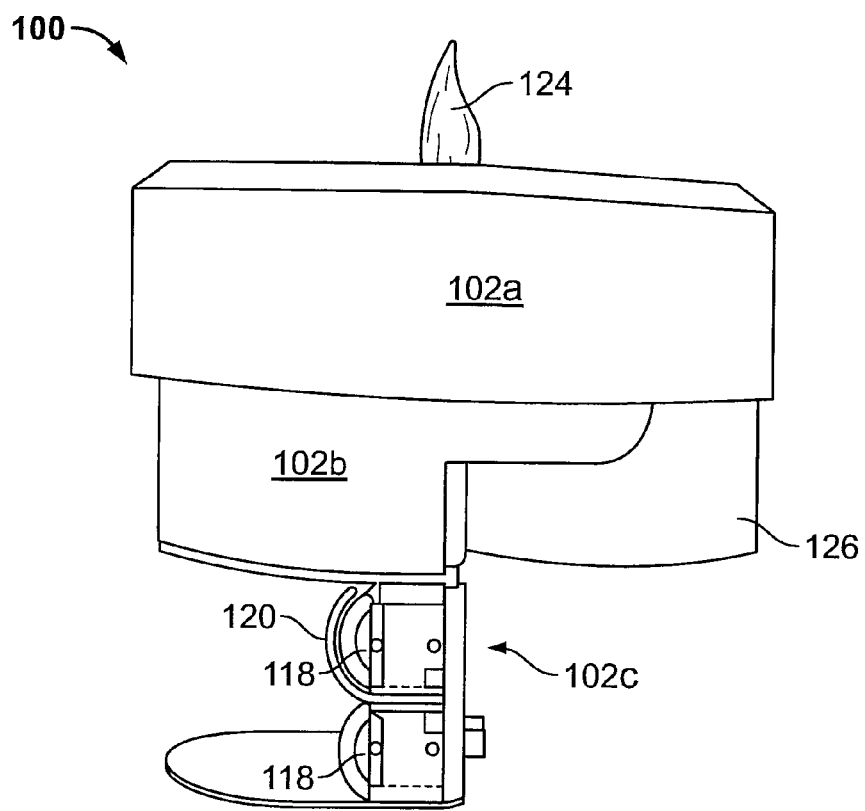
FIG. 3 is a side view of the device of FIG. 1, with the base removed.
Figure 2:
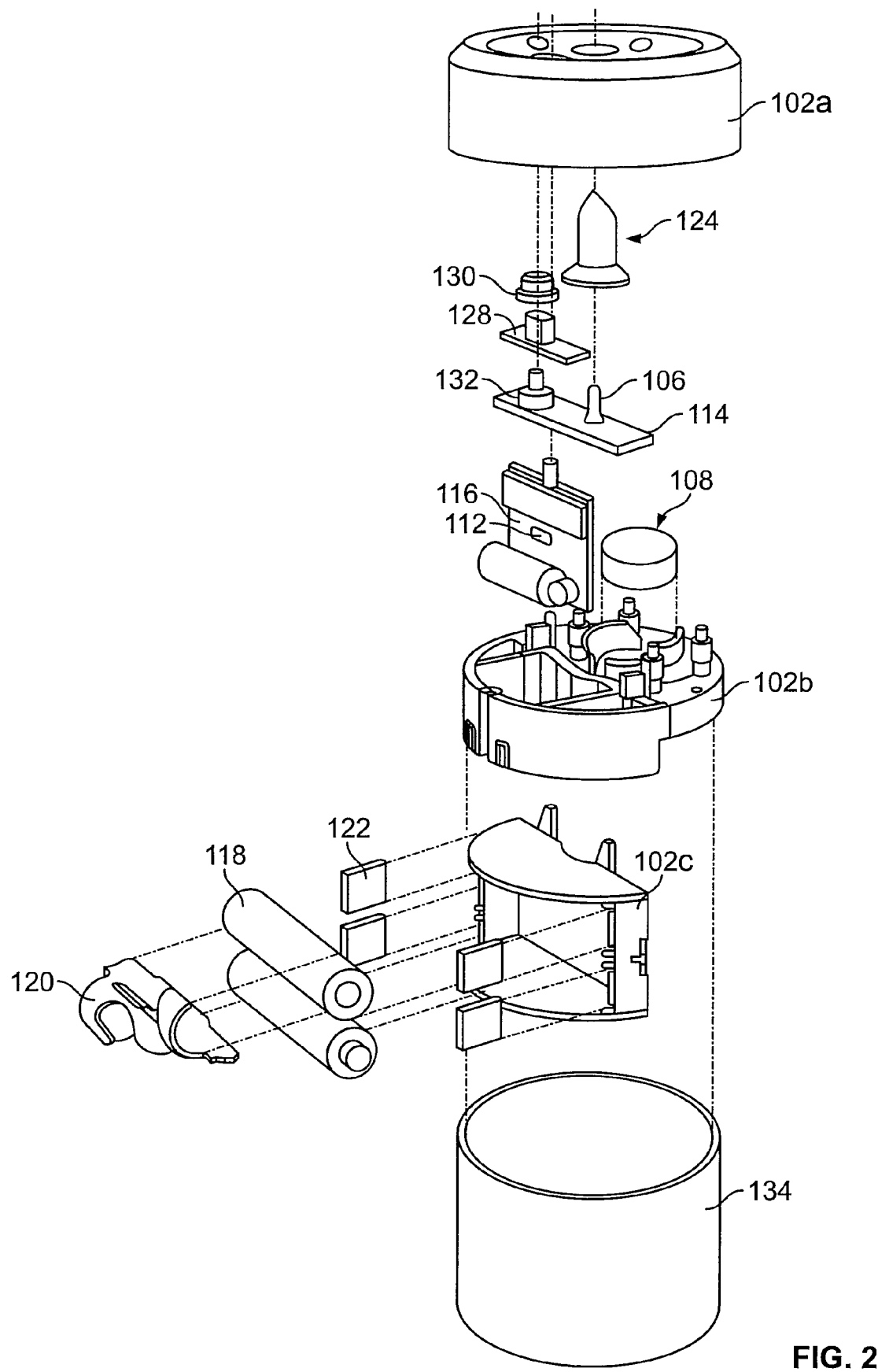
FIG. 2 is an exploded perspective of the device of FIG. 1.

As shown in FIGS. 1 and 3, in the first embodiment, a protrusion, or tip 124 extends axially upwardly the top of the chassis cover 102a. Preferably, the LED 106 is disposed within the tip 124, such that light emitted from the LED 106 is diffused by, and transmitted through, the tip 124. As depicted in FIG. 2, the tip 124 is a separate component of the device 100, disposed within an aperture formed through the top of the chassis 102. The tip 124 may also be formed integrally with the chassis 102. By making the tip 124 a separate piece, however, the tip 124 may be replaceable, e.g., with other, differently constructed, or colored, tips. In the case of a colored tip, the LED 106 may be a white LED in order to transmit light in the color of the colored tip. Also, a separate tip 124 may be formed of a material other than that used for the chassis. For example, the tip 124 may be formed of a material through which light is transmitted, e.g., plastic, glass, wax, and the like. Additionally the tip 124 may be formed of a material such that the tip 124 continues to glow, even after the LED 106 is shut off.

Apertures other than that formed for insertion of the tip 124 may also be formed in the chassis 102a. For example, an emissive aperture 136 is preferably formed through a top surface of the chassis 102, above the atomizer assembly 108, such that the active material emitted by the atomizer passes through the emissive aperture 136, into the ambient environment. Furthermore, apertures may be formed in the chassis 102, through which switches are disposed. For example, an emitter controlling switch cover 128 (that cooperates with a slidable switch (not-shown)), in communication with the microprocessor 112 that controls the timing of the duty cycle applied to the atomizer assembly 108, may be provided to enable a user to manually adjust an amount of active material emitted. In this manner, the user can optimize the emission amount, based on outside considerations, such as room size, and the like. Furthermore, an on/off switch or button 130 may also be provided in an aperture formed through the chassis 102, to turn one or both of the LED 106 and the atomizer 108 on and off. For example, as shown in FIG. 1, an on/off toggle switch 132 that is electrically connected to the LED 108, is disposed in an aperture through the top surface of the chassis 102, thereby enabling a user to turn the LED 108 on and off. Although not shown, a similar toggle switch, a push button, or the like, may also be provided for turning the atomizer assembly 108 on and off. In other embodiments, the chassis 102 may have exposed section, such that apertures need not be formed.

The chassis 102, with attached components, is preferably detachably engageable with a base, or cup 134. The engagement of the chassis 102 with the base 134 forms a unitary housing in which the atomizer assembly 108, reservoir 126, batteries 118, and controls are disposed. The base 134 is generally cylindrical, including a sidewall and a bottom surface and the top of the base is open. The upper portion 102b of the chassis 102 is also generally cylindrical, with an outer diameter substantially the same as that of the base 134. By lowering the chassis 102 into the base 134, the lower portion 102c of the chassis 102 becomes disposed within the base 134, and the upper portion 102b of the chassis 102 is disposed proximate to the open top of the base 134. The unitary housing thus formed has the appearance of a cylinder, with a tip protruding axially upwardly from approximately a central portion of the top of the cylinder.

While one of ordinary skill in the art would understand that there are many ways for removably engaging the chassis with respect to the base, a preferred method of engagement for this embodiment is described as follows. A substantially C-shaped receptacle is formed on the lower portion of the chassis 102 and a protrusion extends axially upwardly from the bottom surface of the base 134. When the chassis 102 is lowered into the base 134, the C-shaped receptacle of the lower portion 102c of the chassis 102 receives therein the protrusion formed in the base 134. In this way, proper alignment of the chassis 102 within the base 134 is achieved. Moreover, as should be understood, because the chassis 102 and the base 134 each has a cylindrical footprint and the protrusion and C-shaped receptacle are positioned on respective axes, the chassis 102 is easily attached to the base 134 regardless of the rotational orientation of the chassis 102 with respect to the base 134.

Preferably, the dimensions of the chassis 102 and base 134 combination are anywhere from between approximately one inch and approximately six inches in diameter and preferably anywhere from between approximately one inch and approximately six inches in height. Of course, the dimensions may be larger or smaller, depending on the desired aesthetic. Also, because as described above at least a portion of the flickering LED 106 is disposed within the tip 124, the tip 124 has the appearance of a conventional candle flame. All or a portion of the rest of the device 100 may also be light transmissive. Light transmissive materials that may be used include glass, plastic, wax, and the like. Furthermore, by moving the LED within the tip, a more realistic perception of a conventional candle may be obtained.

Figure 4:
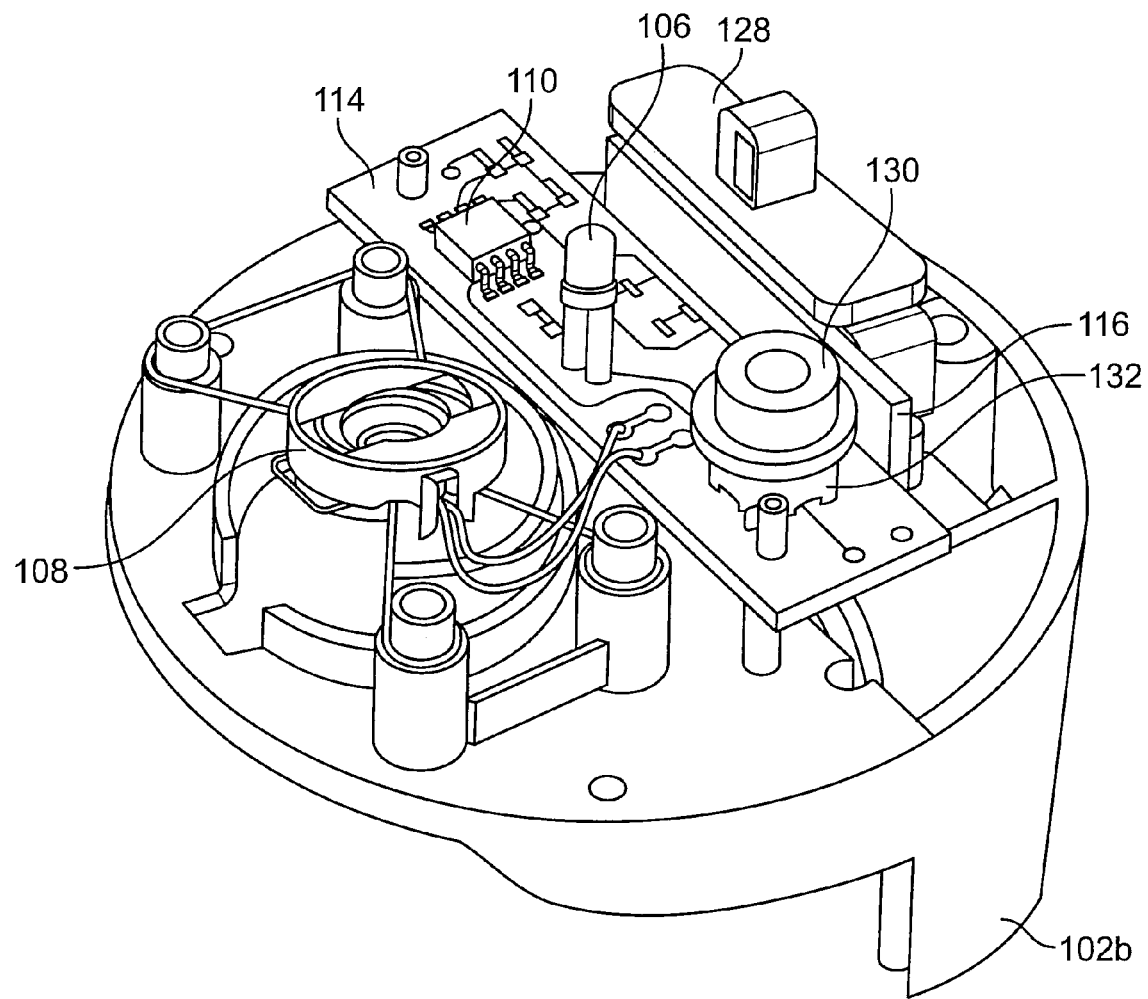
FIG. 4 is a perspective view of components of the device of FIG. 1.

Thus, according to the first embodiment, the combination of the chassis 102 and base 134, as a result of their likeness to a conventional candle, may be provided to a consumer to be used with existing votive holders for conventional candles. Alternatively, the device can be embodied in the combination of chassis 102 and base 134 with holder 104 (as shown in FIG. 4). Furthermore, it should also be understood that the chassis 102 may be designed to stand alone, i.e., without the base. For example, the lower portion 102c of the chassis 102 may be designed to enable the entire chassis 102 to stand on its own.

Figure 6:
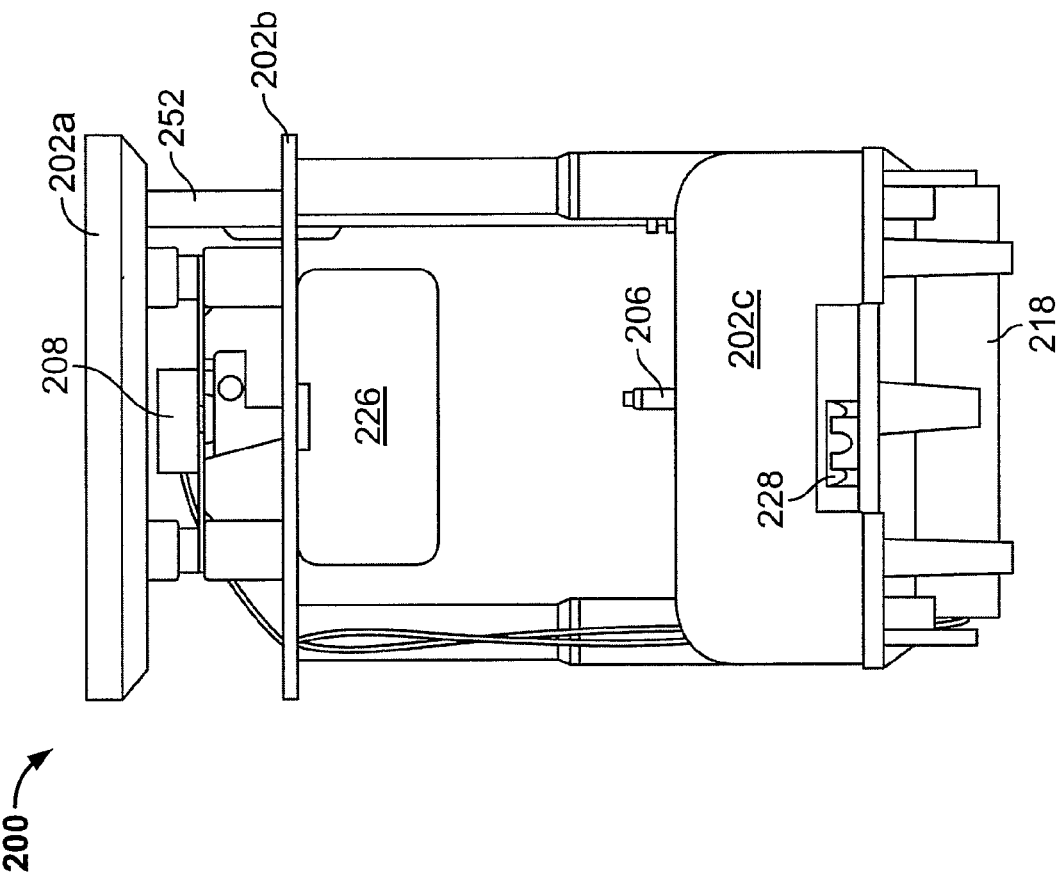
FIG. 6 is a side view of a light and active material emitting device according to a second embodiment.

A second embodiment will now be described with reference to FIGS. 6 and 7. This embodiment includes many of the same components as discussed above with respect to the first embodiment, and descriptions thereof will not be repeated.

According to this second embodiment, a chassis 202 (different from the chassis 102 of the first embodiment) is provided. An atomizer assembly 208, an LED 206, two circuit boards, a microprocessor, and a battery 218 are disposed on the chassis 202. As illustrated, the chassis 202 includes a top 202a, an upper portion 202b, disposed below the top 202a, and a lower portion 202c, disposed below the upper portion 202b. The atomizer assembly 208 is arranged on the upper portion 202b of the chassis 202, and a reservoir 226 containing a fluid to be atomized by the atomizer assembly 208 is removably matable to the atomizer assembly 208. The lower portion 202c of the chassis 202 is disposed sufficiently below the upper portion 202b of the chassis 202 so as to facilitate removal and replacement of the reservoir 226. The lower portion preferably includes an inner cavity in which the controls, i.e., circuit board(s) and microprocessor(s) (not shown), are disposed.

The LED 206 is disposed proximate to a top surface of the lower portion 202c of the chassis 202. More specifically, the LED 206 of this embodiment is disposed on a circuit board disposed within the inner cavity of the lower portion 202c of the chassis 202. An aperture is formed through a top of the lower portion 202c of the chassis 202, and at least a portion of the LED 206 protrudes through the aperture. The battery 218 is disposed below the lower portion of the chassis 202. As would be appreciated by one of skill in the art, electrical leads and the like may be necessary for communication between the battery 218, the controls, the LED 206, and the atomizer assembly 208.

Figure 7:
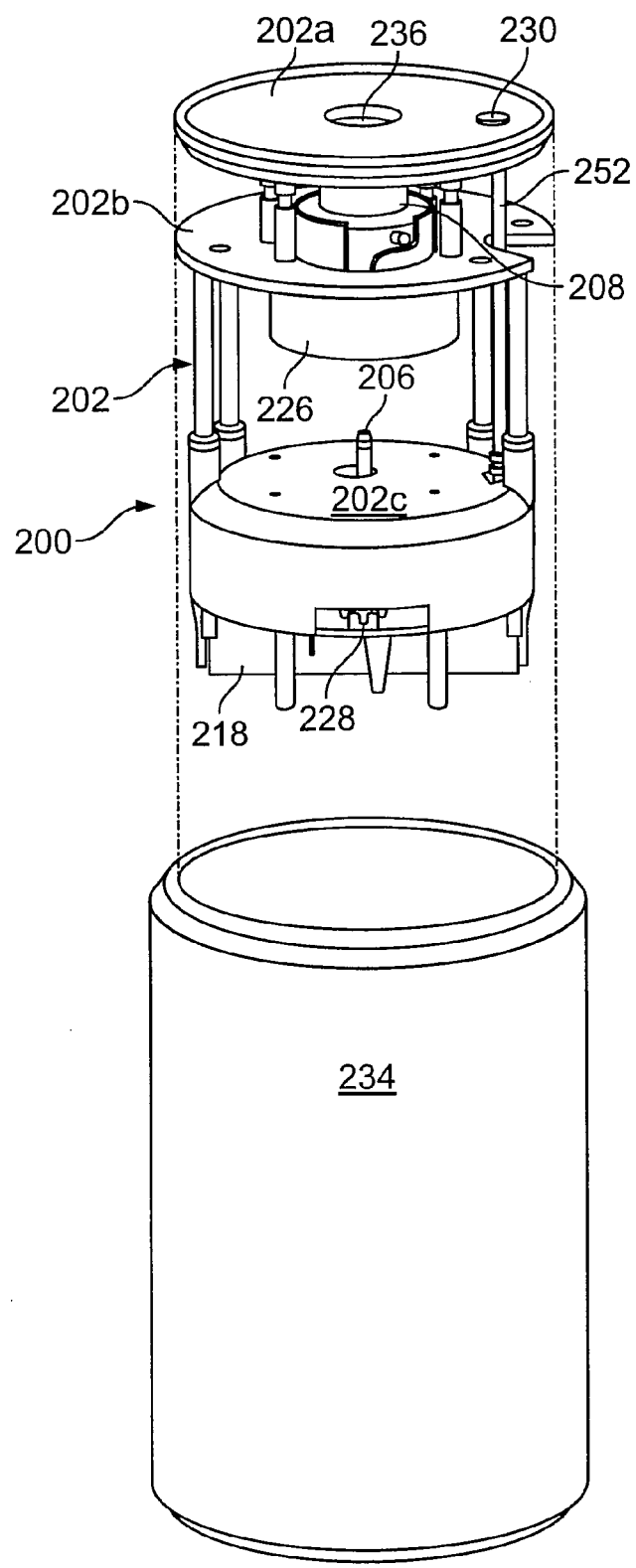
FIG. 7 is an exploded perspective view showing the relationship of the device of FIG. 6 with a base.

As shown in FIG. 7, the chassis 202 is removably placeable within a base 234. The base 234 is generally cylindrical, with a bottom surface (not shown) and an open top. The chassis 202 is received in the base 234 through the open top. The chassis 202 and the base 234, when the chassis 202 is placed in the base 234, form a unitary housing in which the LED 208, an active material emitter 236, the controls, and the battery 218 are disposed. Preferably, the chassis 202 and the base 234 are configured such that the top surface of the chassis 202 is disposed within the open top of the base, and the housing formed by the combination of the chassis 202 and the base 234 resembles a conventional pillar candle.

Similar to the first embodiment, the housing of the second embodiment also preferably includes an emission aperture aligned with the atomizer assembly 208. Specifically, because in this embodiment the atomizer is arranged below the top 202a of the chassis 202, the emission aperture 236 is formed through the top 202a of the chassis 202. In this manner, liquid atomized within the housing may be released into the ambient environment.

Again, similar to the first embodiment, means are also provided for adjusting the amount of active material emitted by the emitter 208 and for turning the LED 206 on and off. As shown in FIGS. 6 and 7, a slidable switch 228, in communication with the microprocessor that controls the atomizer assembly 208, is disposed on the lower portion 202c of the chassis 202. The slidable switch 228 is manually adjustable between multiple positions to regulate the frequency at which the atomizer assembly 208 emits the substance contained in the reservoir 226. In addition, a push button 230 is disposed on the top 202a of the chassis 202 for turning the LED 206 on an off.

As will be appreciated from the FIGS., because the controls, i.e., the circuit boards and microprocessor, associated with the atomizer assembly 208 and the LED 206 are disposed within the lower portion 202c of the chassis 202, and the atomizer assembly 208 and the push button 230 are disposed proximate to the top 202a of the chassis 202, electrical wires are provided to convey controls from the lower portion 202c of the chassis 202 to the atomizer 280, and a post 252 is provided for transmitting the actuation of the push button 230 disposed on the top 202a of the chassis 202 to a switch on the circuit board that turns the LED 206 on and off. In a similar regard, as it may also be beneficial to have the slider switch 228 for adjusting emission of the fluid contained in the reservoir 226 disposed on the top of the housing (for example, for ease of access for the user), it may also be necessary to provide a mechanical, an electrical, and/or an electro-mechanical means for connecting the slider switch and the appropriate controls.

According to this second embodiment, a light and substance emitting device 200 is provided. Preferably, as mentioned above, the housing (i.e., the combined chassis 202 and base 234) of the device 200 is configured and sized to resemble a conventional pillar candle. As should be understood, since the LED 206 emitting the flickering light is disposed within the housing, much of the light will be transmitted through the sidewall of the base 234. Accordingly, at least a portion of the base 234 should be light transmissive. In addition, at least a portion of the chassis 202 may also be light transmissive. To these ends, all or a portion of the chassis 202 and/or the base 234 may be formed of one or more of glass, plastic, wax, and the like.

Variations of this second embodiment are also contemplated. For example, while the holder 234 is generally cylindrical, such is not required. Rectangular, square, and a myriad of other shapes and sizes are contemplated. In addition, while the chassis 202 is inserted through a top of the base 234, such is not required. For example, the base may be open at the bottom, such that the base is slid over the chassis 202, or the base 234 and chassis 202 may be integrally formed, with access panels for replacing the reservoir 226, battery 218, and the like.

A third embodiment will now be described with reference to FIGS. 8A-8C, 9, and 10. In this embodiment a light and active material emitting device 300 includes a chassis 302 comprising a chassis cover 302a and a chassis base 302b which together form a cavity that encases each of two LED's 306a, 306b, an active material emitter 308, two batteries 318, and a printed circuit board with microprocessor 310. The LED's 306a, 306b are connected either directly or indirectly to both of the batteries 318 and the microprocessor 310. In this embodiment, the LED's 306a, 306b are preferably located substantially centrally with respect to a top surface of the device, and above the active material emitter 308, the batteries 318, and the microprocessor 310, i.e., on a side of the active material emitter 308, the batteries 318, and the microprocessor 310 opposite to the chassis base 302b. At least a portion of the LED's 306a, 306b are preferably located above a top surface of the chassis cover 302a. By placing the LED's 306a, 306b above the other components in this manner, the emission of light is not impeded by these components, so shadows are substantially prevented, and a more realistic-looking flame is created.

Figure 8:
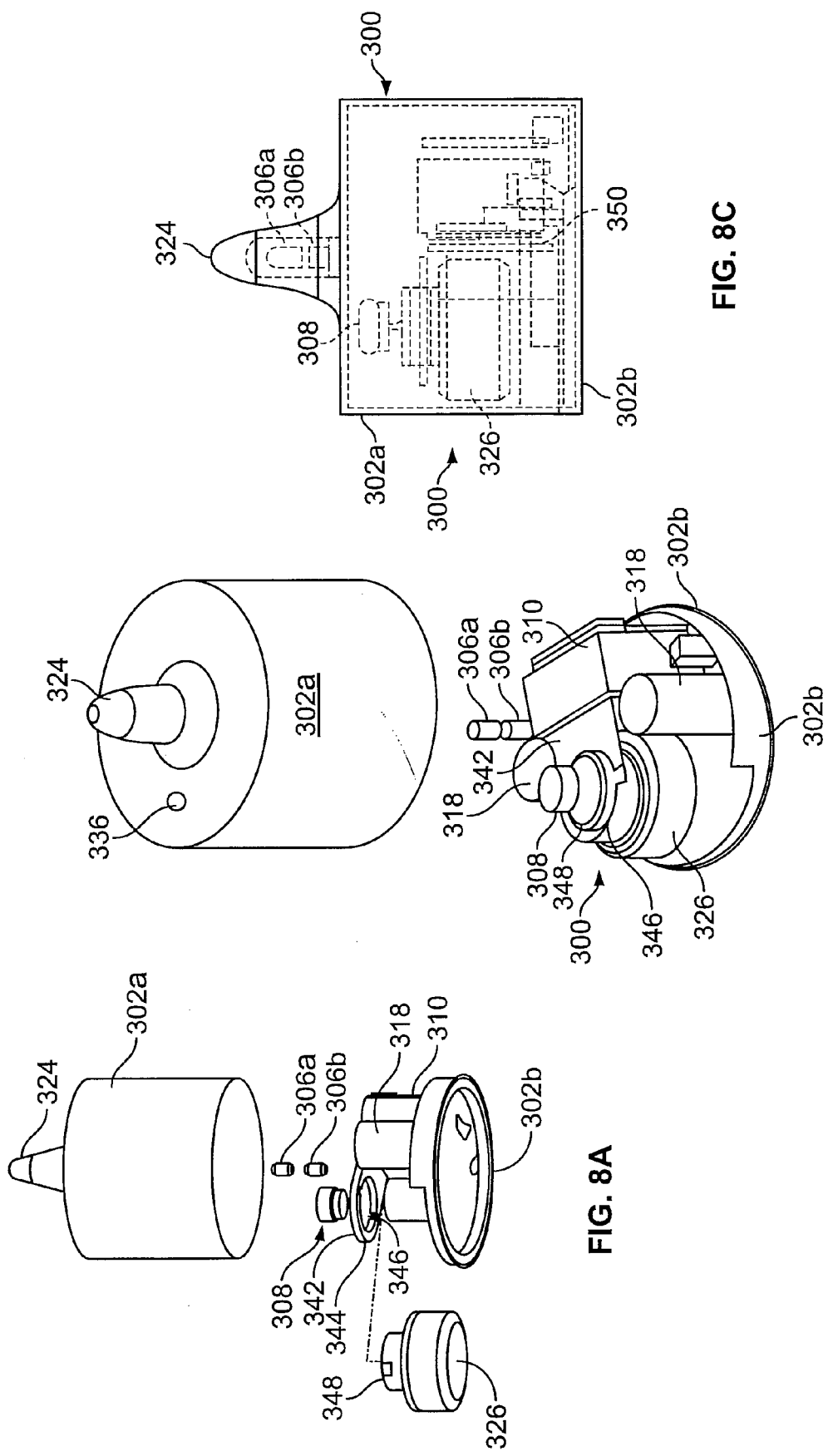
FIGS. 8A-8C are views of a light and active material emitting device according to a third embodiment.

The chassis 302 of the embodiments of FIGS. 8A-8C preferably includes a horizontal platform 342 (preferably disposed on the chassis base 302b) for aligning the active material emitter 308 within the chassis 302. The platform 342 preferably has a platform aperture 344 therethrough with one or more cutouts 346 formed on a periphery of the platform aperture 344. Preferably, the replaceable reservoir 326 comprises one or more nubs 348 (one corresponding to each of the cutouts 346 formed in the platform 342) formed on the reservoir 326. To insert a reservoir 326, a portion of the reservoir 326 is passed through the platform aperture 344 of the platform 342, with the nubs 348 passing through the cutouts 346. Once the nubs 348 clear the cutouts 346, the reservoir 326 is rotated such that the nubs 348 rest on the upper surface of the platform 342. Also, as discussed above, attached to the top of the platform 342 is the wire like-support 466 (not shown in FIGS. 8A-8C) that supports the atomizer assembly 308.

Further, inner surfaces of the chassis 302 may contain various protrusions. These protrusions are preferably provided to aid in properly aligning various components within the chassis 302 and/or to protect components within the chassis 302. For example, a vertical protrusion 350 (shown in FIG. 8C) partitions an area for containing the fragrance emitter 308 from an area having the microprocessor 310. In this fashion, the microprocessor 310 is not accessible when the reservoir 326 is replaced, and, accordingly, inadvertent damage to, or accidental contamination of, the microprocessor 310 is averted.

The chassis cover 302a is designed such that it can be placed on the chassis base 302b, thus forming a unitary device 300. A protrusion or tip 324 is preferably disposed approximately centrally on the chassis cover 302a. The tip 324 extends generally axially, in a direction away from the chassis base 302b and forms a cavity in which the LED's 306a, 306b are disposed when the chassis cover 302a is placed on the chassis base 302b. (As discussed above, the LED's 306a, 306b are preferably arranged one on top of the other.) The tip 324 is substantially conical in shape and is preferably made of a material that diffuses the light emitted by the LED's 306a, 306b. However, it may be desirable to alter the shape of the protrusion, when, for example, more than two LED's are used, or the housing is relatively wide. For instance, the tip 324 may be more dome-shaped when a wider tip 324 is used with a wide device 300 (so as to keep the tip 324 relatively close to the chassis 302).

The tip 324 is preferably between approximately one-eighth of one inch and approximately three inches high and between approximately one-eighth of one inch and approximately three inches wide. The remainder of the device 300 is preferably between about two inches and about ten inches high and preferably between about one and one-half inches and about six inches wide. Thus configured, the device 300 can substantially take on the size and shape of various conventional candles, while the tip 324, by encapsulating the LED's 306a, 306b, simulates a flame.

The chassis cover 302a also includes an emission aperture 336 therethrough. When the chassis cover 302a is placed on the chassis base 302b, the emission aperture 336 aligns with the active material emitter 308. In particular, the emission aperture 336 is formed such that an active material dispensed by the active material emitter 308 passes through the chassis cover 302a to the ambient air, i.e., the chassis cover 302a does not impede the dissemination of the active material from the active material emitter 308.

The chassis cover 302a is preferably secured to the chassis base 302b, although such is not required. For example, as shown in FIG. 8A, the chassis cover 302a may be removably attached to the chassis base 302b such that access to, for example, the reservoir 326 and/or the batteries 318, may be gained for replacement purposes. When the chassis cover 302a is removably attachable to the chassis base 302b, a locking mechanism may be employed. For example, attractive magnets may be situated on the chassis cover 302a and the chassis base 302b, or the chassis cover 302a may include a feature that is designed for compatibility with a mating feature of the chassis base 302b. In this manner, only specific covers and bases can be used.

In another aspect, we contemplate that the chassis base 302b and the chassis cover 302a, when secured together to form the unitary device 300, may be relatively movable. Specifically, when the chassis cover 302a is cylindrical, it may be rotatable on the chassis base 302b. For example, the rotation of the chassis cover 302a may turn on and off the LED's 306a, 306b and/or the active material emitter 308.

As an alternative to the removable chassis cover 302a, when, for example, a new active material is desired or the reservoir 326 is empty, the device 300 may include a hatchway for purposes of replacing the reservoir 326. Examples of two contemplated hatchways 338a, 338b are illustrated in FIGS. 9 and 10, respectively.

Figure 9:
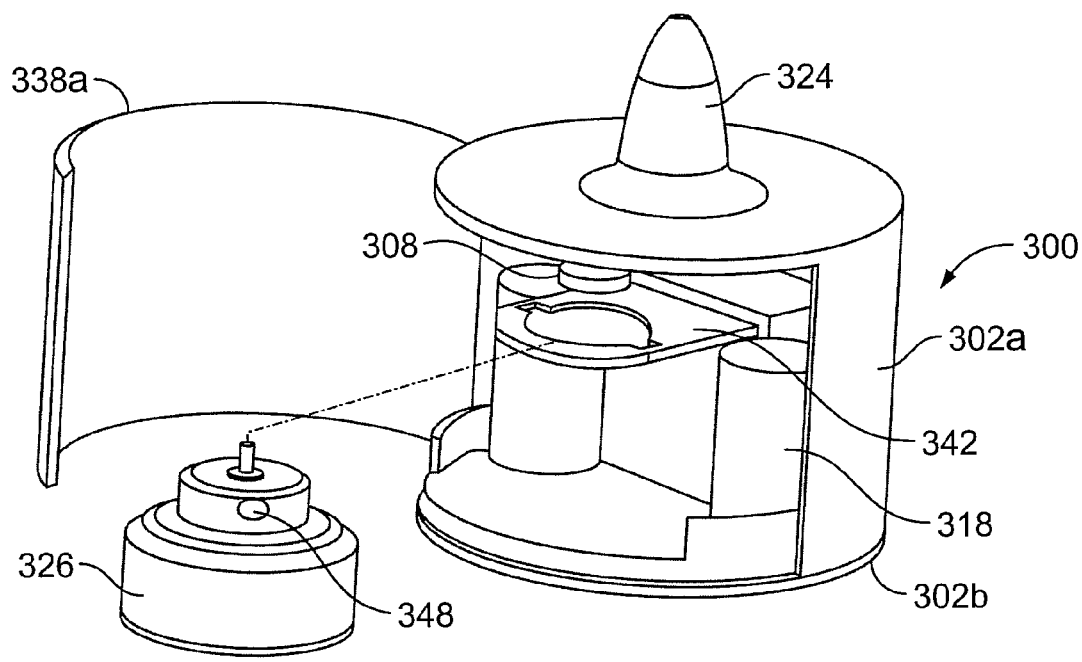
FIG. 9 is a perspective view of a light and active material device according to another embodiment.
Figure 10:
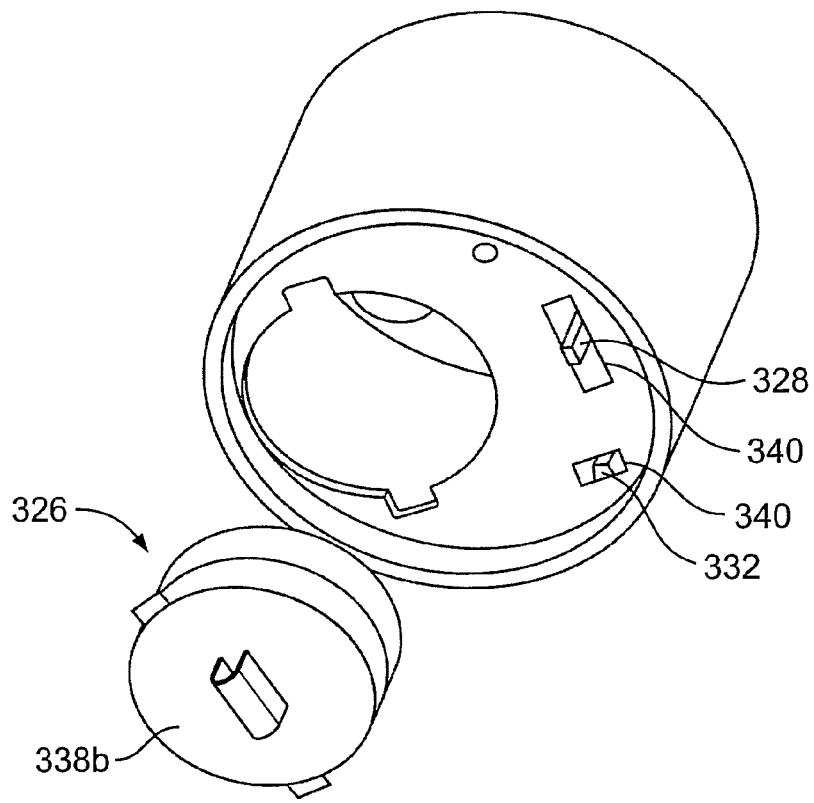
FIG. 10 is a perspective view of a light and active material emitting device according to still another embodiment.
Figure 11:
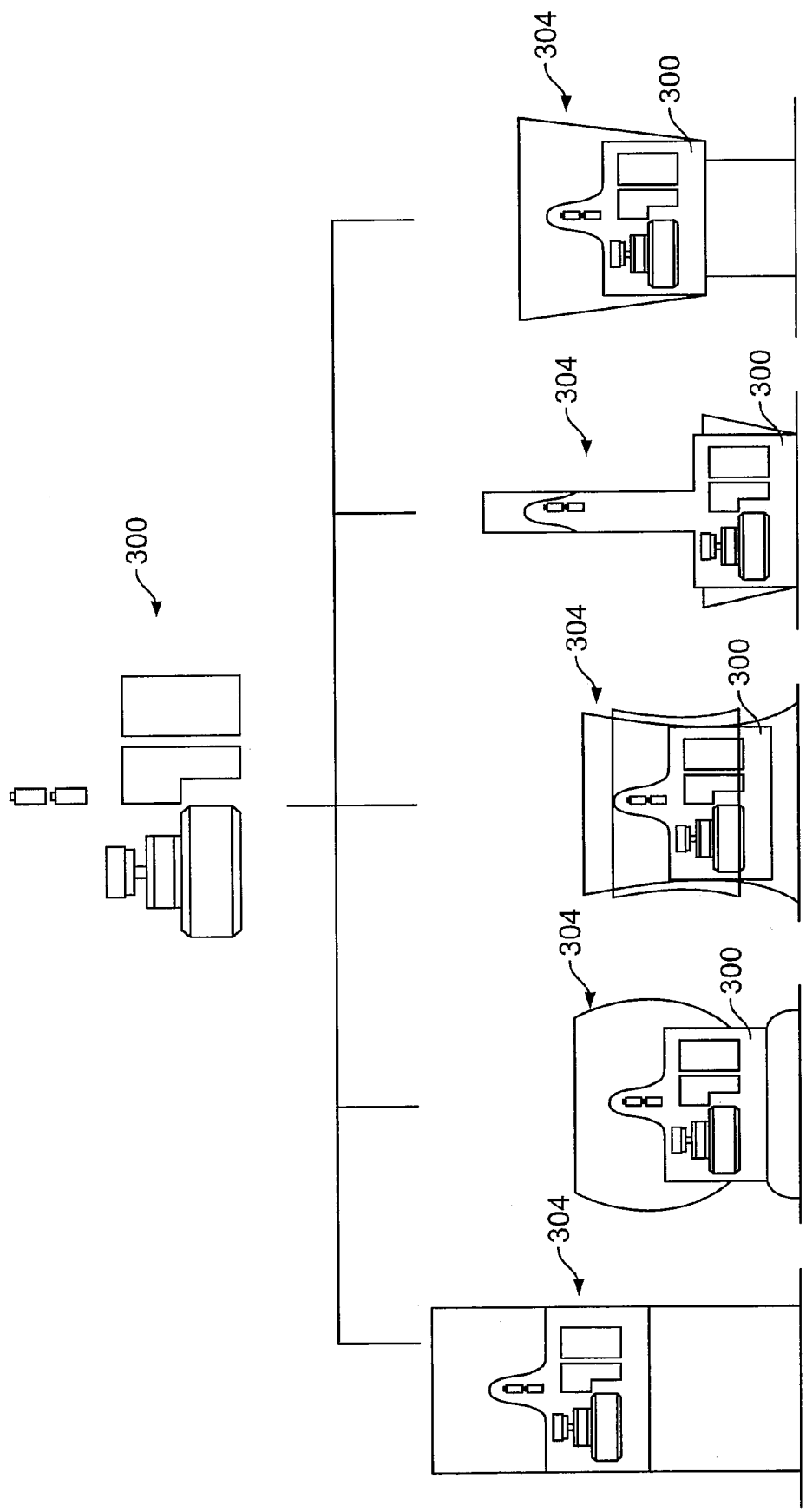
FIG. 11 illustrates further embodiments of a light and active material emitting device.

As shown in FIG. 9, the hatchway 338a may be located on the side of the device 300. The hatchway 338a is preferably hinged and is not completely removable from the device 300. As shown, the hatchway 338a may be opened to gain access to the reservoir 326.

Alternatively, the hatchway 338b may be formed on the bottom of the device 300. For example, as shown in FIG. 10, a substantially circular hatchway 338b is removable from the device 300. In this configuration, the reservoir 326 is preferably coupled to the hatchway 338b. By coupling the reservoir 326 thereto, the hatchway 338b supports the reservoir 326, and, when assembled, ensures appropriate positioning of the wick 464 with respect to the atomizer assembly 308. Specifically, when the hatchway 338b is removed, the wick 464 of the reservoir 326 is removed from contact with the atomizer assembly 308. The reservoir 326 is then removed from the hatchway 338b, a new reservoir 326 is coupled to the hatchway 338b, and the hatchway 338b is reattached, with the reservoir 326 properly aligning with the atomizer assembly 308. When the hatchway 338b of FIG. 10 is used, it may be unnecessary for the horizontal platform 342 to support and to align the reservoir 326, as the hatchway 338b will perform these functions. As such, the horizontal platform 342 will support the atomizer assembly 308, either directly, or preferably, with the wire-like support 466 discussed above.

The chassis base 302b may also include one or more apertures 340 through which user control switches pass. A toggle switch 332, for example, allows a user to turn on and off one or more of the active material emitter 308 and the LED's 306a, 306b, and a slider switch 328 allows a user to adjust the rate at which active material is emitted from the active material emitter 308. Alternatively or additionally, switches may also be provided that allow a user to adjust the light emission properties of the LED's 306a, 306b, or to change an emitted light show.

Thus, the third embodiment provides a still further light and active material emitting device 300. As with first and second embodiments described above, the device 300 may be configured to mimic the size and shape of a conventional candle.

As should thus be apparent, in each of the embodiments, a unitary housing comprises a device that emits both a flickering light and an active material, such as a fragrance, to the ambient air. As discussed above, the device is preferably inserted into a holder. Much like typical replaceable votive candles would be placed into decorative holders, unique holders are also provided for use with the lighting and active material devices disclosed herein.

Figure 5:
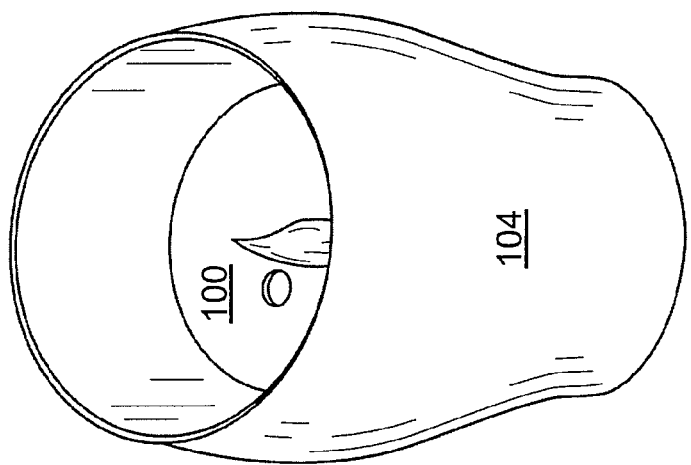
FIG. 5 is a perspective view of the device of FIG. 1 disposed in a holder.

FIG. 5 shows the device 100 of the first embodiment in a holder 104. Specifically, the holder 104 has a globe-like shape, with a bottom, and an open top, similar to a conventional holder for a votive candle. The unitary housing comprising the combination of the chassis 102 and the base 134 is placed inside the holder 104, through the open top of the holder 104. Preferably, at least a portion of the holder 104 allows light to be emitted therethrough. FIGS. 11 and 12A-12D show some representative alternative holder 304 configurations into which a light and active material emitting device 300 can be placed. These examples are by no means limiting.

When an active material emitter is used, the emitted active material should also be emitted from the holder, and it is thus preferred that the holder provide ample ventilation. In particular, the light and active material emitting device is preferably arranged in the holder such that the emission aperture through which the active material is dispensed is between about one inch and about six inches from the top of the holder and substantially away from the inner surface of the holder. With such an arrangement, buildup of active material on the inside of the holder is minimized. Moreover, the holder may be designed to aid the flow of the active material to the ambient environment. By tapering the holder such that the width of the holder narrows nearer the top of the holder, airflow will increase as it leaves the holder. Furthermore, it is preferred that the holder not impede the emission of light from the LED's in such an embodiment. Specifically, the unitary housing is preferably arranged in the holder such that the tip (as used in the first and third embodiments, discussed above) is between about one-half of one inch and about two inches from the holder, and preferably closer than one inch. The holder may also act as a diffuser. Furthermore, we envision that the holder could further include, for example, a fan for aiding in further dispersion of the active material emitted from the active material emitter. Optionally, a heater or other similar device may aid in dispersing the active material. Still further, convection may be used to disperse the active material, whereby an ambient temperature within the device is increased to a high enough level to aid in dispersing the active material.

The holder may comprise a single piece into which the housing is placed. Alternatively, as shown in FIGS. 12A-12D, a holder 304 may also comprise a holder base 304a and a holder cover 304b. More specifically, the device is contained within, or alternatively comprises, the holder base 304a that receives and supports the holder cover 304b. The holder cover 304b, when supported by the holder base 304a, covers the tip 324. That is, light emitted from the housing by the respective illumination devices also passes through the holder cover 304b. Alternatively, the housing, e.g., the top 324, may not diffuse emitted light, and only the holder cover 304b diffuses emitted light.

Figure 12A:
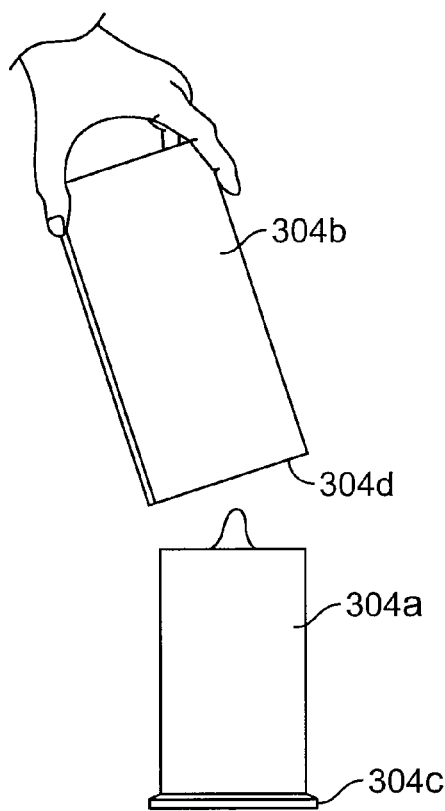
FIGS. 12A-12D illustrate configurations of holders to be used according to various other embodiments of FIG. 13 is a cross-sectional view illustrating an active material dispenser.
Figure 12B:
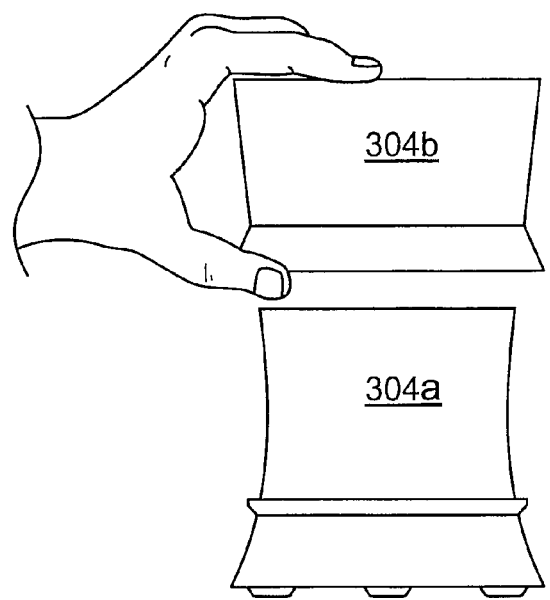
Figure 12C:
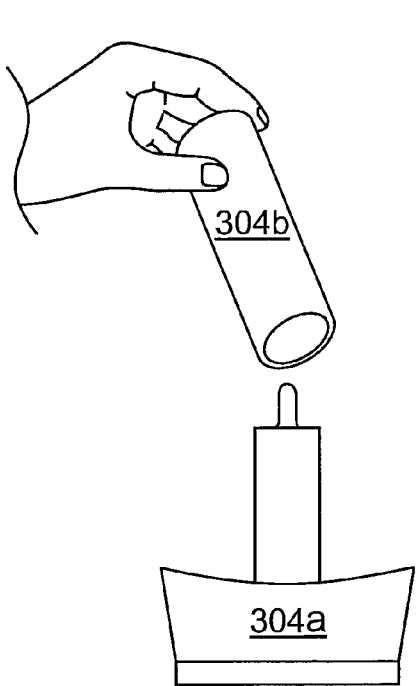
Figure 12D:
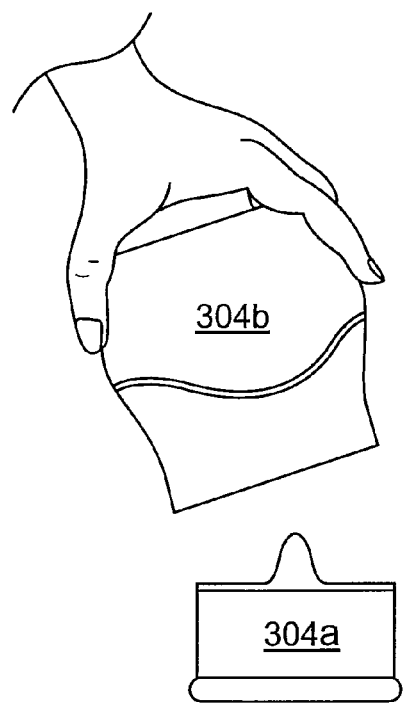

As a specific example of this embodiment, as shown in FIG. 12A, a holder base 304a containing a unitary device as described above has a circumferential lip 304c extending radially outwardly from the holder base 304a. At least a lower portion 304d of the holder cover 304b is sized so as to engage the lip 304c of the holder base 304a, thereby resting the holder cover 304b on the holder base 304a. Other illustrative examples of holders 304 are shown in FIGS. 12B-12D.

While we envision that the holder cover 304b may rest on the holder base 304a, it is preferable that the holder cover 304b detachably attach to the holder base 304a. For example, the holder cover 304b may be designed to snap onto the holder base 304a. Alternatively, the holder cover 304b and the holder base 304a may be designed such that the holder cover 304b is rotated onto the holder base 304a, forming a locking engagement. In this or any configuration, the holder cover 304b may be relatively movable when secured to the holder base 304a. Specifically, when the holder cover 304b is generally cylindrical, it may be rotatable on the holder base 304a to turn the LED's 306a, 306b and/or the active material emitter 308 on and off. Additionally, the engagement and disengagement of the holder cover 304b and the holder base 304a may act to turn the light source and/or active material emitter on and off. In this manner, the device would only operate with the holder cover 304b attached. Moreover, the holder cover 304b and holder base 304a may be specially designed such that only certain covers 304b can be used with the holder base 304a. For instance, the holder base 304a may include a reader (not shown) that reads an ID (e.g., an RF tag) of the holder cover 304b. In this manner, the device will not work unless the holder cover 304b has an appropriate ID.

When using the holder 304 according to this embodiment, we also envision that the holder cover 304b could emit an active material therefrom. For example, impregnable materials such as polyolefins are known that may be impregnated or infused with an active material, such as a fragrance. By forming the holder cover 304b of such a material, the holder cover 304b will emit an active material over time in addition to that emitted by the active material emitter 308. Alternatively, the device of this embodiment could not include the active material emitter 308, in which case, only the holder cover 304b will emit an active material. Also, with respect to the second embodiment described above, we note that the combination of chassis and base resembles a decorative candle, in which case a holder may not be desired. In such a case the base or chassis may be impregnated with an active material.

Because the holder cover 304b of this embodiment is removable, access to the device is facilitated (for example, to turn the LED's 306a, 306b, on or off) and the holder cover 304b can be easily replaced. For example, when the active material, such as a fragrance, impregnated in the holder cover 304b is completely disseminated, a fresh, new holder cover 304b can easily be purchased and attached. Also, a user that has recently redecorated, or that wants to move the device to another room, may purchase a holder cover 304b having a certain color or other aesthetic feature. Moreover, replacement holder covers 304b may provide different smells. In other embodiments, the entire holder (or base) may be replaced.

Figure 15A:
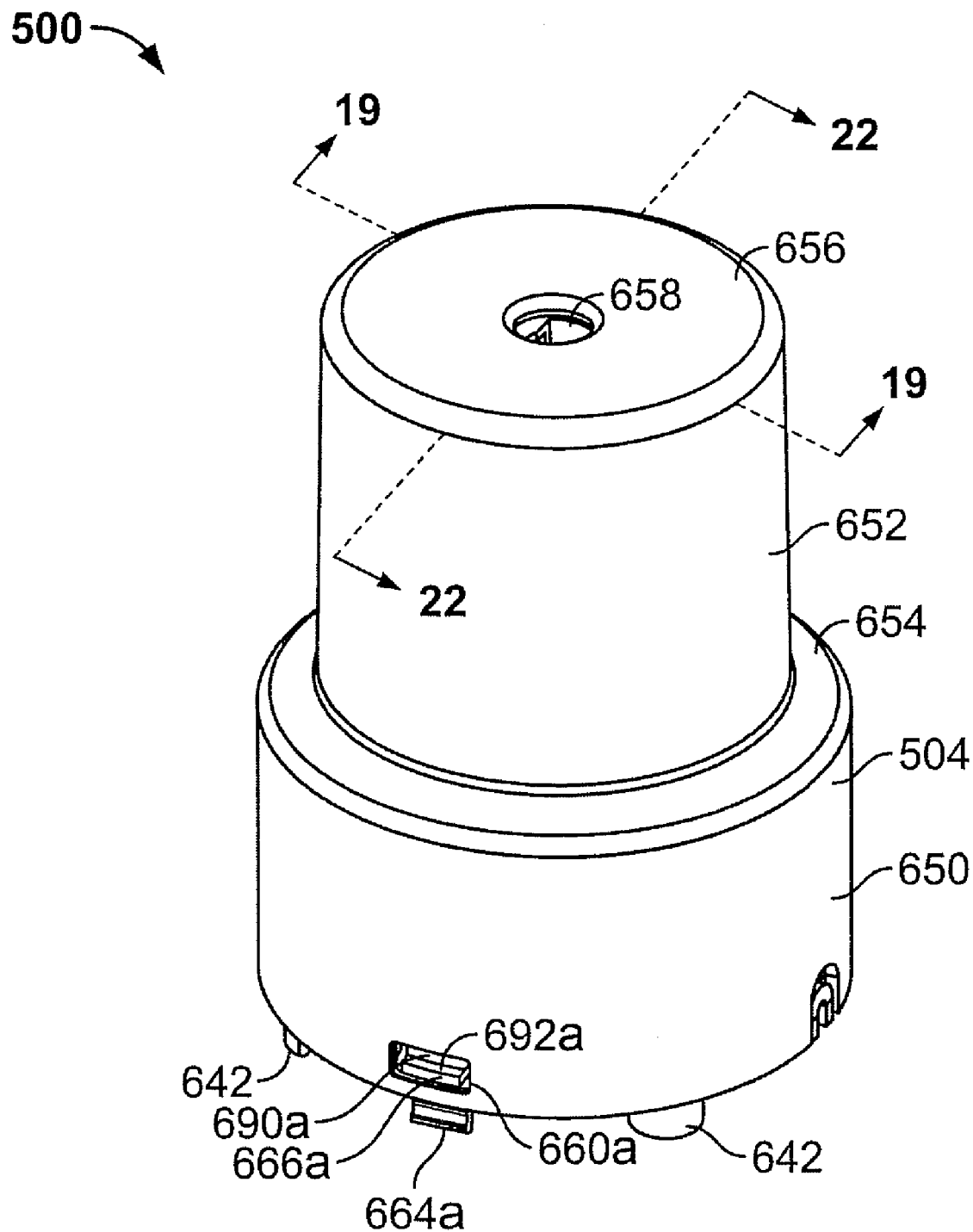
FIG. 15A is a top isometric view of a further embodiment of a light and active material emitting device.
Figure 17:
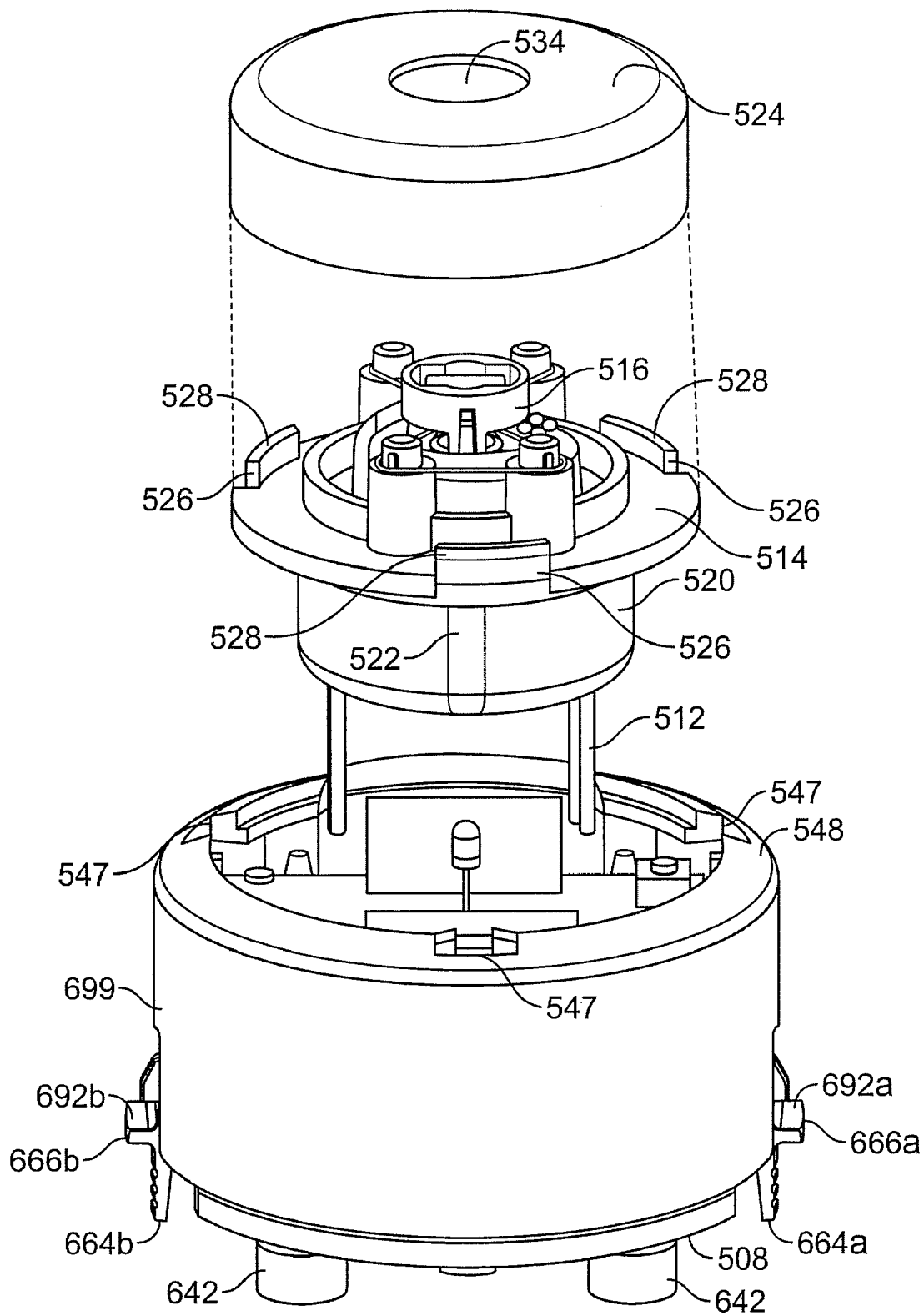
FIG. 17 is an exploded view of the device of FIG. 15A with a cover portion and a housing cover removed therefrom.

A further embodiment of a light and active material emitting device 500 is illustrated in FIGS. 15A-22. Referring to FIGS. 15A, 15B, and 17, the device 500 generally includes a cover portion 504 and a base portion 506. The base portion 506 generally includes a base 508 and a housing 510 disposed on the base 508 for enclosing control circuitry (described hereinafter) for the device 500. A column 512 extends upwardly from the housing 510 and is preferably integral with the housing 510. Further, an arm portion 514 extends perpendicularly from the column 512 and is integral with the column 512. The arm portion 514 includes an active material dispenser in the form of an atomizer assembly 516 that extends through a center portion 518 thereof. The atomizer assembly 516 is described in greater detail with respect to FIGS. 13 and 14.

Any of the atomizer assemblies described in any of the patents incorporated by reference herein may be utilized as the atomizer assembly 516 (or as any of the atomizer assemblies described herein). In general, these assemblies apply an alternating voltage to a piezoelectric element to cause the element to expand and contract. The piezoelectric element is coupled to a perforated orifice plate 519, which in turn is in surface tension contact with a liquid source. The expansion and contraction of the piezoelectric element causes the orifice plate to vibrate up and down whereupon liquid is driven through the perforations in the orifice plate and is then emitted upwardly in the form of aerosolized particles.

Preferably, a container 520 having an active material therein, preferably a liquid fragrance, is inserted into the active material dispenser adjacent the atomizer assembly 516 for emission of the active material therefrom. The container 520 is preferably inserted adjacent the atomizer assembly 516 as discussed in detail with respect to FIGS. 8A-8C. The container 520 includes a wick 522 in communication with the active material therein and extending through a top portion thereof, wherein the wick 520 transports active material from the container 520 to the atomizer assembly 516.

Figure 19:
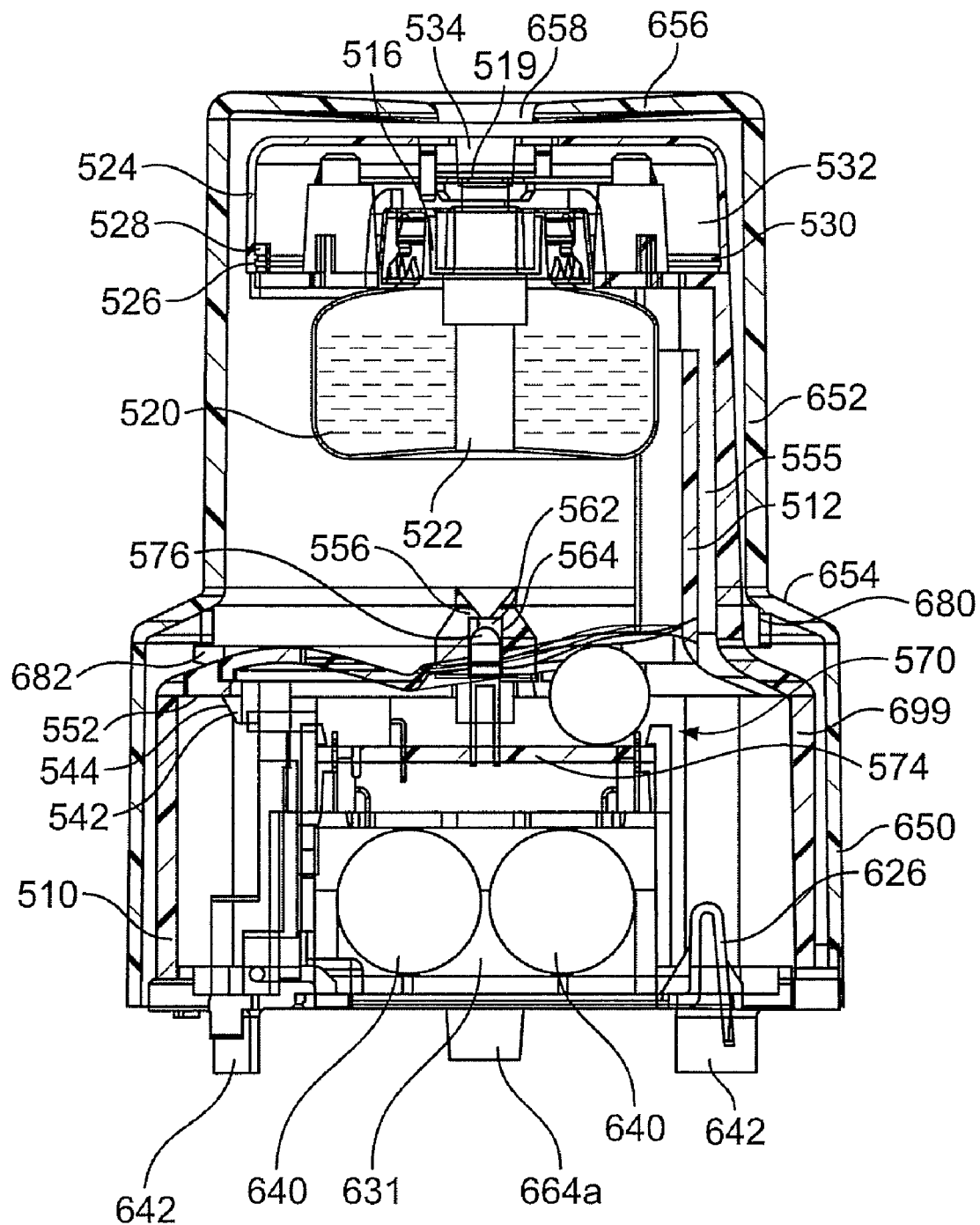
FIG. 19 is a cross-sectional view taken generally along the lines 19-19 of FIG. 15A.
Figure 20:
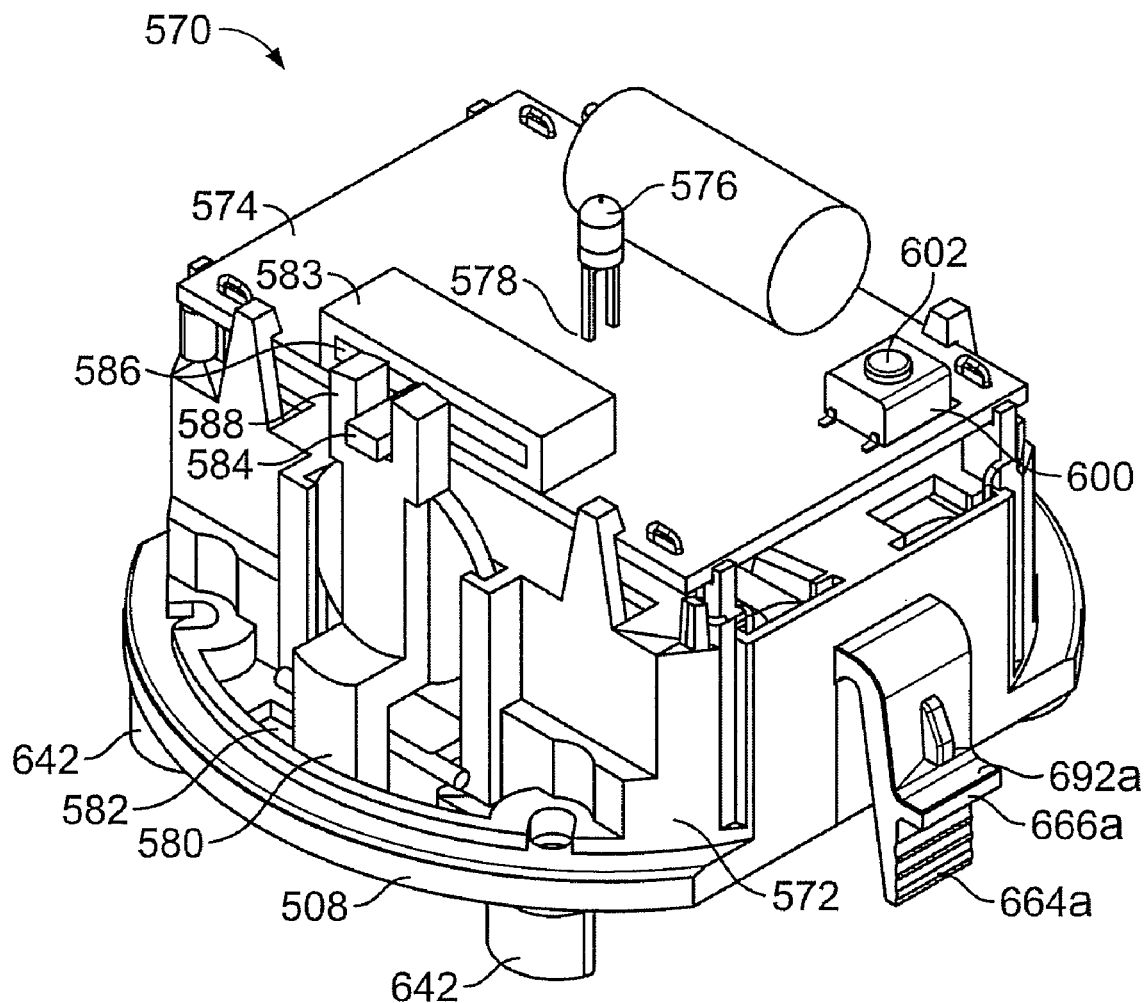
FIG. 20 is a top isometric view illustrating electronics of the device of FIG. 15A.
Figure 21:
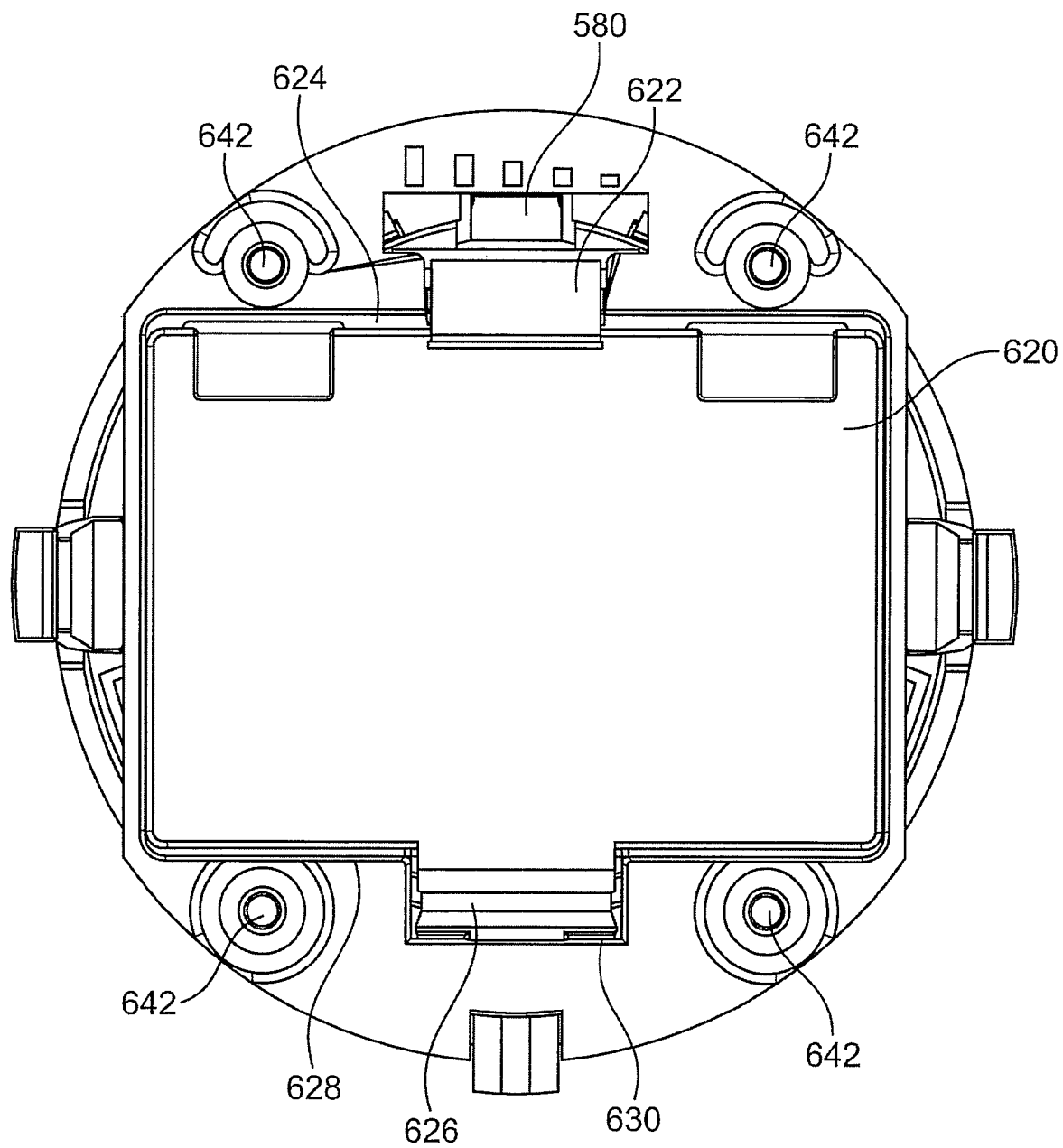
FIG. 21 is a is a bottom plan view illustrating the device of FIG. 15A.

A cap 524 may disposed over the atomizer assembly 516 to hide the components of the atomizer assembly 516. Preferably, as seen in FIGS. 17 and 19, the arm portion 514 includes a plurality of upwardly extending projections 526 extending therefrom, wherein outwardly extending projections 528 extend from the upwardly extending projections 526. The outwardly extending projections 528 are adapted to engage an annular lip 530 extending from an inner periphery 532 of the cap 524 to secure the cap 524 over the atomizer assembly 516. The cap 524 further includes a central circular aperture 534 therein such that active material emitted from the atomizer assembly 516 is directed through the aperture 534.

Referring to FIGS. 16-18, the base portion 506 further includes a housing cover 540 disposed atop the housing 510. As seen in FIG. 18, the housing cover 540 includes a plurality of downwardly extending projections 542, wherein an outwardly extending projection 544 extends from a bottom portion 546 of each downwardly extending projection 542. The housing 510 includes a plurality of cutout portions 547 in a top portion 548 thereof, wherein the downwardly extending projections 542 extend into the cutout portions 546 such that top portions 550 of the outwardly extending projections 544 engage an inner upper surface 552 (FIG. 19) of the housing 510 to retain the housing cover 540 on the housing 510.

As best seen in FIG. 18, the housing cover 540 further includes an upwardly extending column 554 that interfits with the column 512 extending from the housing 510 when the housing cover 540 is disposed on the housing 510 to form a channel 555. Preferably, wires extending from the electrical components of the control circuitry to the atomizer assembly 516 are disposed in the channel 555 to hide and protect the wires. Also preferably, the columns 512, 554 are formed of a transparent or translucent material, preferably a clarified material, such as clarified propylene, so that the columns 512, 554 allow light to pass therethrough. Still further, the housing cover 540 includes a light control device 556, such as a light diffuser, light pipe, lens, or the like, in a center portion 560 thereof, wherein the light control device 556 is preferably secured to or integral with the housing cover 540. The light control device 556 generally includes a cavity 562 in a bottom portion 564 thereof, as best seen in FIG. 19. Various embodiments of light control devices 556 will be discussed in greater detail hereinafter.

As seen in FIG. 19, the base portion 506 of the device encloses control circuitry shown at 570. In particular, the base 508 includes a support structure 572 extending upwardly therefrom that supports a printed circuit board (PCB) 574. An LED 576 is operatively connected to and extends upwardly from a central portion 578 of the PCB 574. As best seen in FIGS. 20 and 21, an emission frequency actuator arm 580 extends through a rectangular aperture 582 in a bottom portion of the base 508. The emission frequency actuator arm 580 is operatively connected to a slide switch 583, wherein the slide switch 583 is operatively connected to the PCB 574. The actuator arm 580 preferably includes five selectable positions that control the emission frequency of the atomizer assembly 516. Specifically, the slide switch 583 includes a button 584 extending therefrom that is movable along a slot 586 in the slide switch 583 to one of five detent positions. A yoke 588 extending from the actuator arm 580 surrounds the button 584 on sides thereof to move the button 584 along the slot 586. Selection of a position by the user with respect to the actuator arm 580 moves the button 584 within the slot 586, thereby indicating to the slide switch 583 the current position of the actuator arm 580. The positions of the slide switch 583 are detected by the PCB 574. Components mounted on the PCB 574 control the atomizer assembly 516 corresponding to the position of the actuator arm 580, wherein each of the positions correspond to different time intervals that define the dwell time or the time between subsequent emission of puffs of active material by the atomizer assembly 516. As discussed above, wires extend from the PCB 574 to the atomizer assembly 516 to actuate the atomizer assembly 416 in dependence upon the position of the actuator arm 580.

The PCB 574 further includes a switch 600 having a depressable button 602 extending upwardly therefrom. Depression of the button 602 turns the LED 576 on or off depending on the current state of the LED 576. The actuation of the button 602 and the operation of the control circuitry 570 will be discussed in greater detail hereinafter.

As noted above, the housing 510 encloses the PCB 574 and other control circuitry and the LED 576. When the housing cover 540 is attached to the housing 510, as discussed in detail above, the LED 576 is disposed in the cavity 562 located at the bottom portion 564 of the light control device 556, such that light emitted from the LED 576 may be reflected and refracted by the light control device 556.

Referring to FIG. 21, the base portion 506 of the device 20 includes a battery door 620 that includes a hinge 622 at a first end 624 thereof and a latching mechanism 626 at a second end 628 thereof. The latching mechanism 626 interacts with a locking recess 630 in the base portion 506 to hold the battery door 620 in a closed position. The latching mechanism 626 may be flexed to release the latching mechanism 626 from the locking recess 630, such that the battery door 620 may pivot about the hinge 622 to open the battery door 620 and allow access to a battery compartment 631.

As further seen in FIG. 19, the base portion 506 of the device 500 includes two batteries 640 that preferably provide direct current that is converted into high-frequency alternating current power that is selectively applied to the atomizer assembly 516 and the LED 576. Optionally, the device 500 may be powered by alternating household current, which is rectified, converted to high-frequency alternating current power, and reduced in voltage and applied intermittently to the atomizer assembly 516 and/or the LED 576. The batteries 640 may be any conventional dry-cell battery such as "A", "AA", "AAA", "C", and "D" cells, button cells, watch batteries, and solar cells, but preferably, the batteries 640 are "AA" or "AAA" cell batteries. Although two batteries are preferred, any number of batteries that would suitably fit within the device 500 and provide adequate power level and service life may be utilized.

The base portion 506 may further include optional feet 642 extending therefrom to aid in stabilizing the active material emitting device 500. Although four feet 642 are depicted, any suitable number of feet 642 for stabilizing the device 500 may be utilized.

Figure 22:
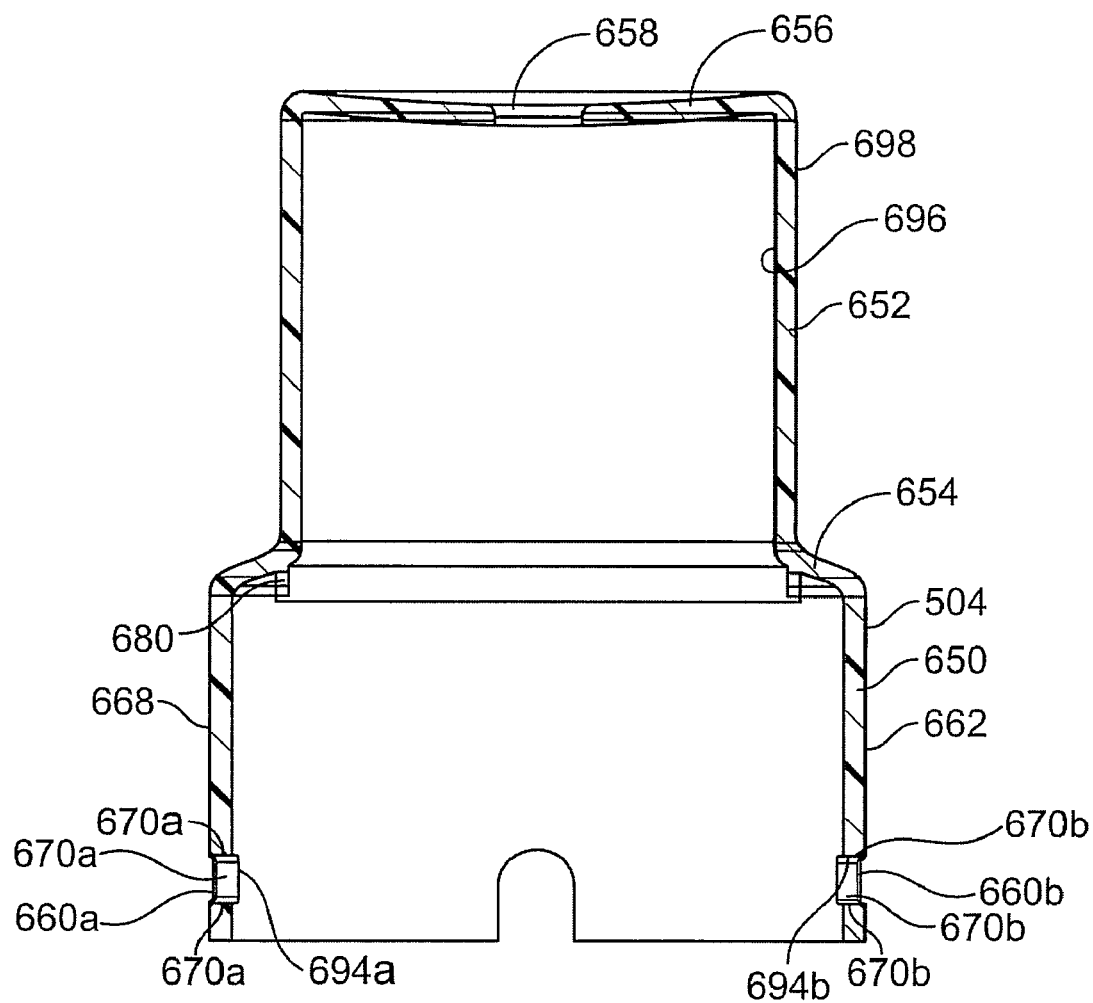
FIG. 22 is a cross-sectional view taken generally along the lines 22-22 illustrating a cover portion of the device of FIG. 15A.

Referring to FIG. 22, the cover portion 504 includes a lower cylindrical wall 650 having a first diameter and an upper cylindrical wall 652 having a second diameter that is preferably smaller than the first diameter. An angled wall 654 joins the lower cylindrical wall 650 to the upper cylindrical wall 652. The cover portion 504 further includes a circular top wall 656 adjacent the upper cylindrical wall 652 and having a circular aperture 658 disposed in a central portion thereof.

As seen in FIGS. 19 and 22, the cover portion 504 is positioned over the base portion 506 during use of the device 500. Specifically, the cover portion 504 includes first and second apertures 660a, 660b disposed opposite one another in a periphery 662 of the lower cylindrical wall 650. The base portion 506 includes first and second spring clips 664a, 664b, as seen in FIG. 17, extending from opposing sides of the housing 510. Each of the spring clips 664a, 664b includes a protrusion 666a, 666b, respectively, extending outwardly therefrom. In use, the cover portion 504 is placed over the base portion 506 such that the upper cylindrical wall 652 surrounds the column 512, the arm portion 514, and the atomizer assembly 516, and the lower cylindrical wall 650 abuts an outer wall 668 of the housing 510. The cover portion 504 is further positioned over the base portion 506 such that the atomizer assembly 516 is aligned with the aperture 658 in the top wall 656 of the cover portion 504. The aperture 658 provides an outlet for active material that is atomized by the atomizer assembly 516 and emitted from the device 500. As the cover portion 504 is placed over the base portion 506, the spring clips 664a, 664b are pressed inwardly by the user. Once the apertures 660a, 660b in the lower cylindrical wall 650 are aligned with the protrusions 666a, 666b extending from the spring clips 664a, 664b, the user may release the spring clips 664a, 664b. As the spring clips 664a, 664b are released, the protrusions 666a, 666b move outwardly into the apertures 660a, 660b. Walls 670a, 670b defining each of the protrusions 666a, 666b, respectively, thereby interfere with walls 672a, 672b defining the respective aperture 660a, 660b to prevent removal of the cover portion 504 from the base portion 506. If the user desires to remove the cover portion 504, the user may press inwardly on the spring clips 664a, 664b and remove the cover portion 504.

Figure 15B:
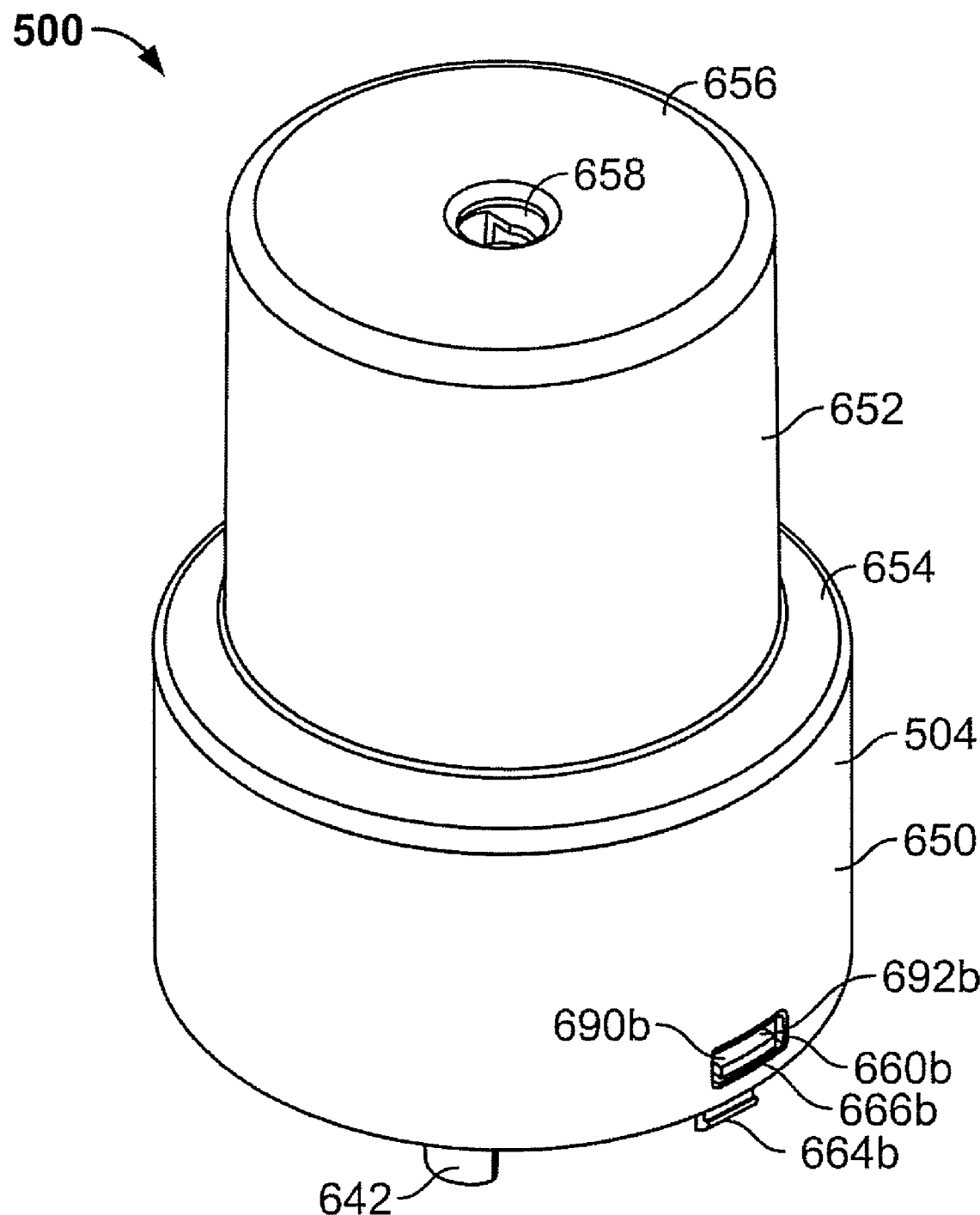
FIG. 15B is a top isometric view of the device of FIG. 15A.
Figure 16:
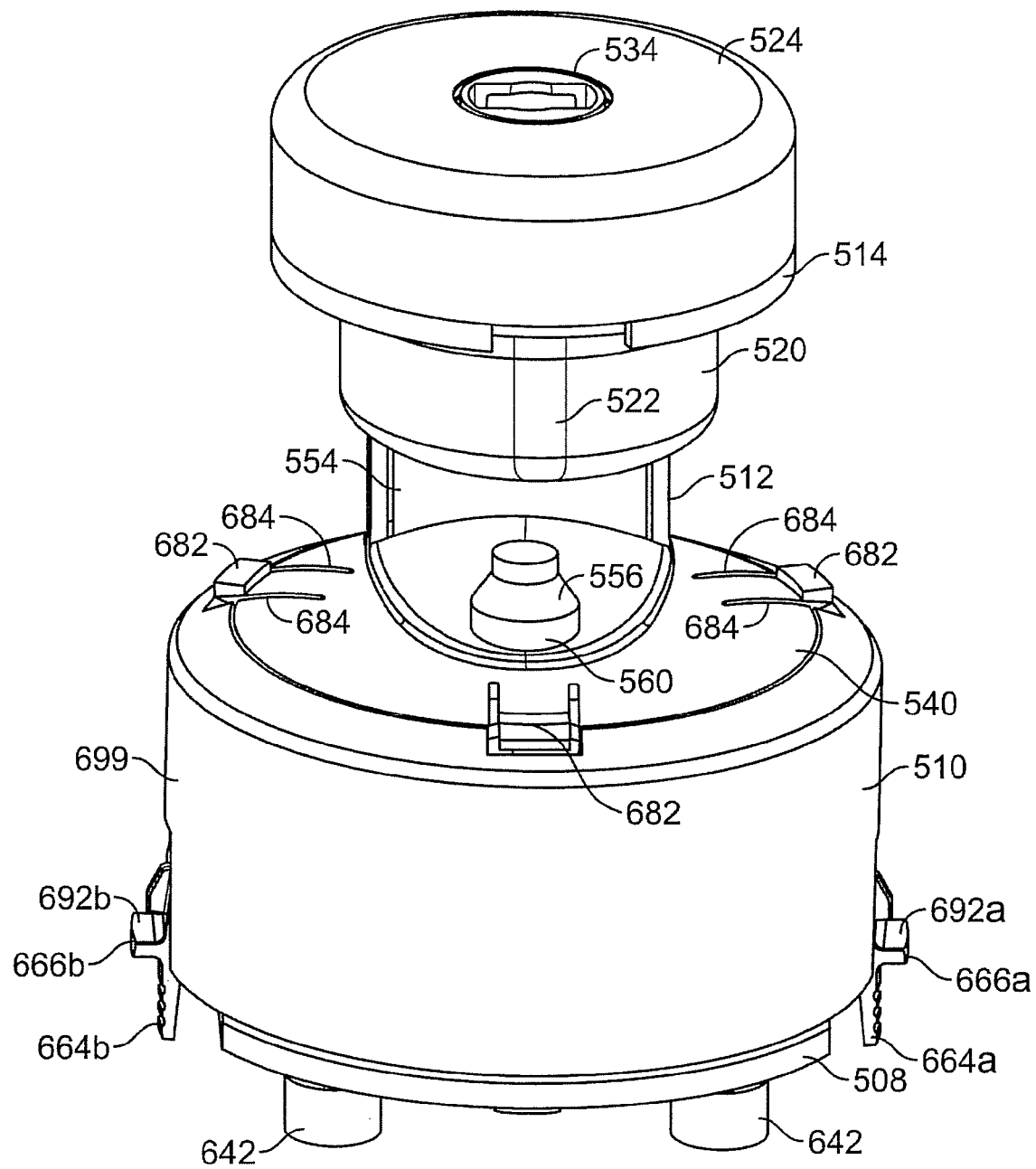
FIG. 16 is a top isometric view illustrating the device of FIG. 15A with a cover portion removed therefrom.
Figure 18:
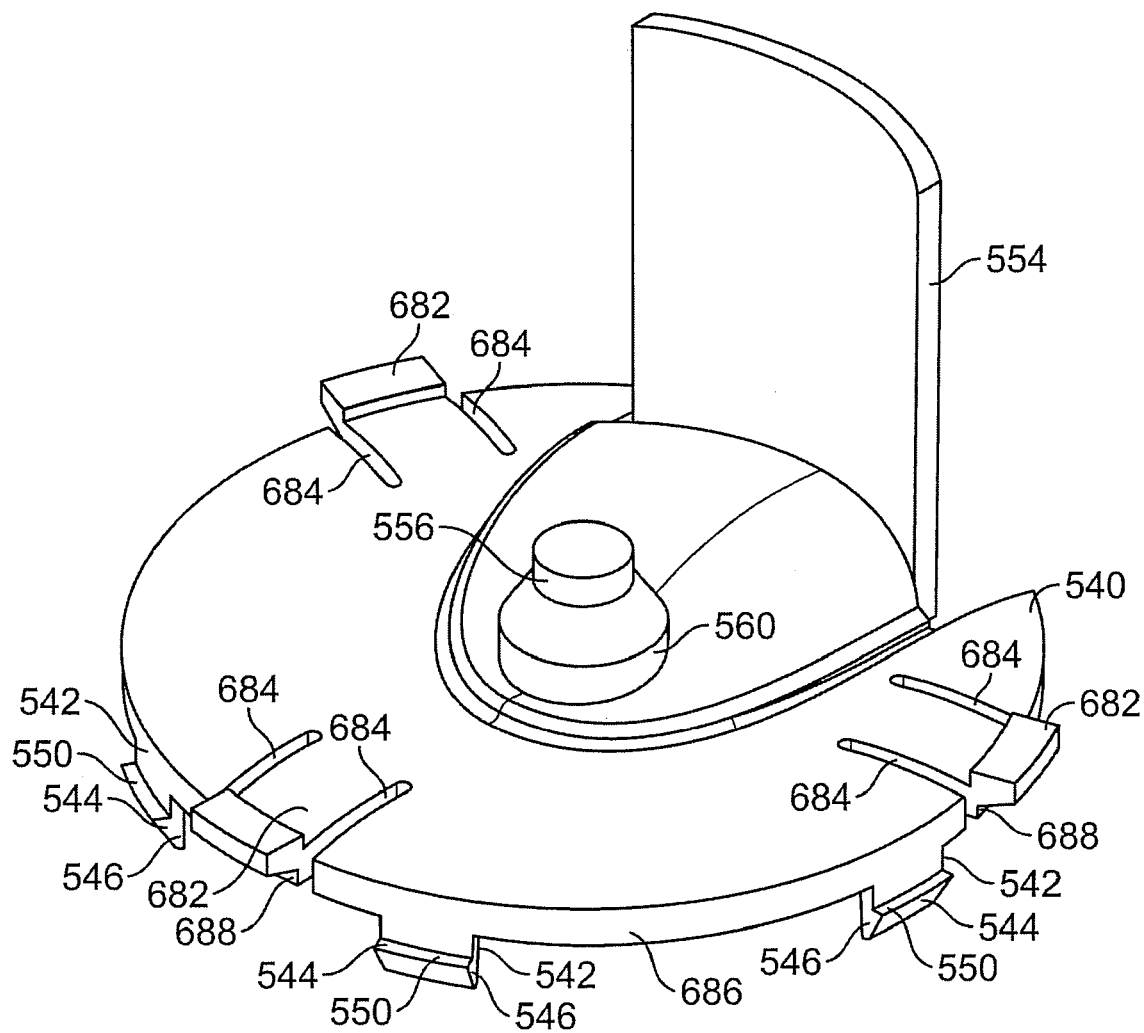
FIG. 18 is a is a top isometric view illustrating a housing cover as depicted in the device of FIG. 15A.

As best seen in FIG. 22, the cover portion 504 further includes an annular ring 680 extending downwardly from an intersection of the upper cylindrical wall 652 and the angled connecting wall 654 of the cover portion 504. As seen in FIG. 18, the housing cover 540 includes a plurality of spring fingers 682 in part defined by slots 684 that extend inwardly from a periphery 686 of the housing cover 540. Each of the spring fingers 682 includes a projection 688, as best seen in FIG. 18, extending downwardly therefrom. The annular ring 680 rides on top of the spring fingers 682, which are resilient and act as flexures biased upwardly. Thus, as seen in FIGS. 15A and 15B, the cover portion 504 is biased in a position such that a upper surfaces 692a, 692b of the protrusions 666a, 666b are spaced from upper walls 694a, 694b of the apertures 660a, 660b to create gaps 690a, 690b therebetween. The gaps 690a, 690b allow movement of the cover portion 504 in a vertical direction relative to the housing 510. A user may therefore exert downward pressure on the cover portion 504 against the bias of the resilient spring fingers 682 that act as flexures. Such pressure allows the cover portion 504 to move downwardly until the upper surfaces 692a, 692b of the protrusions 666a, 666b of the spring clips 664a, 664b abut the upper walls 694a, 694b respectively, of the apertures 660a, 660b. As the cover portion 504 moves downwardly, the annular ring 680 flexes the spring fingers 682 downwardly. As the spring fingers 682 move downwardly, one of the projections 688 extending downwardly from the spring fingers 682 that is aligned with the depressable button 602 contacts the depressable button 602, thereby activating the switch 600. A change in state of the switch 600 is detected by the PCB 574 and the LED 576 is turned on (for a predetermined timeframe) or off depending on the current state of the LED 576, as described in greater detail hereinafter.

The cover portion 504 is preferably made of a transparent or translucent material, such as glass and/or a polymeric resin, such that the cover portion 504 functions as a light diffuser. All or portions of an inner surface 696 and/or an outer surface 698 of the cover portion 504 may include a surface treatment, such as a frosted surface, a coating, a roughened surface, a textured surface, and/or the like, in order to provide an even dispersion of light through the cover portion 504. Optionally, one or more of a lower portion 699 (FIG. 19) of the housing 510 or the lower cylindrical wall 650 of the cover portion 504 may include a decal or other obscuring element thereon in order to prevent the electronics of the device 500 from being viewed from outside the device 500. Still optionally, a decal or other obscuring element may be positioned on the upper cylindrical wall 652 of the cover portion 504.

Figure 23:
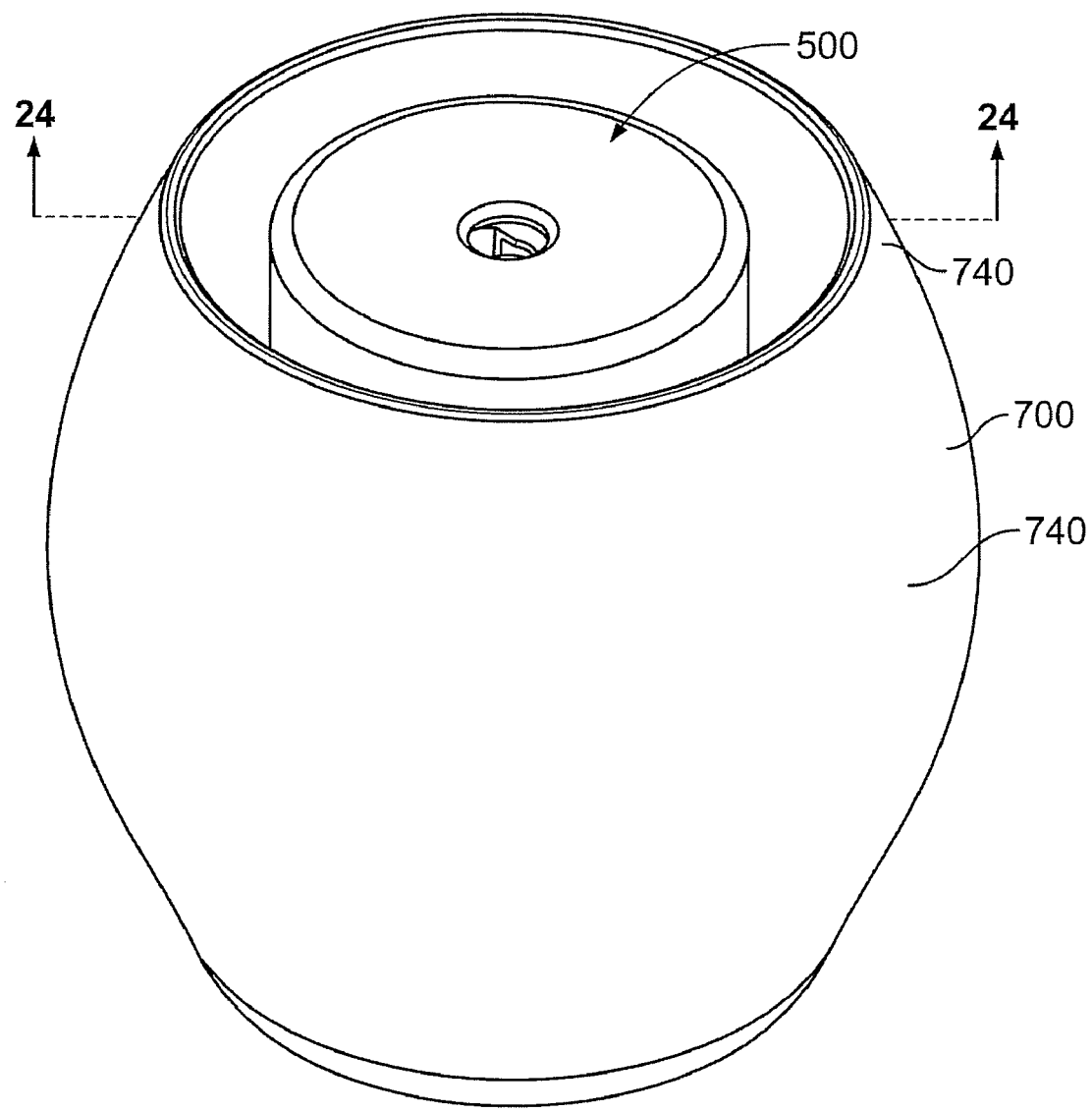
FIG. 23 is an isometric view illustrating the device of FIG. 15A disposed within a container.
Figure 24:
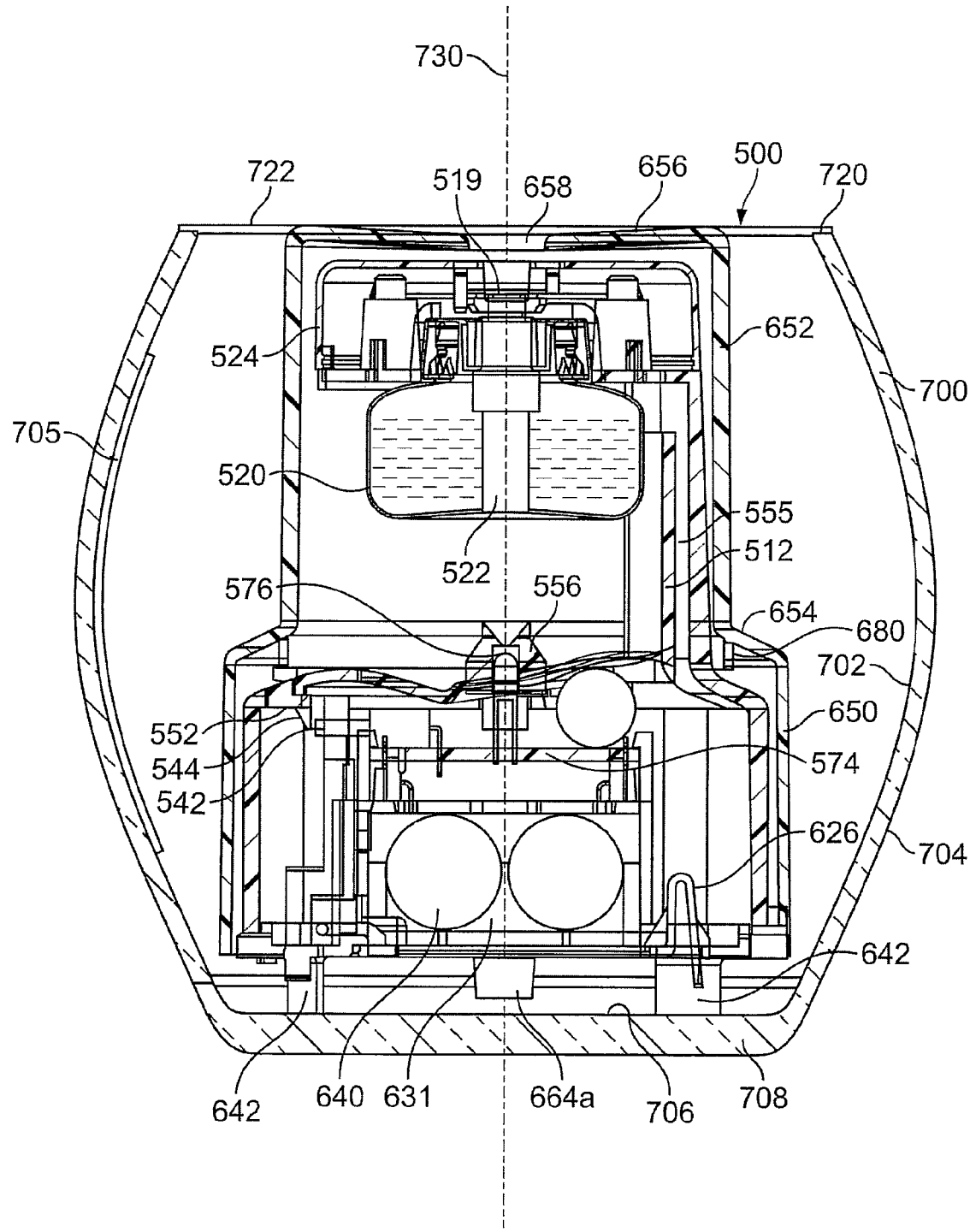
FIG. 24 is a cross-sectional view taken generally along the lines 24-24 of FIG. 23.

As seen in FIGS. 23 and 24, the active material emitting device 500 may be placed into a container 700 for use thereof, or may be placed on a surface and used alone. The container 700 also preferably acts as a light diffuser and may be made of a transparent or translucent material, such as glass and/or a polymeric resin. All or portions of an inner surface 702 and/or an outer surface 704 of the container may include a surface treatment, such as a frosted surface, a coating, a roughened surface, a textured surface, and the like, to provide relatively even dispersion of light through the container 700. Optionally, one or more images may be formed on the container 700 by placing a sticker 705 or other image-forming device (such as a decal) on a surface thereof. Still optionally, etchings may be formed in the light control device 556 to project a shape or shadow, as desired.

Although one shape of container is depicted herein, any shape of container is contemplated, as long as the device 500 fits sufficiently therein.

Referring to FIG. 24, the active material emitting device 500 is disposed within the container 700 such that the feet 642 of the device 500 rest upon an upper surface 706 of a bottom portion 708 of the container 700. Preferably, the device 500 fits within the container 700 without portions of the lower or upper cylindrical walls 650, 652 touching the inner surface 702 of the container 700.

Figure 29:
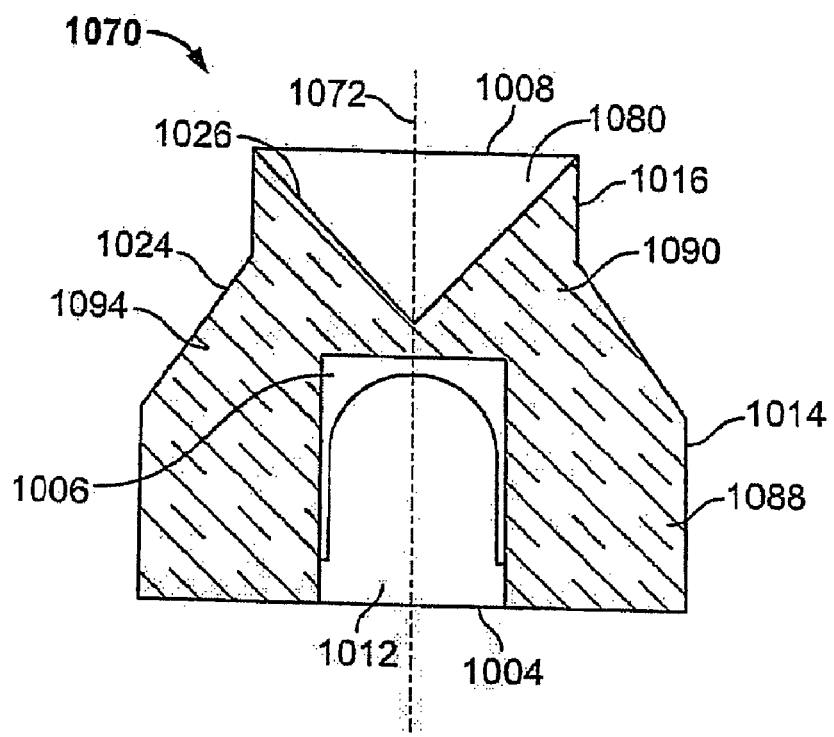
FIG. 29 is a cross-sectional view of yet another embodiment of a light control device.

As further seen in FIG. 24, the top wall 656 of the housing cover 540 is preferably aligned with an annular rim 720 disposed at a top portion 722 of the container 700. Optionally, the top wall 656 of the housing cover 540 may be disposed at, slightly below, or above the annular rim 720. During operation of the device 500 within the container 700, the device 500 emits liquid from the container 520 into the air surrounding the container 700 by means of the atomizer assembly 516. The greater the vertical distance is between the top wall 656 of the housing cover 540 and the annular rim 720, the greater the distance is between the atomizer assembly 516 and the annular rim 720. When the distance between the atomizer assembly 516 and the annular rim 720 is too great, an effect called "fallout" may occur. When active material is emitted by the atomizer assembly 516, it must be emitted upwardly a distance great enough to allow the transient air flow of the surroundings to carry the active material throughout the surroundings. When the top wall 656 of the housing cover 540 is disposed too far below the annular rim 720, the active material is not emitted by the atomizer assembly upwardly a distance great enough for this to occur. Thus, the active material falls downwardly without being carried throughout the surroundings, thereby causing the active material to fall into the container, onto the housing cover 540, and onto a surrounding surface. This "fallout" effect prevents the device 500 from efficiently dispersing active material into the surroundings and also creates a potentially undesirable accumulation of material. For this reason, it is also necessary to orient the atomizer assembly 516 and the LED 576 such that the atomizer assembly 516 is disposed above the LED 576 in order to prevent "fallout." In one embodiment, to prevent fallout, the orifice plate 519 of the atomizer assembly 516 is disposed 0.25 inch (6.35 mm) or less from the annular rim 720 of the container 700.

Other features in addition to or in place of the positioning of the orifice plate 519 of the atomizer assembly 516 with respect to the annular rim 720 of the container 700 are possible. For example, apertures may be disposed in the container 700 to increase air flow within the device and therefore carry the emitted active material into the air surrounding the container 700. Another feature might include increasing the time for which the active material is emitted, and thereby increasing the inertia created by the active material and increasing the amount of active material that is carried away from the device into the air surrounding the device.

Any light emitted upwardly from the LED 576 along a longitudinal axis 730 of the device 500 is blocked from exiting the device 500 by the atomizer assembly 516 and container 520 due to the positioning of such components above the LED 576. The light control device 556 that is disposed above and around the LED 576 is provided to reflect and/or refract light that is emitted from the LED 576. Most of the light that is emitted upwardly along the longitudinal axis 730 is reflected and/or refracted by the light control device 556 and emitted from the device 500 radially outwardly through a central portion thereof. As seen in FIG. 23, this positions the light around a center portion 740 of the container 700 and device 500, instead of near a top portion 742 thereof.

FIGS. 25-31 depict various embodiments of light control devices that may be used with any of the embodiments as disclosed herein. The light control devices transmit light therethrough from a light receiving end to an opposite light dispersion end where a facet generally reflects a portion of the transmitted light laterally, or radially outwardly, as seen in FIG. 25 and may transmit a portion therethrough. These embodiments are suitable for use in various light apparatuses alone and/or in combination with other light pipes and/or light diffusers. The light pipes of FIGS. 25-31 are preferably made of a transparent or translucent material suitable for transmitting light from the light receiving end to the light dispersion end, such as glass and/or a polymeric resin. A preferred material for the light control devices is a clarified propylene. Although the cross-sections of such light pipes are depicted as being circular, other non-circular cross-sections are possible.

Referring to FIG. 25, a light pipe 1000 extends along a longitudinal axis 1002 between a light receiving end 1004 having a cavity 1006, such as a cylindrical bore, disposed therein and a light dispersing end 1008 having a reflective facet 1010 disposed therein. The cavity 1006 is sized to receive a light source, such as an LED 1012. The light pipe 1000 has substantially smooth or polished first and second exterior surfaces 1014, 1016, defining first and second cylindrical portions 1018, 1020, wherein the first portion 1018 has a diameter greater than a diameter of the second portion 1020. The first cylindrical portion 1018 also has a height that is preferably greater than a height of the second cylindrical portion 1010. A tapered exterior surface 1022 defines a frustoconical portion 1024 that is disposed between the first and second exterior surfaces 1014, 1016 and the first and second cylindrical portions 1018, 1020. The reflective facet 1010 includes a conical depression extending across and into the light dispersion end 1008 through the second cylindrical portion 1018 and into the frustoconical portion 1024. The conical depression of the facet 1010 forms a reflective surface 1026 that is angularly displaced from the longitudinal axis 1002 so as to disperse most of the transmitted light as indicated by light rays 1027 from the LED laterally, or radially outwardly, as seen in FIG. 25.

FIGS. 26-28 are three variations of another embodiment of a light pipe 1030 that extends along a longitudinal axis 1032 between a light receiving end 1034 having a cavity 1036, such as a cylindrical bore, disposed therein and a light dispersing end 1038 having a reflective facet 1040 disposed therein. The cavity 1036 is sized to receive a light source, such as an LED 1042. The light pipe 1000 has substantially smooth or polished first and second exterior surfaces 1046, 1048 defining first and second cylindrical portions 1050, 1052, wherein the first portion 1050 has a diameter greater than a diameter of the second portion 1052. FIGS. 26-28 depict three variations of the same embodiment wherein the diameters of the first and second portions 1050, 1052 are varied to receive different light dispersion results. Specifically, the first and second portions 1050, 1052 of FIG. 27 have the smallest diameters and the first and second portions 1050, 1052 of FIG. 28 have the largest diameters whereas the first and second portions 1050, 1052 of FIG. 26 have diameters intermediate the diameters of the corresponding portions 1050, 1052 of FIGS. 27 and 28. Differences in diameter of the first and second portions 1050, 1052 alter a height along the longitudinal axis 1032 and a diameter of the reflective facet 1040 at the light dispersing end 1038.

Still referring to FIGS. 26-28, a rounded exterior surface 1054 defining a shoulder portion 1056 is disposed between the first and second exterior surfaces 1046, 1048 and the first and second cylindrical portions 1050, 1052. The reflective facet 1040 includes a conical depression that forms a reflective surface 1058 that is angularly displaced from the longitudinal axis 1032 so as to disperse most of the light transmitted from the LED laterally, or radially outwardly, as depicted in FIG. 25.

The light pipe 1070 of FIG. 29 extends along a longitudinal axis 1072 and includes a reflective facet 1080 having the same shape as the light pipe 1000 of FIG. 25, except that a reflective facet 1080 only extends through a second cylindrical portion 1090 and does not extend into a third portion 1094. Further, the heights of first and second cylindrical portions 1088, 1090 are substantially equal or nearly so, instead of one being greater than the other.

Figure 25:
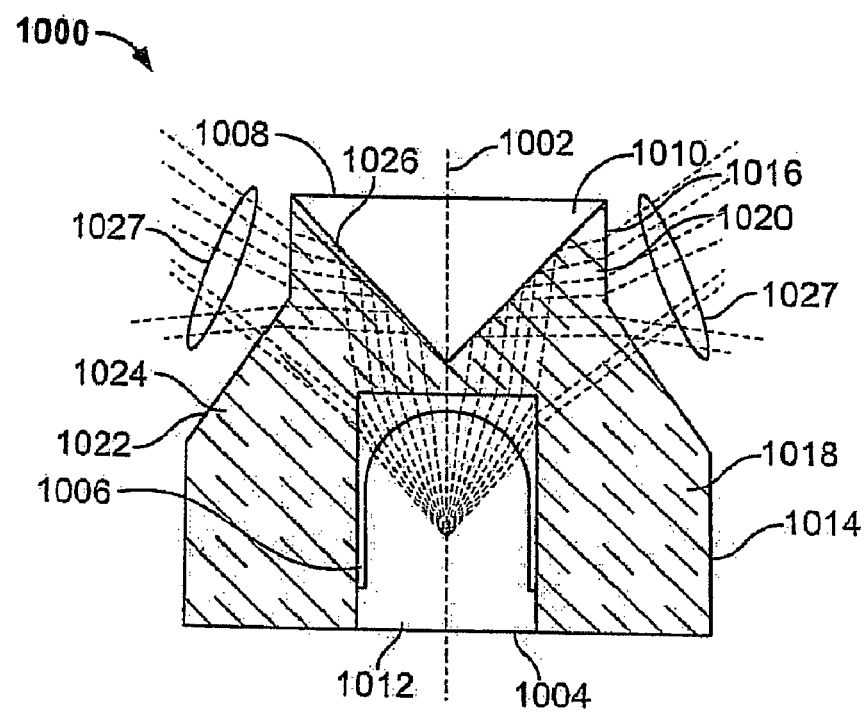
FIG. 25 is a cross-sectional view of one embodiment of a light control device.
Figure 26:
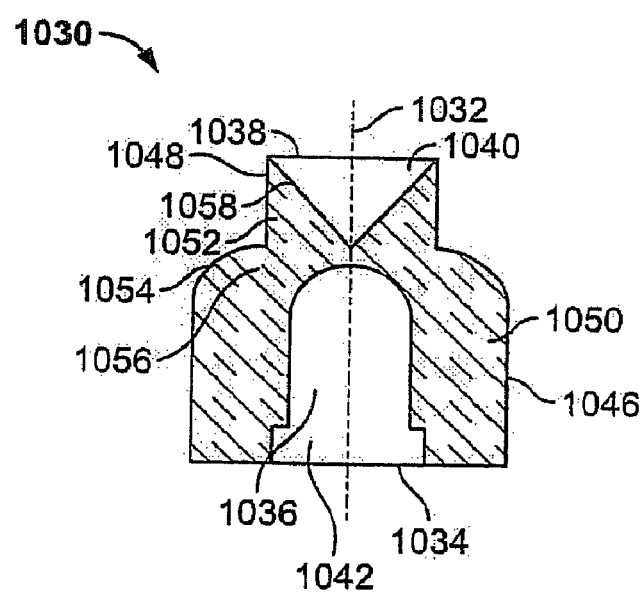
FIGS. 26-28 are cross-sectional views of three variations of another embodiment of a light control device.
Figure 27:
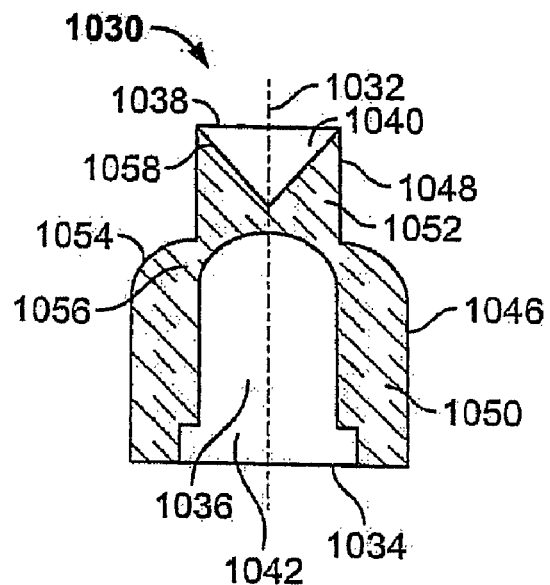
Figure 28:
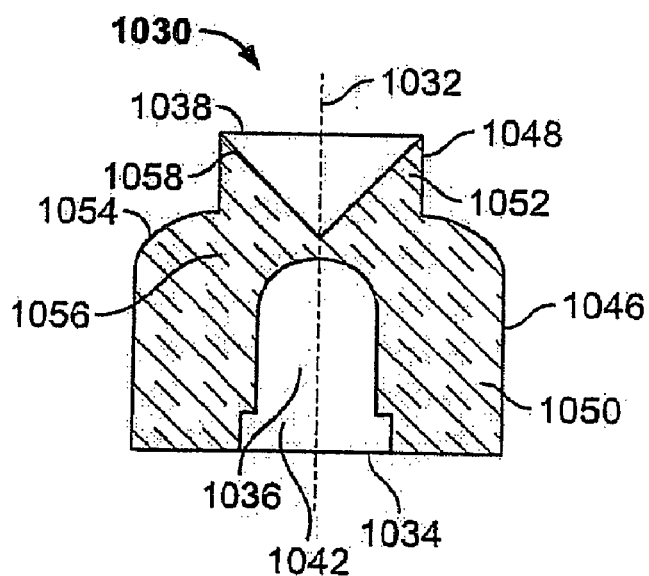
Figure 30:
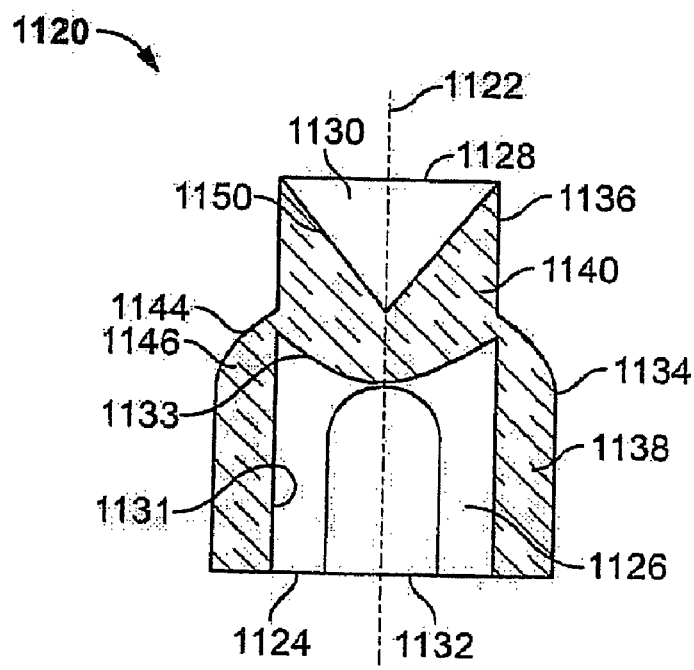
FIG. 30 is a cross-sectional view of still another embodiment of a light control device.

Referring to FIG. 30, a light pipe 1120 extends along a longitudinal axis 1122 between a light receiving end 1124 having a cavity 1126, such as a cylindrical bore, disposed therein and a light dispersing end 1128 having a reflective facet 1130 similar to that discussed with respect to FIG. 25. The cavity 1126 is sized to receive at least one light source, such as an LED 1132, therein. The cavity 1126 is defined by a cylindrical side wall 1131 and a curved top wall 1133 that extends into the cavity 1126. The light pipe 1120 has substantially smooth or polished first and second exterior surfaces 1134, 1136 defining first and second cylindrical portions 1138, 1140, wherein the first portion 1138 has a diameter greater than a diameter of the second portion 1140. A rounded exterior surface 1144 defining a shoulder portion 1146 connects the first and second exterior surfaces 1134, 1136 and the first and second cylindrical portions 1138, 1140.

As seen in FIG. 30, the reflective facet 1130 only extends through the second portion 1140 and does not extend into the shoulder portion 1146. The reflective facet 1130 further forms a reflective surface 1150 that is angularly displaced from the longitudinal axis 1122 to disperse most of the light transmitted from the LED laterally, or radially outwardly, as seen in FIG. 25.

Figure 31:
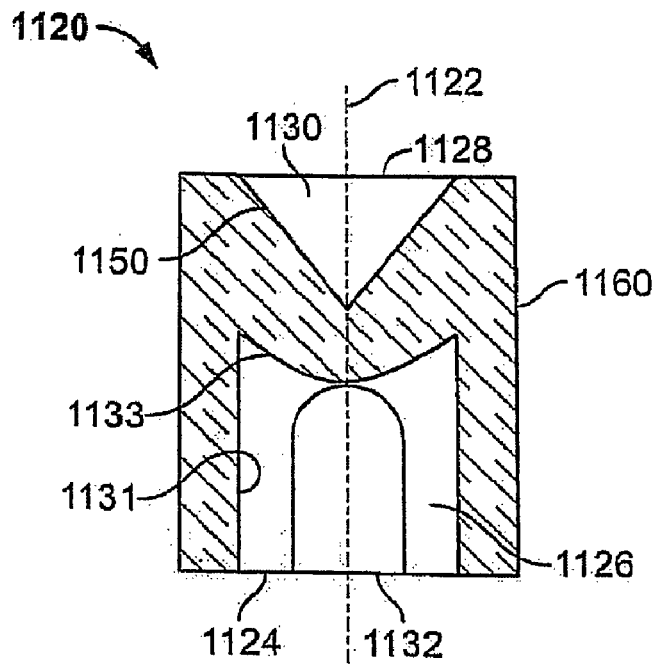
FIG. 31 is a cross-sectional view of another embodiment of a light control device.

The embodiment of FIG. 31 is similar to that of FIG. 30. The light pipe 1120 of FIG. 31 differs in that the light pipe 1120 includes a single cylindrical exterior surface 1160 having a substantially constant diameter throughout.

In the embodiments of FIGS. 25-31, the LED is connected to a PCB of a light apparatus in which it is disposed in order to power and control the LED. Although embodiments of light pipes herein are depicted as having a relatively small dimension along a longitudinal axis, this dimension may be increased or decreased as necessary to create the necessary light dispersions.

Although the embodiments of FIGS. 25-31 are described as having smooth surfaces defining the respective light pipes, roughened or textured surfaces may also be utilized.

The operation of the active material emitting device 500 of FIGS. 15A-24 will now be described in detail. When a user desires to operate the device 500, the battery door 620 is opened using the latching means 626 and batteries 640 are placed within the battery component 555. To insert a container 520 having an active material therein, the cover portion 504 is removed from the device 500, as described in detail above, an old container 520 is removed and/or a new container 520 is inserted, and the cover portion 504 is placed back onto the device 500, as described in detail above. The order of insertion of the batteries 640 and a container 520 may be reversed, but as soon as both are inserted, the device 500 begins emitting the active material.

The user may then move the actuator arm 580 (FIG. 21) to set the dwell time for emission of the active material. Once the dwell time is set, the device 500 may be placed in a container 700. It is not until the user depresses the cover portion 504, as described in detail above, that the LED 576 will turn on. The LED 576 can be turned off by a subsequent depression of the cover portion 504 or the LED 576 will automatically shut off after a predetermined time period, such as three hours or four, as described in greater detail below.

Figure 32:
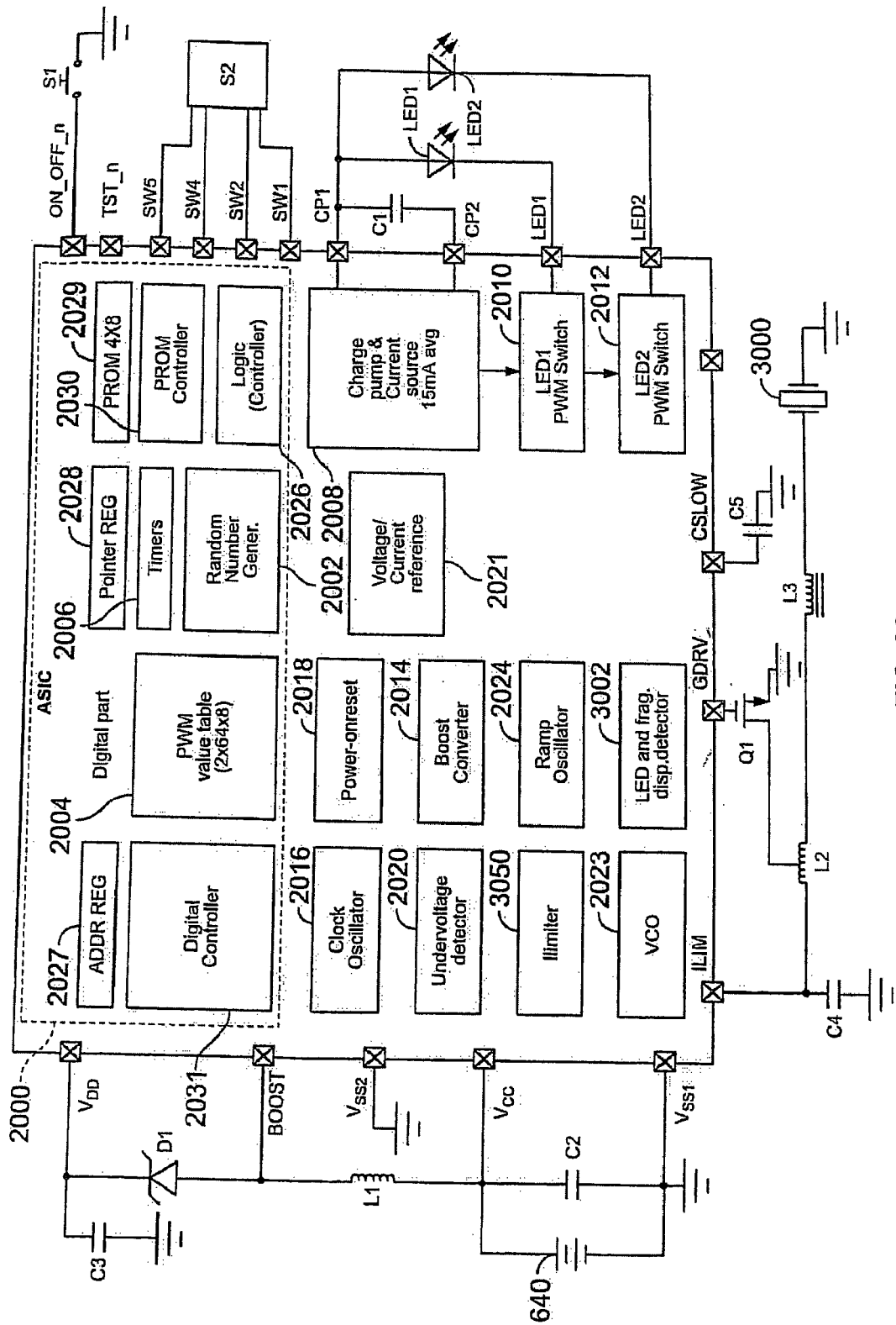
FIG. 32 is a block diagram of an integrated circuit that implements a control device according to yet another embodiment together with external circuitry connected thereto.

FIG. 32 illustrates a programmable device in the form of an application specific integrated circuit (ASIC) 2000 that operates in conjunction with further electrical components to control the energization of any of the LED's described above and, optionally, any of the active material emitters or atomizer assemblies described above (each of the emitters and atomizer assemblies is referred to as an active material dispenser hereinafter). If desired, the ASIC 2000 may be replaced by a microprocessor, any other programmable device or a series of discrete logic and electronic devices. In general, in one mode of operation, the ASIC 2000 operates only a single LED2, such as the LED 576, or any of the other LED's described above, such that LED2 appears to flicker. If two independently operable LED's are present, the ASIC 2000 operates the LED's such that a further LED1 appears to be continuously energized and LED2 appears to flicker. If desired, this arrangement could readily be modified by one of ordinary skill in the art such that LED1 appears to flicker and LED2 appears to be continuously energized. In a still further embodiment, LED1 and LED2 could be operated in a non-independent fashion such that both are caused to appear to flicker or appear to be continuously energized. Still further, in the illustrated embodiment, if the ASIC 2000 is connected to and independently operates both LED1 and LED2, circuitry internal to the ASIC 2000 for operating the active material dispenser is disabled and the active material dispenser is omitted. Alternatively, in those embodiments where two or more LED's are to be operated together (i.e., not independently, such as LED 1 and LED 2 discussed above), the ASIC 2000 could be modified in a manner evident to one of ordinary skill in the art given the disclosure herein such that disabling of the active material dispenser circuitry does not occur and the active material dispenser can be connected to the ASIC 2000 and be operated thereby. Also, while in the illustrated embodiment the active material dispenser is operable by the ASIC 2000 only when one or two LED's are connected thereto, the ASIC 2000 could be modified by one of ordinary skill in the art such that the ASIC 2000 can operate an active material dispenser as described above even when no LED is connected to the ASIC 2000.

In the preferred embodiment, LED1 and LED2 are operated in a pulse-width mode (PWM) of operation. Specifically LED1, when used, is provided a high frequency PWM waveform that results in the appearance that LED1 is continuously energized. The duty cycle for the PWM waveform and the frequency for the PWM waveform are fixed. Regardless of whether LED1 is used, LED2 is energized to obtain the flickering effect by utilizing a pseudo random number generator 2002 (shown in block diagram form in FIG. 32 and shown functionally in FIG. 33) in conjunction with PWM value tables 2004 and one or more of a plurality of timers 2006 to establish a duty cycle for operation of LED2 (the PWM value tables 2004 and the timers 2006 form a digital portion of the ASIC 2000). The pseudo random number generator 2002 is functionally shown in FIG. 33 as a series of three NOR gates G1, G2, and G3 coupled to particular bit positions of a sixteen-bit shift register SR. The initial value of the generator 2002 is 3045 (hexadecimal). The waveform generation processes to obtain the flickering effect for single LED operation and dual independent LED operation are described in greater detail below.

Referring again to FIG. 32, the ASIC comprises control apparatus including a charge pump and average current source 2008, a PWM switch 2010 for LED1, and a PWM switch 2012 for LED2. A capacitor C1 is coupled across terminals CP1 and CP2 and stores charge from the batteries 640 and charge pump 2008 to permit continued operation of LED1 (if used) and LED2 even when the output voltage of the batteries 640 falls below the voltage required to turn on such LED(s). The light emitting diode LED2 is coupled across terminals CP1 and LED2 whereas the light emitting diode LED1 (if used) is coupled across terminals CP1 and LED1.

The ASIC 2000 receives power from the batteries 640, which, as noted above, may be a pair of series-connected conventional AA 1.5 v cells, at terminals VCC and VSS1. A capacitor C2 is coupled across the terminals VCC and VSS1 for filtering purposes. Preferably, the terminal VSS1 is connected to ground potential. A boost converter 2014 of the ASIC 2000 in conjunction with a capacitor C3, a Schottky diode D1, and an inductor L1 all external to the ASIC 200 and coupled to terminals VDD, BOOST, and VCC provide a supply voltage at the terminal VDD. In the event that the active material dispenser circuitry is not utilized, the diode D1, the inductor L1, and the capacitor C3 are omitted and the terminal VDD is directly coupled to the terminal VCC and the BOOST terminal is left unconnected. The ASIC 2000 further receives a signal at an ON_OFF terminal from a switch S1 (that preferably comprises the switch 600 of FIG. 20) that is in turn coupled to ground. The ASIC 2000 includes an internal debouncer (not seen in FIG. 32) that debounces the signal developed by the switch S1.

The ASIC 2000 further includes a clock oscillator 2016 that serves as an internal clock for the ASIC 2000, a power-on reset circuit 2018 that resets various parameters upon energization of the ASIC 2000, and an undervoltage detector 2020 that disables the ASIC 2000 when the battery voltage drops below a particular level. A voltage/current reference circuit 2021 assists in determining when to activate the charge pump for the LED's and is a reference for when to disable the ASIC 2000 as the batteries 640 discharge. The VCO 2023, in turn, receives a ramp voltage developed on a terminal CSLOW by a ramp oscillator 2024. The ramp oscillator 2024 and the VCO 2023 control the active material dispenser, when used, as noted in greater detail hereinafter.

Still further in the preferred embodiment, the digital portion of the ASIC 2000 further includes a system controller in the form of programmed logic 2026 that executes programming to control the LED's, an eight-bit address register 2027, and an address pointer register 2028. The digital portion further includes a 64×8 programmable read only memory (PROM) 2029, a PROM controller 2030, and a digital controller 2031, all of which generate drive signals for the LED(s). As noted in greater detail hereinafter, in the case where both LED1 and LED2 are used, the value developed by the address pointer register 2028 at any particular time is equal to the value developed by the address register 2027 at that time with the second and third least significant bits removed from the eight-bit value developed by the address register 2027 and the remaining more significant bits shifted toward the least significant bit. For example, if the value developed by the address register 2027 at a particular time is 01101100, then the output value of the address pointer register 2028 at that time is 011010. Similarly, if the current output value of the address register 2027 is 10101001, 00001110, or 10011111, then the current output value of the address pointer register 2028 is 101011, 000010, or 100111, respectively. In the case where only LED2 is used, the value developed by the address pointer register 2028 at any particular time is equal to the six least significant bits of the value developed by the address register 2027 at that time.

Figure 34:
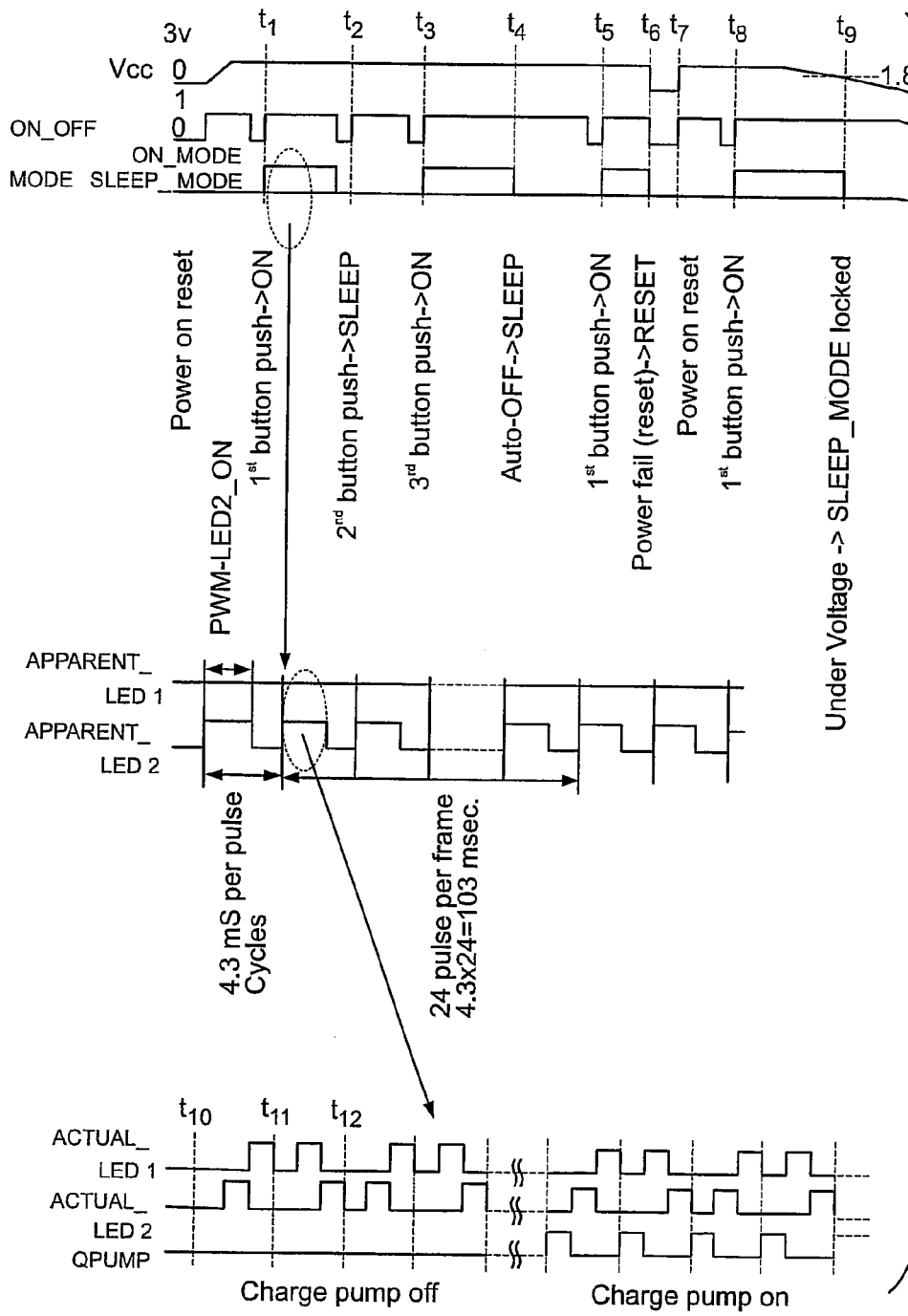
FIG. 34 is a series of waveform diagrams illustrating a portion of the operation of the integrated circuit of FIG. 32.

Referring next to FIG. 34, a series of waveform diagrams illustrate operation of the circuitry of FIG. 32 under the assumption that LED1 and LED2 are connected as shown in FIG. 32. If, on the other hand, LED1 is omitted, the illustrated waveforms for LED2 remain the same, whereas no current is supplied to the LED1 terminal of the ASIC 2000. Also, the flicker pattern for LED2 is different when LED1 is not used as compared to when LED1 is used, in the manner and for the reasons described hereinafter.

The waveform diagram labeled MODE of FIG. 34 reflects the operation of the ASIC 2000 in response to various conditions including the open/closed state of the switch S1. The terminal ON_OFF has an internal pull-up feature such that when the switch S1 is open, as seen in FIG. 32, the voltage VDD is supplied to the debouncer (the debouncer is implemented by the system controller 2026). When the switch S1 of FIG. 32 is closed, a low state signal in the form of ground potential is supplied to the debouncer, as reflected in the transition between one and zero states in the ON_OFF signal illustrated in FIG. 34. Upon release of the switch S1, a transition occurs from the zero to one states of the ON_OFF signal. The ASIC 2000 then enters an on condition mode at a time $t_1$ provided that the debouncer received the zero state signal for at least a predetermined period of time, such as 25 milliseconds. During operation in the on mode, the LED(s) is (are) energized, as noted in greater detail hereinafter. When the switch S1 is momentarily closed then opened at a time $t_2$ for at least the predetermined period of time, the ASIC 2000 enters a sleep mode of operation, during which only the debouncer is active so as to retain the capability of detecting momentary closure of the switch S1 for at least the predetermined period of time. Thereafter, closure and opening of the switch S1 at a time $t_3$ for at least the predetermined period of time causes the ASIC 2000 to reenter the on mode.

Following the time $t_3$, if the switch S1 is not actuated within a predetermined delay period (referred to hereinafter as the "auto shut-off delay period"), the ASIC 2000 automatically enters the sleep mode, as represented at time t4. This auto shut-off delay period is variable depending upon whether the active material dispenser or LED1 are not used. Specifically, if a terminal GDRV is not connected to ground, but instead is connected to external circuitry that implements the active material dispenser, as discussed in detail hereinafter, the predetermined delay period is set equal to three hours. Otherwise, the predetermined delay period is set equal to four hours. A subsequent momentary closure and opening of the switch S1 at a time $t_5$ causes the ASIC 2000 to again enter the on mode.

At a time $t_6$ the power provided to the ASIC 2000 is interrupted, such as by removal of one or more of the batteries 640. Upon reapplication of power to the ASIC 2000 at a time $t_7$, a power-on reset mode is entered wherein values used by the ASIC 2000 are initialized. Thereafter, the ASIC 2000 enters the sleep mode until the switch S1 is again momentarily closed and opened at time $t_8$. Following the time $t_8$, the ASIC 2000 remains in the on mode until the auto shut-off delay period has expired, or until the switch S1 is momentarily closed, or until the voltage developed by the batteries 640 drops below a particular level, such as 1.8 volts, as illustrated at time $t_9$.

As seen in the waveform diagrams illustrated as APPARENT_LED1 and APPARENT_LED2, LED1 (when used) is operated such that it appears to be continuously on whereas the LED2 is operated such that it appears to flicker with a pseudo random flicker pattern. With regard to LED2, a number of frames of equal duration are established wherein each frame includes a number of pulse cycles therein. Preferably, each pulse cycle is 4.3 milliseconds in length and 24 pulses are included per frame. Accordingly, each frame is 103 milliseconds in duration. Also preferably, the pulse on-times for a particular frame are all equal in duration, resulting in a particular average current magnitude for that frame. Also preferably, the pulse-widths in adjacent frames are different so as to provide an average current different from the particular average current magnitude to provide the flickering effect. The choice of the pulse-widths for the frames is controlled by the pseudo random generator 2002 and entries in one of two portions of the PWM value table 2004. When LED1 is used in conjunction with LED2, a first portion of the PWM value table 2004 is accessed. On the other hand, when LED 1 is not used, a second portion of the PWM value table 2004 is accessed.

As illustrated in the bottom three waveforms of FIG. 34, the waveforms ACTUAL_LED1 and ACTUAL_LED2 indicate the drive waveforms applied to LED1 and LED2, respectively, under the assumption that both LED's are used. (The scale of the waveforms ACTUAL_LED1 and ACTUAL_LED2 is greatly expanded relative to the scale of the waveforms APPARENT_LED1 and APPARENT_LED2.) In general, LED1 and LED2 are operated intermittently at a high frequency so as to provide the appearance that the LED's are being operated at a constant intensity level over a period of time. More particularly, between a time $t_{10}$ and a time $t_{12}$, the LED1 receives two pulses of current, as does the LED2. Specifically, in a first one-sixth of a total of two cycles between the times $t_{10}$ and $t_{12}$, neither LED1 nor LED2 receives a current pulse. In a second one-sixth of the two cycles the LED2 receives a pulse of current whereas the LED1 does not. In a third one-sixth of the two cycles the LED1 receives a current pulse whereas the LED2 does not. In a fourth one-sixth of the two cycles (wherein the second cycle begins at a time $t_{11}$) neither the LED1 nor the LED2 receives a current pulse while in a fifth one-sixth of the two cycles LED1 receives a current pulse whereas the LED2 does not. Finally, in a sixth one-sixth of the two cycles the LED2 receives a current pulse whereas the LED1 does not.

Thereafter, the above-described cycle pairs repeat until the combined voltage developed by the batteries 640 drops below the voltage required to adequately energize LED1 and LED2. At this point, the charge pump 2008 is actuated to provide sufficient forward voltage to LED1 and LED2. Specifically, LED1 and LED2 receive the current pulses as described previously and the charge pump 2008 is turned on during the first one-sixth and fourth one-sixth of cycle pair to charge the capacitor C1 of FIG. 32. The capacitor C1 thereafter provides sufficient voltage to LED1 and LED2 to maintain adequate drive thereto. Preferably, the drive pulses for LED1 and LED2 have a 45 milliamp peak current and a typical pulse-width of about 4.2 microseconds. If desired, these values may be changed to obtain different LED intensities.

Figure 35A:
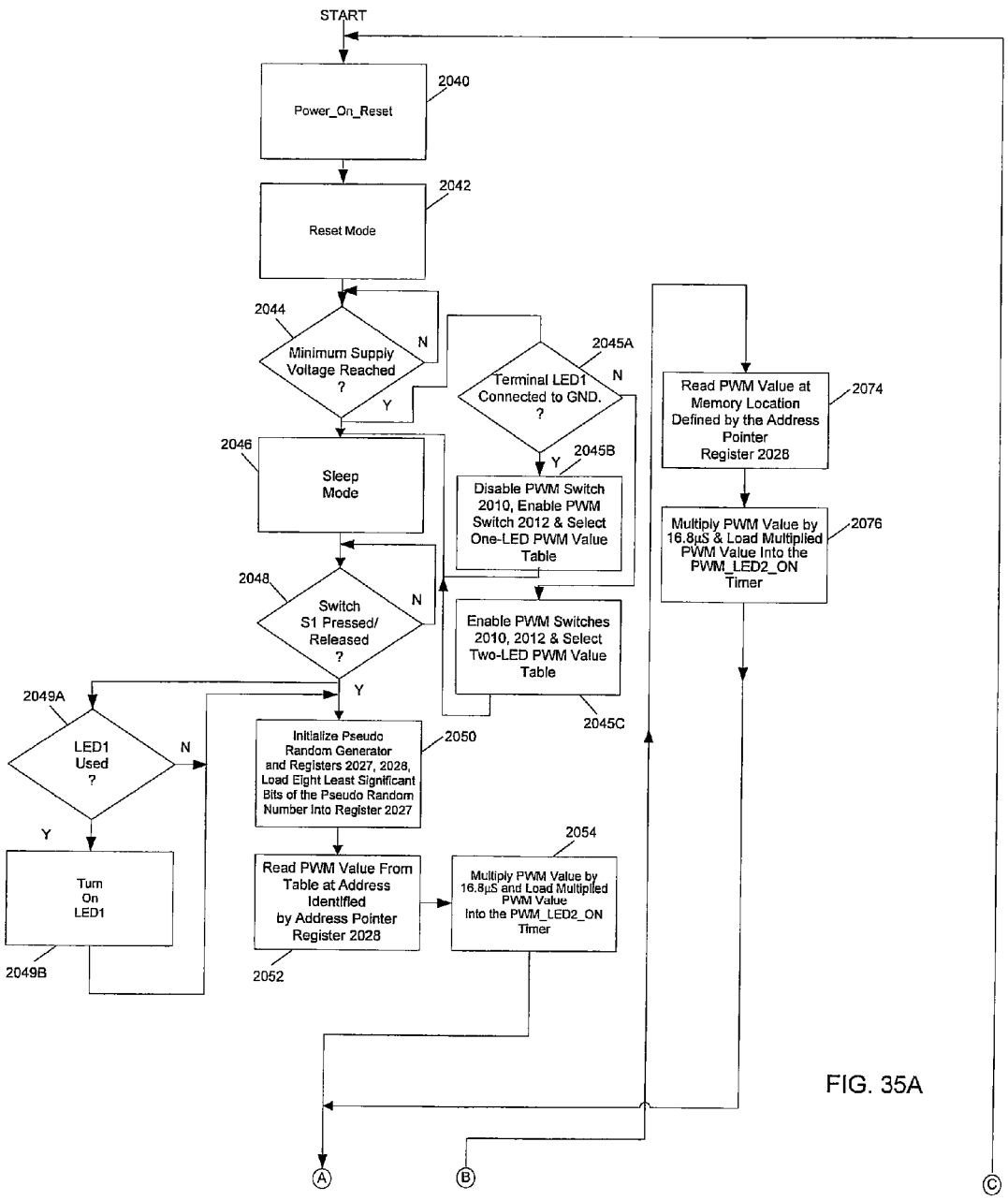
FIGS. 35A and 35B, when joined along the similarly lettered lines, together illustrate programming executed by the logic of FIG. 32 to control one or two LED's.
Figure 35B:
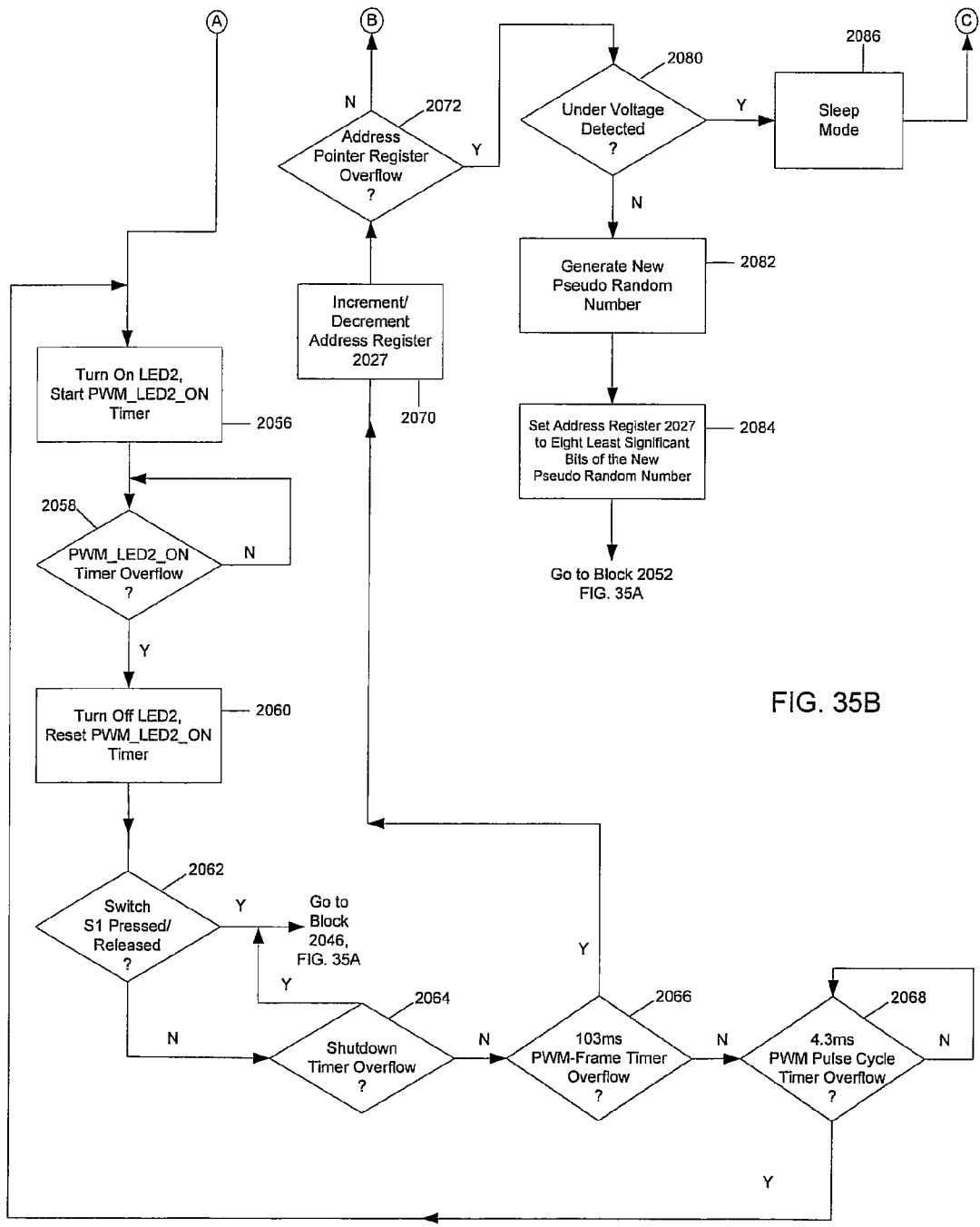

Referring next to the flowchart of FIGS. 35A and 35B, which illustrate the overall operation of the ASIC 2000 in accordance with the waveforms of FIG. 34 (with the exception of the bottom three waveforms thereof), control begins at a block 2040, which checks to determine when a POWER-ON RESET signal has been developed. This signal is generated when batteries are first placed into the active material emitting device, or when dead batteries are replaced with charged batteries, or when charged batteries are removed from the device and are returned to the device and a minimum supply voltage has been reached.

Control then passes to a block 2042, which implements a reset mode of operation whereby all internal registers are set to define start-up values and all timers are reset. A block 2044 then checks to determine whether a minimum supply voltage has been reached and, when this is found to be the case, control passes to a block 2045A, which checks to determine whether the terminal LED 1 is connected to ground potential.

If this is found to be the case, a block 2045B disables the PWM switch 2010, enables the PWM switch 2012, and selects a particular table of the PWM value tables 2004 corresponding to single LED operation for subsequent accessing. On the other hand, if the block 2045A determines that the terminal LED1 is not connected to ground (i.e., the terminal is coupled to LED1) control bypasses the block 2045B and proceeds to a block 2045C, whereupon both PWM switches 2010 and 2012 are enabled and a different table of the PWM value tables 2004 corresponding to two LED operation is selected for later accessing. Control from the blocks 2045B and 2045C passes to a block 2046, which then implements a sleep mode of operation. During operation in the sleep mode, all internal components of the ASIC 2000 are deactuated, with the exception of the debouncer, which remains active to determine when the switch S1 is momentarily depressed for greater than the particular period of time.

Following the block 2046, control pauses at a block 2048 until a determination has been made that the switch S1 has been momentarily depressed and released. When this action is detected, and it has been determined that the terminal LED1 is not connected to ground, a block 2049B turns LED1 on in the fashion described above so that such LED appears to be continuously energized. Conversely, if it has been determined that the terminal LED1 is connected to ground, the block 2049B is skipped. Control then passes to a block 2050, which initializes the pseudo random generator 2002 of FIG. 33 and causes the pseudo random generator 2002 to develop a sixteen-bit pseudo random number at the output of the shift register SR of FIG. 33 of which the eight least significant bits are loaded into the address register 2027 of FIG. 32. This loading, in turn, causes the address pointer register 2028 to develop a six-bit number corresponding to the eight-bit pseudo random number loaded into the register 2027 as described above.

Following the block 2050, a block 2052 reads one of 64 PWM values stored in the selected table of the PWM value tables 2004 of FIG. 32. In general, the PWM values stored in the selected PWM value table define duty cycles for LED2. Preferably, PWM values that are stored in adjacent locations in the selected table have no particular relationship with one another (i.e., the PWM values in adjacent storage locations vary in a random or pseudo random manner from one another), although this need not be the case. In any event, the block 2052 reads the PWM value from the selected table stored at the address identified by the six-bit current output value of the address pointer register 2028. A block 2054 then multiplies the PWM value read by the block 2052 by a particular length of time, such as 16.8 microseconds, and loads that multiplied PWM value into a PWM-LED2_ON timer implemented as a part of the timers 2006 of FIG. 32.

Following the block 2054, a block 2056 of FIG. 35B, turns on LED2 and starts the PWM-LED2_ON timer and also initializes and starts 103 msec. and 4.3 msec. timers. Assuming at this point that the batteries 640 are fully charged, the charge pump portion of the circuit 2008 is inactive. Control then pauses at a block 2058 until the PWM-LED2_ON timer 2006 experiences an overflow condition. When this overflow condition occurs, a block 2060 turns off LED2 for the balance of the 4.3 millisecond pulse cycle and resets the PWM-LED2_ON timer. Control then passes to a block 2062 which determines whether the switch S1 has been momentarily pressed and released. If not, a block 2064 determines whether the shut down timer that measures the auto shut-off delay period has experienced an overflow condition. If this is also not the case, a block 2066 checks to determine whether a 103 millisecond PWM-frame timer implemented as a part of the timers 2006 of FIG. 32 has experienced an overflow condition. If this is further not the case, control remains with a block 2068 until a 4.3 millisecond PWM pulse cycle timer also implemented as a part of the timers 2006 experiences an overflow condition, whereupon control returns to the block 2056 to begin the next 4.3 millisecond PWM pulse cycle.

If the block 2062 determines that the switch S1 has been momentarily pressed and released, or if the block 2064 determines that the shut down timer has experienced an overflow condition, control returns to the block 2046 of FIG. 35A whereupon the sleep mode is entered.

If the block 2066 determines that the 103 millisecond PWM-frame timer has overflowed, control passes to a block 2070, which either increments or decrements the address register 2027. The decision to increment or decrement the address pointer is determined by the most significant bit of the sixteen-bit pseudo random number developed by the pseudo random generator 2002. A zero as the most significant bit causes the block 2070 to decrement the address register 2027, whereas a one as the most significant bit causes the block 2070 to increment the address register 2027. If desired, the decision to increment or decrement may be based upon another bit of the pseudo random number, or a zero in a particular bit position may cause the block 2070 to increment the address register 2027 while a one in the particular bit position may cause the block 2070 to decrement the address register 2027. As a still further alternative, the block 2070 may only decrement or only increment the address register 2027 for each pseudo random number developed by the generator 2002 regardless of the values of the bits of the pseudo random number. Still further, the particular bit that determines whether to increment or decrement may vary from number-to-number developed by the generator 2002. In any event, the address pointer may be incremented when a particular pseudo random number has been developed by the generator 2002 and the address pointer may be decremented (or incremented, for that matter) when a subsequent pseudo random number is developed by the generator 2002.

Following the block 2070, a block 2072 checks to determine whether the address pointer register 2028 has experienced an overflow condition. Specifically, because 64 values are stored in the selected table of the tables 2004, the block 2072 checks to determine whether the incrementing or decrementing of the address pointer 2070 has caused the address pointer register 2028 to increment to a value of 0000010 or to decrement to a value of 111111. If this is not the case, a block 2074 reads the PWM value at the next memory location (either above or below the previous memory location) defined by the current value of the address pointer register 2028. A block 2076 multiplies the PWM value stored at the memory location with the particular length of time (i.e., 16.8 microseconds) and loads the multiplied value into the PWM-LED2_ON timer and control passes to the block 2056 of FIG. 35B to start a new 4.3 millisecond pulse cycle.

If the block 2072 determines that the address pointer register 2028 has experienced an overflow condition, a block 2080 checks to determine whether an under voltage condition has been detected whereby the battery voltage has fallen below a particular level of, for example, 1.8 volts. If this is found to be the case, control passes to a block 2086 that causes the ASIC 2000 to enter a low battery sleep mode of operation. The block 2086 maintains the ASIC 2000 in the low battery sleep mode until a power-on reset condition again occurs, for example, by replacing the discharged batteries with fully charged batteries. This action prevents the discharged batteries from being further discharged to a point where operation of the device can no longer be maintained or to a point where the batteries may leak and damage the device.

Figure 33:
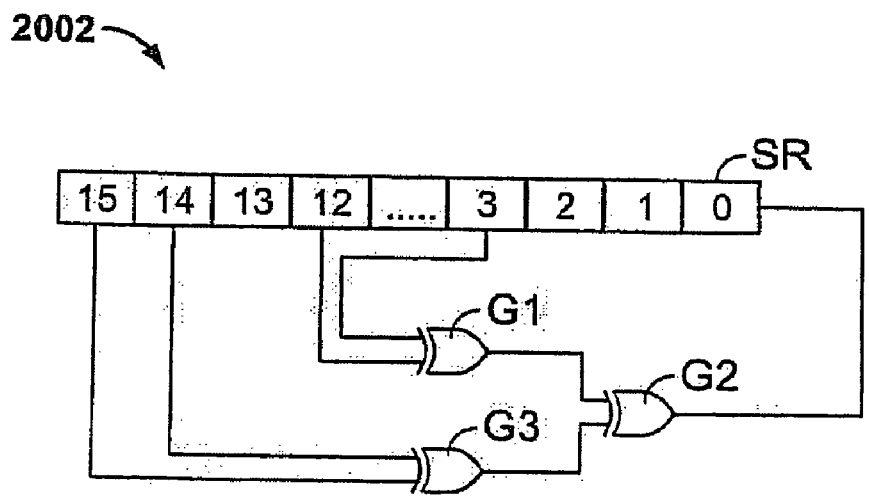
FIG. 33 is a schematic diagram functionally illustrating the random number generator implemented by the integrated circuit of FIG. 32.

If the block 2080 determines that the under voltage condition has not been detected, a block 2082 causes the pseudo random generator 2002 of FIG. 33 to generate a new sixteen-bit pseudo random number and the address register 2027 is loaded with the eight least significant bits of this new number by a block 2084. Control then passes to the block 2052 FIG. 35A.

In the case where LED1 is used, the foregoing methodology of ignoring two of the eight bits of the pseudo random number when addressing the selected table results in a pattern of repetitively addressing two consecutive memory locations in the table 2004 a total of four times. That is, in the example where the pseudo random number is 00000000 and the block 2070 is incrementing, the memory location addressing scheme proceeds as follows:

| 000000 | 000010 | 000100 |
|--------|--------|--------|
| 000001 | 000011 | 000101 |
| 000000 | 000010 | 000100 |
| 000001 | 000011 | 000101 |
| 000000 | 000010 | 000110 |
| 000001 | 000011 | 000111 |
| 000000 | 000100 | . |
| 000001 | 000101 | . |
| 000010 | 000100 | . |
| 000011 | 000101 | |

The foregoing addressing scheme when both LED1 and LED2 are used results in a flickering effect while that is visually pleasing while allowing the use of a relatively small PWM value table for the two LED mode of operation. This, in turn, reduces the cost of the ASIC 2000. It should be noted that the single LED mode of operation does not result in the repetitive addressing scheme noted above; rather, in this case, incrementing and decrementing occur directly through the selected table.

Referring again to FIG. 32, the ASIC 2000 includes a terminal ILIM in addition to the terminals CSLOW and GDRV that are connected to external circuitry to implement the active material dispenser. Specifically, a capacitor C4 is connected between the terminal ILIM and ground. A pair of inductors L2 and L3 and a piezoelectric element 3000 are connected in series with one another across the capacitor C4. A gate electrode of a transistor Q1 is coupled to the terminal GDRV and source and drain electrodes of the transistor Q1 are coupled to a tap of the inductor L2 and ground, respectively. A further capacitor C5 is coupled between the terminal CSLOW and ground.

Figure 36:
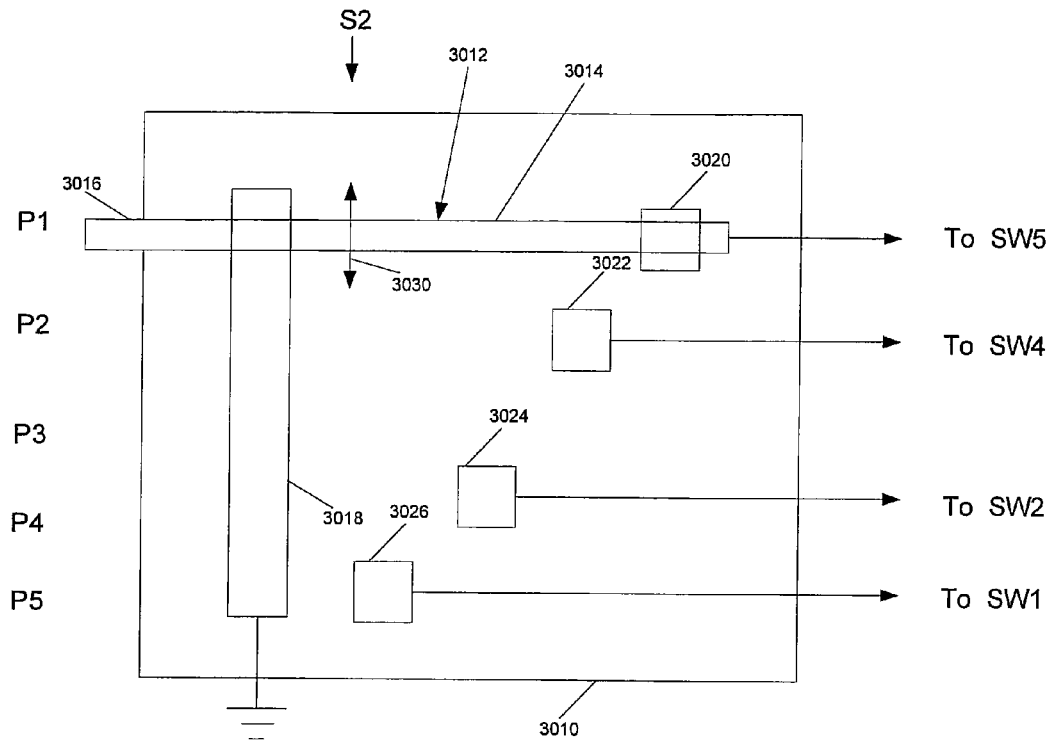
FIG. 36 is a diagrammatic view of the switch S2 of FIG. 32.

The system logic 2026 continuously operates the active material dispenser if the terminal GDRV is not connected to ground. (This determination, as well as the determination of whether LED1 is coupled to the ASIC 2000 is performed by a detector 3002, FIG. 32.) The operation of the active material dispenser is independent of the operation of the LED(s). A rate selector switch S2 (that preferably comprises the switch 583 of FIG. 20) provides inputs to terminals SW1, SW2, SW4, and SW5 that together determine the duration of the dwell periods between discharges of the active material dispenser. Specifically, as seen in FIG. 36, the rate selector switch S2 is diagrammatically shown as including a housing 3010, a movable switch contact 3012 having an internal electrically conductive wiper 3014 and an externally-disposed slide button 3016. A first electrically conductive trace 3018 extends fully at least along a series of first through fourth switch positions P1-P4, and possibly extends as shown to a fifth switch position P5. The first trace 3018 is electrically connected to ground potential. Second through fifth electrically conductive traces 3020, 3022, 3024, and 3026, are connected to terminals SW5, SW4, SW2, and SW1, respectively, of the ASIC 2000. The terminals SW1, SW2, SW4, and SW5 have internal, controllable pull-ups and pull-downs. When the ASIC 2000 is in the sleep mode, these terminals are all pulled down. Conversely, when the ASIC 2000 is checking the status of the signals provided to these terminals, the terminals SW1, SW2, SW4, and SW5 are pulled up internally. The rate selector switch S2 pulls down one of these terminals depending upon the position P1-P5 that the switch contact 3012 is moved to. When the switch contact 3012 is in the position P1 as illustrated in FIG. 36, the terminal SW5 is pulled down to ground potential, and the ASIC 2000 establishes the dwell time at a first value, such as 5.75 seconds. When the switch contact 3012 is moved in the direction of the arrow 3030 to any of the positions P2, P4, and P5 one of the terminals SW4, SW2, or SW1, respectively, is pulled down to ground potential, and the ASIC 2000 establishes the dwell time at other values, such as 7.10, 12.60 or 22.00 seconds, respectively. When the switch contact 3012 is moved to the position P3, none of the terminals SW1, SW2, SW4, and SW5 is pulled down to ground potential, and the ASIC 2000 establishes the dwell time at a further value, such as 9.22 seconds. In the event that more than one of the terminals SW1, SW2, SW4, and SW5 is coupled to ground at any particular time due to a switch malfunction, the dwell time is preferably established at a mid-range value, such as 9.22 seconds.

Figure 37:
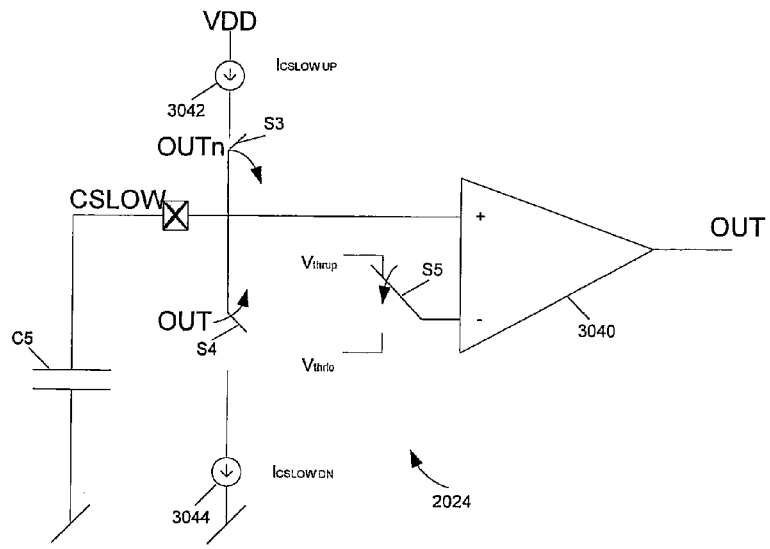
FIG. 37 is a schematic diagram functionally illustrating operation of the ramp oscillator of FIG. 32.
Figure 38:
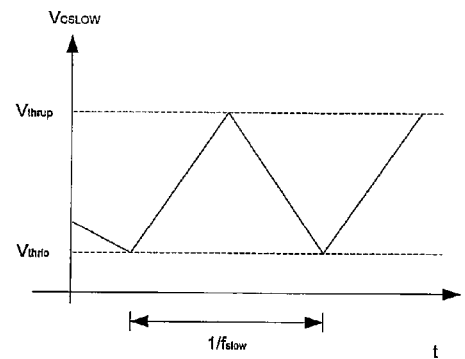
FIG. 38 is a waveform diagram illustrating the voltage developed at the terminal CSLOW of FIG. 32.

The ramp oscillator 2024 obtains the output of the clock oscillator 2016 and develops the ramp voltage on the terminal CSLOW, as noted above. The ramp oscillator 2024 continuously runs if the detector 3002 determines that the terminal GDRV is connected to other than ground potential, and the output of the ramp oscillator 2024 acts as a clock to control the pumping frequency (in accordance with the setting of the switch S2) and the pump duration. Preferably, the pump duration is established at a constant value of about 11 milliseconds. The frequency of the ramp oscillator 2024 is determined by the size of the capacitor C4 and the charging/discharging current for the capacitor C4 is obtained from a bias current generated by the ASIC 2000. The bias current is trimmed in order to meet the frequency tolerance requirements of the ramp oscillator 2024. FIG. 37 functionally illustrates the ramp oscillator 2024 as comprising an op amp 3040 connected in a comparator configuration and having a noninverting input coupled to the capacitor C5 and further coupled to switches S3 and S4. The switches S3 and S4 are operated in antiphase relationship each with a 50% duty cycle to alternately connect constant current sources 3042 and 3044 to the capacitor C5. An inverting input of the op amp 3040 is coupled to a switch S5, which alternately connects voltages $V_{thrup}$ and $V_{thrlo}$ to the inverting input. FIG. 38 illustrates the resulting voltage $V_{CSLOW}$ developed at the terminal CSLOW of the ASIC 2000. The voltage $V_{CSLOW}$ linearly ramps up and down between limits $V_{thrup}$ and $V_{thrlo}$ with a period equal to $1/f_{slow}$ where $f_{slow}$ is the frequency of the waveform developed by the clock oscillator 2016, typically about 1000 Hz.

The capacitor C4 is charged by a constant current source 3050 (FIG. 32, labeled "Ilimiter"). The constant current source 3050 is switched off in a slowly decreasing manner when the voltage VDD is outside a regulated range thereof.

The VCO 2023 is controlled by the ramp voltage developed by the ramp oscillator 2024 during a pumping operation such that the frequency of the drive voltage developed at the terminal GDRV increases from a lower value to an upper value.

Figure 39:
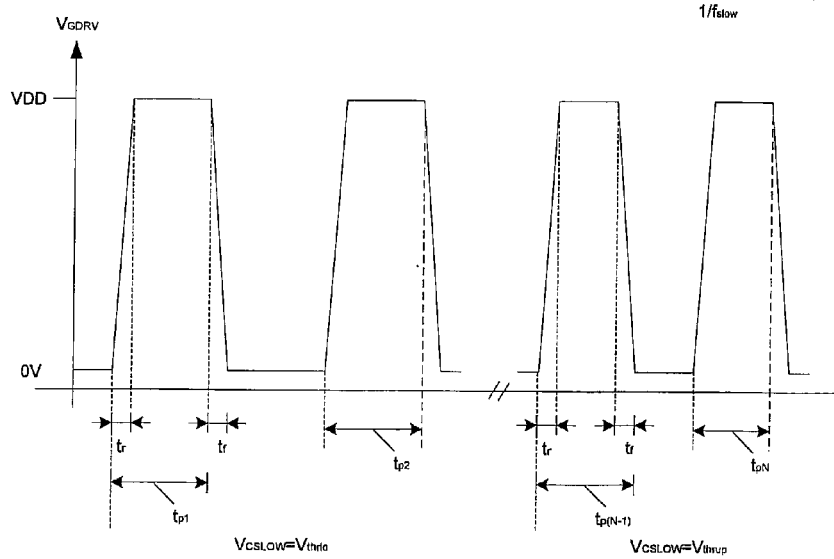
FIG. 39 is a waveform diagram illustrating the voltage developed at the terminal GDRV of FIG. 32.

This operation is illustrated in the waveform diagram of FIG. 39, which illustrates that the VCO output voltage comprises a series of pulses each having rise and fall times $t_r$ and $t_f$, respectively, and pulse-widths $t_{p1}, t_{p2}, \ldots, t_{p(N-1)}, t_{pN}$, each measured from the beginning of a rise time to the beginning of a fall time of the pulse. The frequency of the VCO output voltage linearly increases from a first frequency $f_{low}$ to a second frequency $f_{high}$, where $f_{low}$ is preferably equal to about 130 kHz and $f_{high}$ is preferably equal to about 160 kHz. Also preferably, the duty cycle is maintained at about 33% throughout the variation in VCO output voltage frequency.

Figure 40:
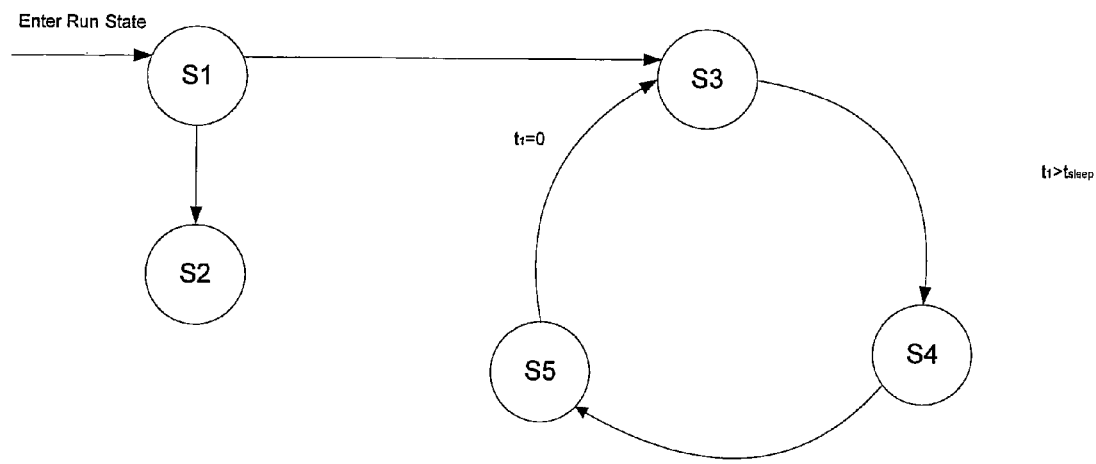
FIG. 40 is a state diagram illustrating operation of the integrated circuit of FIG. 32 to control an active material dispenser.

Referring next to the state diagram of FIG. 40, when a power-on-reset condition is sensed, all of the internal registers of the ASIC 2000 (including registers that are used for operation of the LED(s)) are set to defined start up values and the ASIC 2000 enters a state S1. While in the state S1 the logic 2026 (FIG. 32) checks to determine if the terminal GDRV is coupled to ground. If so, the shut down timer implemented as part of the timers 2006 of FIG. 32 is set to four hours and control passes to a state S2, at which the active material dispenser functionality is disabled. On the other hand, if the logic 2026 determines that the terminal GDRV is not coupled to ground, the fragrance dispenser is functionality enabled, and control passes to a state S3 comprising a fragrance sleep mode of operation. As control passes to the state S3, the terminals SW1, SW2, SW4, and SW5 are pulled up and a duration for the fragrance sleep mode is read in by establishing the position of the switch S2. During the fragrance sleep mode of operation, the terminal GDRV is pulled down to a low voltage level, the VCO 2023 is disabled, and the terminals SW1, SW2, SW4, and SW5 are pulled down.

Once the fragrance sleep mode duration has elapsed, the ASIC 200 enters a state S4 where the terminal GDRV is maintained at a low voltage, the VCO 2023 is powered up, the terminals SW1, SW2, SW4, and SW5 are pulled up and read, and the under voltage detector 2020 is checked. The ASIC 2000 then enters a state S5 during which the active material dispenser is energized in accordance with the setting of the switch S2 for 11 milliseconds, as described above The ASIC 2000 remains in the state S5 until the 11 milliseconds have elapsed and thereafter re-enters the sleep mode at state S3. Control then continues to cycle among the states S3, S4, and S5 until the under voltage detector 2020 determines that the battery voltage drops below a particular level, at which time the active material dispenser functionality is disabled until another power-on-reset condition is sensed, whereupon control reverts to the state S1 and the foregoing operation is again undertaken.

It should be noted that at all times other than during a pumping operation the VCO 2023 is maintained in an off condition.

Figure 41:
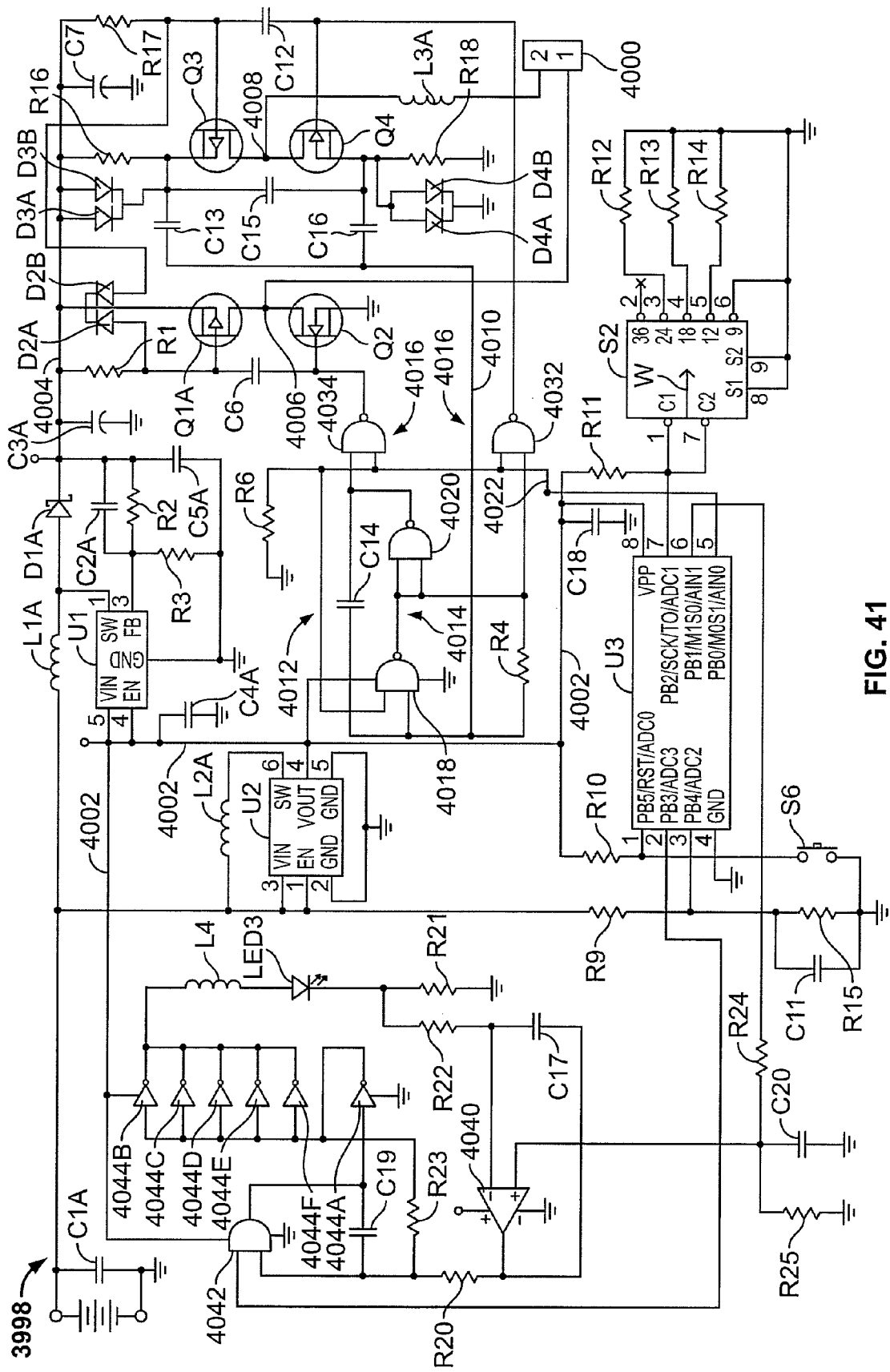
FIG. 41 is a schematic diagram of a further circuit according to the present invention for controlling an LED and an active material emission device.

FIG. 41 illustrates a circuit 3998 for controlling a piezoelectric actuator 4000 and a light emitting diode LED3. The circuit includes a programmable integrated circuit U3, which may be in the form a microprocessor of the type ATTINY 13V-10331 manufactured by Atmel. The microprocessor U3 may be programmed in accordance with the flowchart of FIGS. 35A, 35B to operate in the various modes and to obtain a flickering effect of LED3, with the exception that the microprocessor U3 does not include the capability to operate multiple LED's independently. Accordingly, in the illustrated embodiment the microprocessor U3 also lacks the ability to determine if multiple LED's are connected thereto, although the microprocessor can be programmed to include these capabilities, if desired.

The microprocessor U3 may also be programmed to read a switch S2, which may comprise the rate selector switch 583 of the embodiment of FIGS. 15A-24, and operate the piezoelectric actuator 4000 generally in accordance with the state diagram of FIG. 40 so that the various operational modes described in connection therewith are implemented. As described in greater detail hereafter, the piezoelectric actuator 4000 forms a part of a resonant circuit that is operated at a resonant frequency by the microprocessor U3.

An example of a piezoelectric actuator drive circuit that is operated at a resonant frequency is disclosed in Blandino et al. U.S. application Ser. No. 11/464,419, filed Aug. 14, 2006, entitled "Drive Circuits and Methods for Ultrasonic Piezoelectric Actuators," the disclosure of which is hereby incorporated by reference herein.

Specifically, the microprocessor U3 is, in turn, responsive to the setting of the rate selector switch S2, which can be set to one of five settings. A wiper W of the switch S2 can be connected to one of five pins 2-6 of the switch S2. The pin 2 is disconnected from all sources of potential whereas pins 3-5 are connected to three resistors R12, R13, and R14 forming a voltage divider with a resistor R11. When the wiper W is connected to pin 2, the input to a pin 7 of the microprocessor through the resistor R11 is not divided. The pin 6 is coupled to ground potential. The setting of the switch S2 determines the duration of a dwell period during which the piezoelectric actuator is not actuated. The dwell periods are separated by emission sequences preferably of fixed duration. Preferably, the emission sequence is about 12 mS in length and the dwell periods are selectable to be about 5.75 seconds, 7.10 seconds, 9.22 seconds, 12.60 seconds, or 22.00 seconds in length. In other embodiments, these dwell periods are selectable to be about 9.22 seconds, 12.28 seconds, 17.92 seconds, 24.06 seconds, or 35.84 seconds in length or 5.65 seconds, 7.18 seconds, 9.23 seconds, 12.81 seconds, or 22.54 seconds in length. Any emission sequence duration and any dwell period durations could be used and the number of selectable dwell period durations and multiple selectable emission sequence durations of any number could be implemented. The pin 7 of the microprocessor U3 is coupled to the wiper W and is further coupled by the resistor R11 to a line 4002 that receives a voltage VPP developed by a voltage regulator U2 and provided to a pin 8 of the microprocessor U3. The pin 8 of the microprocessor U3 is further coupled by a capacitor C18 to ground potential. The voltage on the pin 7 of the microprocessor U3 is sensed by an internal A/D converter of the microprocessor to read the setting of the switch S2.

Alternatively, the dwell period(s) may be predetermined to be anywhere in a range from 12 mS up to 30 minutes or longer. For example in a boost mode (which may be selected by a switch (not shown)), when it is desired to release a large amount of fragrance, each emission sequence could be 12 mS and each dwell period could be 12 mS in duration to achieve a 50% duty cycle. On the other extreme, when the room in which the volatile dispensing device is located is unoccupied (for example, as detected by a motion sensor or other sensor (not shown)) it might be desirable to emit volatile for a 12 mS duration once every 30 minutes just to maintain some volatile in the room. As noted in greater detail hereinafter, this periodic emission of volatile at a selectable rate may be overridden by a command to emit volatile at an accelerated rate on a periodic or aperiodic basis.

A pin 1 of the microprocessor U3 is coupled by a resistor R10 to the regulated voltage developed on the line 4002 developed by the voltage regulator U2. A switch S6 is further coupled between the pin 1 of the microprocessor U3 and ground potential, wherein the switch S6 may comprise the switch 583 of the embodiments of FIGS. 15A-24. A pin 3 of the microprocessor U3 is coupled by a resistor R9 to a DC source 4003, which may comprise two series-connected 1.5 volt AA alkaline batteries. Also, a parallel combination of a resistor R15 and a capacitor C11 is coupled between the pin 3 of the microprocessor U3 and ground potential. A pin 4 of the microprocessor U3 is coupled to ground potential.

The voltage regulator U2 is coupled to the DC source 4003 and preferably develops a regulated voltage of 3.3 volts. A further voltage regulator U1 and components L1A, D1A, C2A, C5A, R2 and R3 together produce a regulated voltage of preferably 12 volts on a line 4004. Capacitors C3A and C7 smooth the voltage on the line 4004.

The circuit 3998 further includes four transistors Q1A and Q2-Q4 coupled in a full-bridge configuration between the line 4004 and ground potential. The resonant circuit comprising an inductor L3A and the piezoelectric actuator 4000 is coupled across junctions 4006, 4008 between drain electrodes of the transistors Q1A, Q2 and Q3, Q4, respectively. Resistors R1 and R17 are coupled between the line 4004 and gate electrodes of the transistors Q1A and Q3, respectively. Capacitors C6 and C12 are coupled between the gate electrodes of the transistors Q1A, Q2 and Q3, Q4, respectively.

First and second current sensors in the form of resistors R16 and R18 are coupled between source electrodes of the transistors Q3 and Q4, respectively, and the line 4004 and ground potential, respectively. Feedback capacitors C13, C15, and C16 are coupled between the source electrodes of the transistors Q3 and Q4 and a feedback line 4010. A feedback signal developed on the feedback line 4010 is AC coupled and phase shifted for proper operation of a control circuit 4012.

The control circuit 4012 includes an amplifying and inverting circuit 4014 and a driver circuit 4016. The amplifying and inverting circuit 4014 includes first and second NAND gates 4018, 4020, respectively. The first NAND gate 4018 is biased into a linear range of operation by a negative feedback resistor R4 to operate as an amplifier and the second NAND gate 4020 is used as an inverter. A first input of the first NAND gate 4018 receives a gating or enable signal developed on a line 4022 developed at a pin 5 of the microprocessor U3. The line 4022 is coupled by a resistor R6 to ground potential. A second input of the first NAND gate 4018 receives the signal on the feedback line 4010.

When power is supplied to the microprocessor U3 by the DC source 4003 the microprocessor U3 periodically develops an approximate 12 mS gating or enable signal at the pin 5. The gating or enable signal is delivered to the first input of the NAND gate 4018. An output of the NAND gate 4018 is coupled to first and second inputs of the NAND gate 4020 and an output of the NAND gate 4020 is coupled by a capacitor C14 back to the second input of the NAND gate 4018. The capacitor C14 supplies a small amount of positive feedback to promote stable transitions. The output of the NAND gate 4018 is coupled to a first input of a third NAND gate 4032 and the output of the NAND gate 4020 is coupled to a first input of a fourth NAND gate 4034, wherein the NAND gates 4032, 4034 together comprise the driver circuit 4016. Second inputs of the NAND gates 4032, 4034 receive the gating or enable signal on the line 4022. The control circuit 4012 causes the NAND gates 4032, 4034 to drive the pairs of transistors Q1A, Q2 and Q3, Q4 by providing drive signals to the gate electrodes thereof. In this regard, the NAND gate 4020 acts as an inverter to invert the output of the NAND gate 4018 so that the transistors Q1A and Q2 are driven 180° out of phase with respect to the transistors Q3 and Q4. That is, the transistors Q1A and Q4 are first turned on while the transistors Q2 and Q3 are held in an off condition, and subsequently the transistors Q1A and Q4 are turned off and the transistors Q2 and Q3 are turned on. The sequence of conduction then repeats. Preferably, the transistors are operated at about 50% duty cycle. If desired, a period of time may be interposed between turn-off of one pair of transistors and turn-on of another pair of transistors during which all transistors are briefly turned off to prevent cross-conduction. In any event, the current through the piezoelectric actuator 4000 alternates at a selected resonant frequency thereof during each gating period (i.e., during the times that the gating or enable signal is developed) dependent upon the impedance of the resonant circuit comprising the inductor L3A and the piezoelectric actuator 4000. This oscillation occurs in a continuous fashion during each approximate 12 mS emission sequence, following which the microprocessor U3 terminates the gating or enable signal on the pin 5 thereof, thereby turning off the transistors Q1A-Q4 and terminating further emission of active material by the piezoelectric actuator 4000.

When a user wishes to activate the circuitry during operation referred to as a "boost" mode, the user depresses a switch (not shown) coupled to the microprocessor U3. This action causes the microprocessor U3 to develop the gating or enable signal on the pin 5. In one embodiment, the gating signal is periodically or aperiodically developed during an interval. For example, the gating signal may cause volatile emission comprising one 12 mS pulse every second for 83 or 84 seconds. As another example, the gating or enable signal may cause volatile emission comprising a group of ten 12 mS pulses spaced apart from one another by 72 mS, wherein successive groups of ten 12 mS pulses take place at intervals of 60 seconds. This sequence may continue for any length of time. As should be evident, any number of pulses of any duration can be periodically or aperiodically emitted at any desired frequency (if periodic) and over one or more intervals of any length, as desired. In yet another embodiment, the gating or enable signal is developed for as long as the switch S6 is depressed so that volatile is emitted in a continuous fashion during the entire time that the switch S6 is depressed. In any event, the piezoelectric actuator 4000 oscillates at the particular resonant frequency during the entire time that the gating signal is developed, although the actuator 4000 may be intermittently actuated during the time that the gating or enable signal is developed, if desired.

A pair of diodes D3A, D3B are provided to limit the maximum voltage across the resistor R16 and a pair of diodes D4A, D4B limit the maximum voltage across the resistor R18. Limiting the maximum voltage across the current sensing resistors R16, R18 increases the efficiency of the circuit. Furthermore, the circuit 3998 includes first and second level shifting circuits to convert the 0-3.3 volt drive signal from the control circuit 4012 to approximately 9.3-12.3 volts to properly drive the transistors Q1A and Q3. A combination of a diode D2A, resistor R1, and capacitor C6 forms the first level shifting circuit and a combination of a diode D2B, resistor R17, and capacitor C112 forms the second level shifting circuit.

The microprocessor U3 develops a pulse width modulated (PWM) waveform at a pin 6 that is supplied through a resistor R24 to a non-inverting input of an operational amplifier (op amp) 4040. The non-inverting input is further coupled by a parallel combination of a resistor R25 and a capacitor C20 to ground potential. The resistor R25 and the capacitor C20 together with the resistor R24 comprise a voltage divider and filtering circuit. A first input of an AND gate 4042 receives a further gating or enable signal developed by the microprocessor U3 and a second input of the AND gate 4042 is coupled by resistor R20 to an output of the op amp 4040. A capacitor C19 is coupled between an output of the AND gate 4042 and the second input thereof. The output of the AND gate 4042 is further coupled by an inverter 4044A and a resistor R23 to the second input thereof. The AND gate 4042 together with the capacitor C19, the inverter 4044A, and the resistor R23 operate as an oscillator with positive feedback provided by the capacitor C19 and negative feedback supplied by the inverter 4044A and the resistor R23. This oscillator produces a PWM output that has a duty cycle varied by the output of the op-amp 4040. The AND gate 4042 receives the regulated 3.3 V power developed by the voltage regulator U2 and is further coupled to ground potential.

The PWM output of the inverter 4044A is further coupled to a series of five inverters 4044B-4044F that are coupled together in parallel and which together act as a drive circuit. An inductor L4 receives the combined outputs of the inverters 4044B-4044F in the form of a rectangular wave and smoothes the output voltage developed thereby to a substantially DC voltage level dependent on the duty cycle of the PWM output developed by the oscillator including AND gate 4042, capacitor C19, inverter 4044A, and resistor R23. The resulting waveform is applied to LED3, wherein the current amplitude delivered to LED3 determines the brightness thereof. A current sensing resistor R21 is coupled between LED3 and ground potential and a feedback signal is supplied to an inverting input of the op amp 4040 by a resistor R22 that is coupled to the junction between LED3 and the resistor R21. A capacitor C17 is coupled between the inverting input of the op amp 4040 and an output thereof. The resistor R22, capacitor C17, and op amp 4040 together act as an integrator that samples the voltage across resistor R21 and uses negative feedback to force the sampled voltage at the inverting input of the op amp 4040 to equal the voltage delivered to the non-inverting input thereof as developed by the microprocessor U3, the resistors R24 and R25, and the capacitor C20. The resulting output of the op-amp 4040 is a varying DC voltage level that causes LED3 to flicker. The microprocessor U3 implements a pseudo-random number generator and further stores PWM values in memory locations similar or identical to the programming illustrated in FIGS. 35A and 35B to produce the waveforms as seen in FIG. 34.

In an alternative embodiment (not shown), a microprocessor or ASIC may include a digital to analog converter, which can supply a DC drive signal to the integrator along with the feedback signal developed across the resistor R21. In this embodiment, the filtering circuit including resistors R24, R25 and capacitor C20 may be omitted.

The inverters 4044A-4044F may be provided as a single integrated circuit and together comprise a low resistive output device that reduces on-resistance losses.

The oscillator comprising the AND gate 4042, the capacitor C19, the resistor R23 and the inverter 4044A differs from known oscillators in that known oscillators utilize two inverter sections with a positive feedback applied across both sections and a negative feedback applied across one section.

The oscillator in FIG. 41, on the other hand, generates a PWM signal utilizing a non-inverting section and an inverting section with positive feedback applied across the non-inverting section and negative feedback applied across both the inverting and non-inverting sections. In the preferred embodiment, the capacitor C19 provides the positive feedback and the resistor R23 provides the negative feedback. The use of positive capacitive feedback and negative resistive feedback in this manner results in an oscillator that is more stable when switching between high and low states and prevents or substantially prevents unwanted oscillations at transitions between states. The frequency of oscillation is determined by the equivalent RC time constant as determined by the values of the capacitor C19 and the parallel combination of the resistors R23 and R20.

The time constant of the integrator formed by the op amp 4040, the resistor R22 and the capacitor C17 preferably dominates the feedback loop to prevent instability of the circuit.

The rectangular waveform delivered to the inductor L4 switches between ground potential and 3.3V at several hundred kilohertz. The inductor L4 smoothes the rectangular waveform into an approximately constant waveform. The LED turn on voltage is approximately 1.9 volts; therefore, the PWM duty ratio of the oscillator output cannot exceed approximately 57% (i.e., 1.9/3.3) at the maximum brightness level so that LED3 is not overdriven. The current limiting feature afforded by the inductor L4 eliminates the need for a current limiting resistor that would simply dissipate the difference between the supply voltage of 3.3V and the turn on voltage of 1.9V of LED3. Such an approach using a current limiting resistor would reduce the efficiency of the circuit to 57% at best. The inductor L4 simply circulates the current into and out of the power supply and does not dissipate same, thereby improving efficiency. The voltage regulator U2 is approximately 95% efficient. The efficiency of the LED driver circuit of the illustrated embodiment approaches 95% as well, resulting in a total LED drive efficiency of 85%-90%.

Figure 42:
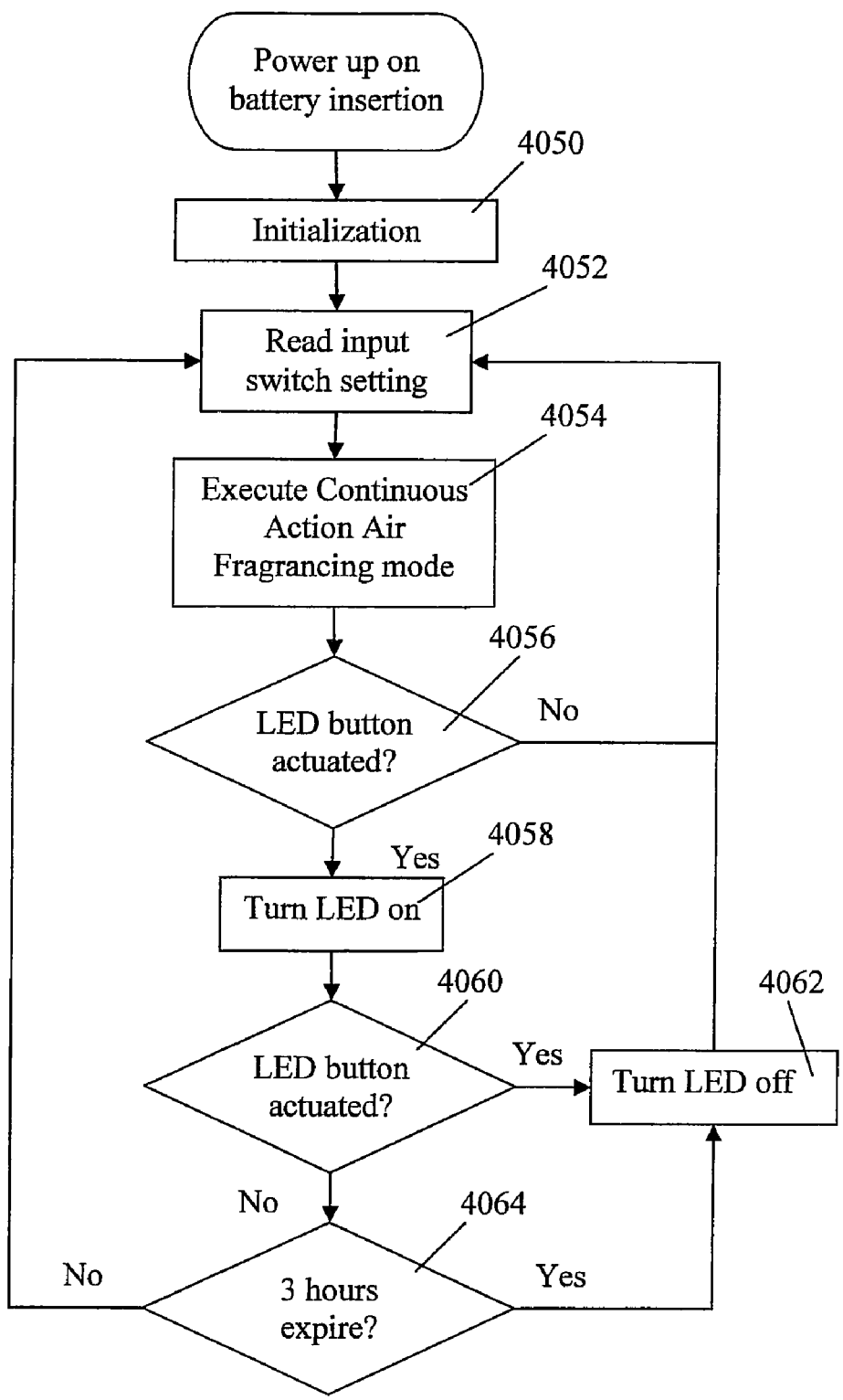
FIGS. 42 and 43 are flowcharts illustrating programming executed by the microprocessor of FIG. 41 to implement alternative embodiments of the present invention.

FIG. 42 illustrates programming executed by the microprocessor U3 to control the energization of the light emitting diode LED3 according to one embodiment. The programming begins following power up of the circuitry by the DC power source 4003 at a block 4050, which initializes various registers in the microprocessor U3. A block 4052 then reads the setting of the switch S2 and a block 4054 periodically or aperiodically actuates the piezoelectric actuator 4000 in accordance with the setting of the switch S2 as described above. A block 4056 then checks to determine whether the switch S6 has been momentarily actuated a first time. If this is not the case control returns to the blocks 4052 and 4054. Once the block 4056 determines that the switch S6 has been actuated a first time, a block 4058 energizes LED3 in accordance with the flickering sequence discussed above.

A block 4060 then checks to determine whether the switch S6 has been momentarily actuated a second time. If this is found to be the case, LED3 is turned off by a block 4062 and control returns to the block 4052. On the other hand, if the block 4060 determines that switch S6 has not been actuated, a block 4064 checks an internal timer of the microprocessor U3 to determine whether a particular period of time, such as three hours, has expired since the switch S6 was first momentarily actuated. If the particular period of time has not yet expired, control returns directly to the block 4052. However, if the block 4064 determines that the particular period of time has expired, control passes to the block 4062, which turns LED3 off and control returns to the block 4052.

Figure 43:
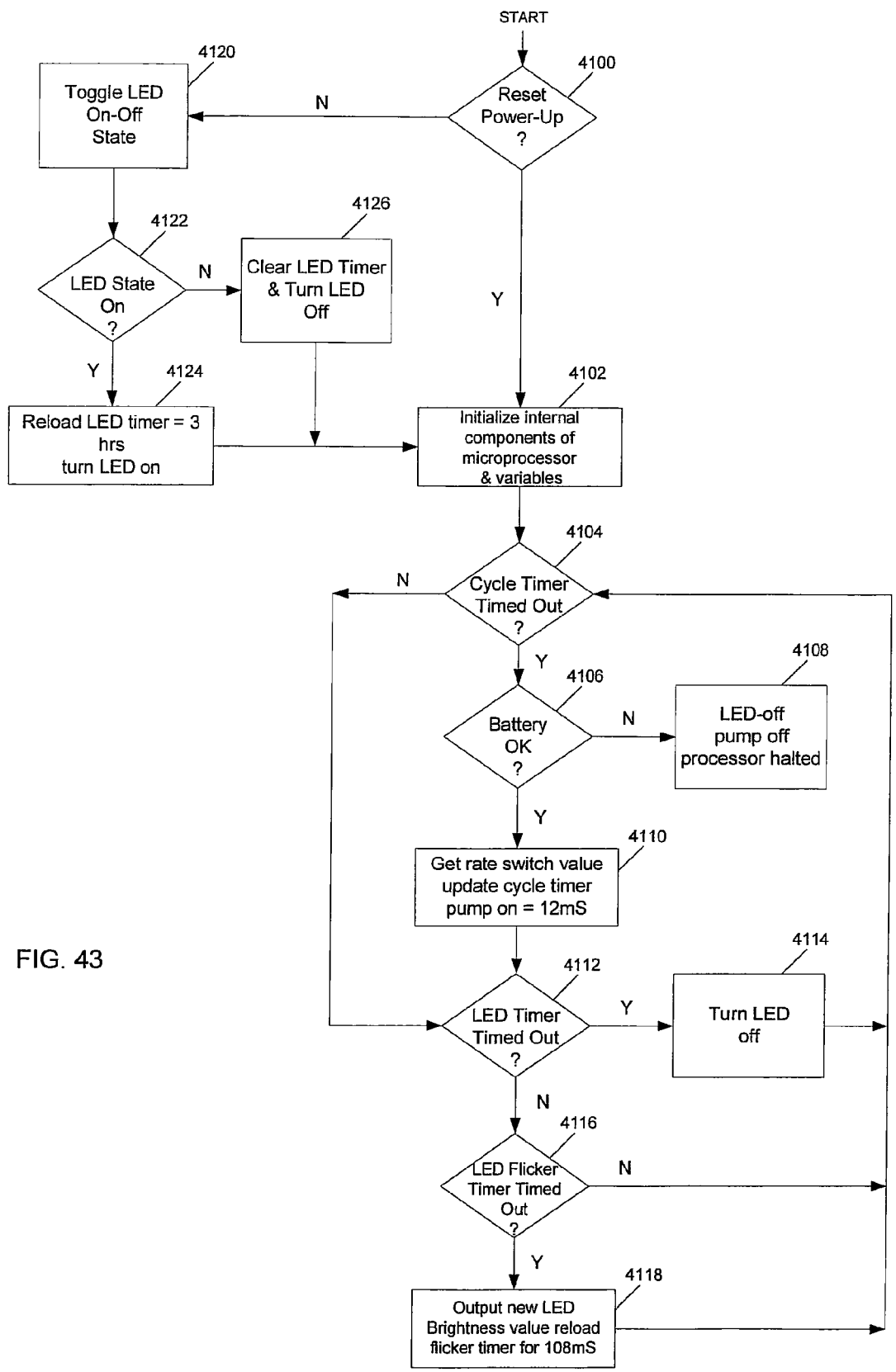

Referring next FIG. 43, a flowchart of programming executed by the microprocessor U3 is illustrated to implement an alternative embodiment. Control begins at a block 4100 which determines whether a power up reset has occurred caused by insertion of the batteries comprising the DC source 4003 or whether the switch S6 has been momentarily actuated. If control passed to the block 4100 due to a power up reset, a block 4102 initializes internal components as well as variables, timers, etc. in the microprocessor U3. In particular, the block 4102 initializes various internal components of the microprocessor U3 by, for example, setting up the processor clock, defining microprocessor pins as inputs or outputs, setting up an internal A/D converter (i.e., number of channels, conversion time, and A/D reference voltage), setting up the internal timer for the appropriate interrupt rate, initializing the PWM stage, etc. A block 4104 then checks to determine whether a cycle timer implemented by the microprocessor U3 has expired. The cycle timer determines the dwell period between actuations of the piezoelectric actuator 4000. If the cycle timer has expired, a block 4106 checks to determine whether the combined voltages of the batteries forming the DC source 4003 is greater than a predetermined level. If this is not found to be the case, a block 4108 turns off the LED and terminates further actuation of the piezoelectric actuator 4000. In addition, the microprocessor U3 is halted.

If the block 4106 determines that the combined battery voltages exceed a predetermined level, a block 4110 reads the position of the switch S2 and reinitializes the value of the cycle timer to a value determined by the position of the switch S2. The piezoelectric actuator is then actuated for a 12 mS emission sequence.

Following the block 4110, a block 4112 checks to determine whether an LED timer (described hereinafter) has expired. If this found to be the case, a block 4114 turns the LED off and control returns to the block 4104. On the other hand, if the LED timer has not expired, a block 4116 determines whether an LED flicker timer has expired. In the illustrated embodiment, the LED flicker timer measures 108 mS frame intervals during which the LED is provided a constant duty cycle PWM waveform (in general, as noted above, the duty cycles are different from frame interval to frame interval to obtain the flickering effect). If this is not found to be the case, control returns to the block 4104. Otherwise, a block 4118 causes the microprocessor U3 to output a new LED brightness value. This is accomplished in the manner described above in connection with FIGS. 35A and 35B by accessing a next or different portion of a memory containing brightness values. The block 4118 also reloads the flicker timer with a value corresponding to 108 mS and control returns to the block 4104.

If the block 4104 determines that the cycle timer has not expired, control by-passes the blocks 4106-4110 and proceeds directly to the block 4112. If control passed to the block 4100 due to momentary actuation of the switch S6, a block 4120 toggles a register indicating whether the LED is to be turned on or off. A block 4122 determines whether the LED is to be turned on, in which case a block 4124 reloads the LED timer with a value corresponding to a predetermined duration, such as three hours, and LED3 is turned on. Control then passes to the block 4104.

If the block 4122 determines that the LED is to be turned off, the LED timer is cleared and LED3 is turned off at a block 4126 and control passes to the block 4102.

INDUSTRIAL APPLICABILITY

The light and active material emitting device provides light and/or active material emitters. The device provides an overall desired aesthetic ambience in an area, such as a room.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

We claim:

1. A light and active material emitting circuit, comprising:
   an LED;
   a microprocessor that develops a pulse-width modulated (PWM) waveform;
   a first feedback circuit coupled to the LED;
   an integrator having a first input that receives the PWM waveform, a second input coupled to the first feedback circuit, and an output;

an oscillator coupled to the integrator including a logic gate, a first impedance coupled across the logic gate providing positive feedback and a second impedance coupled across the logic gate providing negative feedback;

a drive circuit coupled to the oscillator;

a first inductor coupled between the driver and the LED wherein the LED is caused to flicker;

a piezoelectric actuator;

a second inductor coupled to the piezoelectric actuator wherein the piezoelectric actuator and the second inductor form a resonant circuit;

a plurality of transistors coupled to the resonant circuit;

a second feedback circuit coupled to the plurality of transistors; and a control circuit coupled to the second feedback circuit and having an amplifier and an inverter, wherein the control circuit is further coupled to the transistors, and wherein the control circuit develops the drive waveforms such that the piezoelectric actuator is periodically driven at a resonant frequency.

2. The circuit of claim 1, wherein the amplifier is a first NAND gate and the inverter is a second NAND gate, and wherein the first NAND gate includes a first input that receives an enable signal developed by the microprocessor and a second input coupled to the second feedback circuit and the control circuit further includes a capacitor coupled between an output of the second NAND gate and the second input of the first NAND gate and further wherein the first NAND gate includes an output coupled to first and second inputs of the second NAND gate.

3. The circuit of claim 2, wherein the control circuit includes a third NAND gate having a first input coupled to the output of the second NAND gate, a second input that receives the enable signal, and an output coupled to the transistors and wherein a resistor is coupled between the second input of the third NAND gate and ground potential.

4. The circuit of claim 2, wherein two pairs of transistors are connected to the resonant circuit in a full-bridge configuration, and wherein the control circuit includes third and fourth NAND gates, the third NAND gate having a first input coupled to the output of the second NAND gate, a second input that receives the enable signal, and an output coupled to a first pair of the transistors and the fourth NAND gate having a first input coupled to the output of the first NAND gate, a second input that receives the enable signal, and an output coupled to a second pair of the transistors.

5. The circuit of claim 4, wherein a further resistor is coupled between the output and the second input of the first NAND gate.

6. The circuit of claim 5, wherein the feedback circuit includes another resistor that senses current flow through the resonant circuit and a capacitor coupling the other resistor to the first NAND gate.

7. The circuit of claim 1, wherein the oscillator generates a second PWM waveform that is controlled by the output of the integrator, and wherein the output of the integrator is controlled by the feedback circuit and the PWM waveform developed by the microprocessor.

8. A circuit for developing a drive waveform for an LED, comprising:

a microprocessor that develops a pulse-width modulated (PWM) waveform;

a feedback circuit coupled to the LED;

an integrator having a first input that receives the PWM waveform, a second input coupled to the feedback circuit, and an output;

an oscillator coupled to the integrator including a logic gate, a first impedance coupled across the logic gate providing positive feedback and a second impedance coupled across the logic gate providing negative feedback;

a drive circuit coupled to the oscillator; and an inductor coupled between the drive circuit and the LED wherein the LED is caused to flicker.

9. The circuit of claim 8, further comprising a circuit for developing drive waveforms for switches coupled to a resonant circuit, comprising:

a second feedback circuit coupled to the resonant circuit; and a control circuit coupled to the second feedback circuit and having first and second interconnected NAND gates, wherein the control circuit is further coupled to the switches and develops the drive waveforms wherein the resonant circuit is driven at a resonant frequency.

10. The circuit of claim 9, wherein the first NAND gate includes a first input that receives an enable signal and a second input coupled to the second feedback circuit and the control circuit further includes a capacitor coupled between an output of the second NAND gate and the second input of the first NAND gate and further wherein the first NAND gate includes an output coupled to first and second inputs of the second NAND gate.

11. The circuit of claim 10, wherein the control circuit includes a third NAND gate having a first input coupled to the output of the second NAND gate, a second input that receives the enable signal, and an output coupled to the switches.

12. The circuit of claim 11, wherein a resistor is coupled between the second input of the third NAND gate and ground potential.

13. The circuit of claim 10, wherein two pairs of switches are connected to the resonant circuit in a full-bridge configuration, and wherein the control circuit includes third and fourth NAND gates, the third NAND gate having a first input coupled to the output of the second NAND gate, a second input that receives the enable signal, and an output coupled to a first pair of the switches and the fourth NAND gate having a first input coupled to the output of the first NAND gate, a second input that receives the enable signal, and an output coupled to a second pair of the switches.

14. The circuit of claim 10, wherein a resistor is coupled between the output and the second input of the first NAND gate.

15. The circuit of claim 9, wherein the second feedback circuit includes a resistor that senses current flow through the resonant circuit.

16. The circuit of claim 9, wherein the second feedback circuit further includes a capacitor coupling the resistor to the first NAND gate.

17. The circuit of claim 8, wherein the oscillator further includes an inverter coupled between an output of logic gate and the second impedance.

18. The circuit of claim 17, wherein the first impedance is a capacitor and the second impedance is a resistor.

19. The circuit of claim 8, wherein the logic gate is an AND gate.

20. The circuit of claim 8, wherein the drive circuit comprises a plurality of inverters coupled together in parallel.

21. The circuit of claim 8, wherein the logic gate includes a first input that receives an enable signal from the microprocessor and a second input coupled to the output of the integrator.

22. The circuit of claim 8, wherein the oscillator generates a second PWM waveform that is controlled by the output of the integrator, and wherein the output of the integrator is controlled by the feedback circuit and the PWM waveform developed by the microprocessor.

* * * * *